US009663486B2

(12) United States Patent
Boivin et al.

(10) Patent No.: US 9,663,486 B2
(45) Date of Patent: May 30, 2017

(54) SELECTIVELY SUBSTITUTED QUINOLINE COMPOUNDS

(71) Applicant: EISAI R&D MANAGEMENT CO., LTD., Tokyo (JP)

(72) Inventors: Roch Boivin, North Chelmsford, MA (US); Hans Hansen, Somerville, MA (US); Sally Ishizaka, Weston, MA (US); Matthew Mackey, Melrose, MA (US); Shawn Schiller, Haverhill, MA (US); Chikako Ogawa, Basel (CH); Sridhar Narayan, Belmont, MA (US); Peter Bertinato, Old Lyme, CT (US); Gregory Berger, East Lyme, CT (US); Atsushi Endo, Andover, MA (US); Robert T. Yu, Arlington, MA (US); Lynn Hawkins, Concord, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/908,164

(22) PCT Filed: Oct. 14, 2014

(86) PCT No.: PCT/US2014/060412
§ 371 (c)(1),
(2) Date: Jan. 28, 2016

(87) PCT Pub. No.: WO2015/057655
PCT Pub. Date: Apr. 23, 2015

(65) Prior Publication Data
US 2016/0176841 A1 Jun. 23, 2016

Related U.S. Application Data
(60) Provisional application No. 61/890,858, filed on Oct. 14, 2013.

(51) Int. Cl.
| C07D 401/02 | (2006.01) |
| C07D 413/14 | (2006.01) |
| C07D 471/04 | (2006.01) |
| C07D 401/14 | (2006.01) |
| C07D 417/14 | (2006.01) |
| C07D 401/04 | (2006.01) |

(52) U.S. Cl.
CPC ......... *C07D 401/02* (2013.01); *C07D 401/04* (2013.01); *C07D 401/14* (2013.01); *C07D 413/14* (2013.01); *C07D 417/14* (2013.01); *C07D 471/04* (2013.01)

(58) Field of Classification Search
CPC .. C07D 401/02; C07D 401/14; C07D 417/14; C07D 471/04; C07D 413/14
USPC .................................................. 514/210.21
See application file for complete search history.

(56) References Cited

U.S. PATENT DOCUMENTS

| 4,399,134 A | 8/1983 | Ishikawa et al. |
| 4,552,879 A | 11/1985 | Ishikawa et al. |
| 4,933,447 A * | 6/1990 | Koono ................. C07D 401/04 544/128 |
| 5,358,949 A | 10/1994 | Tabusa et al. |
| 6,049,000 A | 4/2000 | Strohriegl et al. |
| 6,297,283 B1 | 10/2001 | Ishiwata et al. |
| 6,313,326 B1 | 11/2001 | Strohriegl et al. |
| 6,423,865 B1 | 7/2002 | Strohriegl et al. |
| 6,495,565 B2 | 12/2002 | Duan et al. |
| 6,576,642 B2 | 6/2003 | Ishiwata et al. |
| 6,605,617 B2 | 8/2003 | Renhowe et al. |
| 6,635,655 B1 | 10/2003 | Jayyosi et al. |
| 6,710,205 B2 | 3/2004 | Tani et al. |
| 6,743,807 B2 | 6/2004 | Duan et al. |
| 6,762,194 B2 | 7/2004 | Renhowe et al. |
| 6,774,237 B2 | 8/2004 | Renhowe et al. |
| 6,800,760 B2 | 10/2004 | Renhowe et al. |
| 6,897,220 B2 | 5/2005 | Delorme et al. |
| 6,933,272 B1 | 8/2005 | Helmerhorst et al. |
| 6,953,857 B2 | 10/2005 | Nazaré et al. |
| 6,984,648 B2 | 1/2006 | Lu et al. |
| 7,005,440 B1 | 2/2006 | Jayyosi et al. |
| 7,041,693 B2 | 5/2006 | Sheppeck |
| 7,067,665 B2 | 6/2006 | Nazaré et al. |
| 7,074,810 B2 | 7/2006 | King et al. |
| 7,196,198 B2 | 3/2007 | Tani et al. |
| 7,211,671 B2 | 5/2007 | Sheppeck et al. |
| 7,268,232 B2 | 9/2007 | Schlienger et al. |
| 7,312,181 B2 | 12/2007 | Lee et al. |

(Continued)

FOREIGN PATENT DOCUMENTS

| AU | 639529 B2 | 7/1993 |
| CN | 101440062 A | 5/2009 |
| CN | 101838264 A | 9/2010 |
| CN | 102675289 A | 9/2012 |
| DE | 10222166 A1 | 12/2003 |
| GB | 2396154 A | 6/2004 |
| IL | 62783 A | 1/1987 |
| JP | 58090511 | 5/1983 |
| JP | 63054363 | 3/1988 |
| JP | 8295690 | 11/1996 |

(Continued)

OTHER PUBLICATIONS

Berge et al., "Pharmaceutical Salts," Journal of Pharmaceutical Sciences, (Jan. 1977), vol. 66, No. 1, pp. 1-19.
Wang et al., "Palladium-Catalyzed Microwave-Assisted Amination of 1-Bromonaphthalenes and 5- and 8- Bromoquinolines," Organic Letters, (Jan. 2003), vol. 5, No. 6, pp. 897-900.

(Continued)

*Primary Examiner* — Kristin Vajda
(74) *Attorney, Agent, or Firm* — Buchanan Ingersoll & Rooney PC

(57) ABSTRACT

Embodiments of the disclosure relate to selectively substituted quinoline compounds that act as antagonists or inhibitors for Toll-like receptors 7 and/or 8, and their use in pharmaceutical compositions effective for treatment of systemic lupus erythematosus (SLE) and lupus nephritis.

14 Claims, 37 Drawing Sheets

(56) References Cited

U.S. PATENT DOCUMENTS

| | | |
|---|---|---|
| 7,317,024 B2 | 1/2008 | Yang |
| 7,335,774 B2 | 2/2008 | Renhowe et al. |
| 7,358,249 B2 | 4/2008 | Murai et al. |
| 7,402,696 B2 | 7/2008 | Suzuki et al. |
| 7,425,354 B2 | 9/2008 | Yanai et al. |
| RE40,558 E | 10/2008 | Jayyosi et al. |
| 7,442,475 B2 | 10/2008 | Farrand et al. |
| 7,470,709 B2 | 12/2008 | Barsanti et al. |
| 7,514,450 B2 | 4/2009 | Peters et al. |
| 7,569,583 B2 | 8/2009 | Schwink et al. |
| 7,595,343 B2 | 9/2009 | Delorme et al. |
| 7,598,268 B2 | 10/2009 | Renhowe et al. |
| 7,683,060 B2 | 3/2010 | Zhuo et al. |
| 7,776,857 B2 | 8/2010 | Cee et al. |
| 7,825,132 B2 | 11/2010 | Cai et al. |
| 7,834,035 B2 | 11/2010 | Bessis et al. |
| 7,838,547 B2 | 11/2010 | Schwink et al. |
| 7,868,204 B2 | 1/2011 | Delorme et al. |
| 7,875,624 B2 | 1/2011 | Heis et al. |
| 7,880,002 B2 | 2/2011 | Carson et al. |
| 7,902,363 B2 | 3/2011 | Facchetti et al. |
| 7,910,595 B2 | 3/2011 | Betebenner et al. |
| 7,915,408 B2 | 3/2011 | Zhuo et al. |
| 7,981,891 B2 | 7/2011 | Deak et al. |
| 7,989,458 B2 | 8/2011 | Leblanc et al. |
| 7,994,324 B2 | 8/2011 | Kolczewski et al. |
| 8,013,156 B2 | 9/2011 | Canne Bannen et al. |
| 8,030,331 B2 | 10/2011 | Bessis et al. |
| 8,088,385 B2 | 1/2012 | Chesney et al. |
| 8,088,771 B2 | 1/2012 | Melvin, Jr. et al. |
| 8,143,251 B2 | 3/2012 | Zhuo et al. |
| 8,163,741 B2 | 4/2012 | Schwink et al. |
| 8,163,775 B2 | 4/2012 | Bessis et al. |
| 8,168,788 B2 | 5/2012 | Carson et al. |
| 8,173,639 B2 | 5/2012 | Simonsen et al. |
| 8,198,299 B2 | 6/2012 | Melvin, Jr. et al. |
| 8,357,686 B2 | 1/2013 | Schwink et al. |
| 8,362,068 B2 | 1/2013 | Dousson et al. |
| 8,420,667 B2 | 4/2013 | Khanzhin et al. |
| 8,436,028 B2 | 5/2013 | Hunt et al. |
| 8,445,480 B2 | 5/2013 | Hunt et al. |
| 8,455,528 B2 | 6/2013 | Lin et al. |
| 9,126,999 B2 | 9/2015 | Boivin et al. |
| 9,428,495 B2 | 8/2016 | Carlson et al. |
| 9,446,046 B2 | 9/2016 | Boivin et al. |
| 2003/0028018 A1 | 2/2003 | Renhowe et al. |
| 2003/0055263 A1 | 3/2003 | Priepke et al. |
| 2004/0072802 A1 | 4/2004 | Duan et al. |
| 2004/0116450 A1 | 6/2004 | Oyama |
| 2004/0235834 A1 | 11/2004 | Farmer et al. |
| 2005/0137399 A1 | 6/2005 | Cai et al. |
| 2005/0203101 A1 | 9/2005 | Barsanti et al. |
| 2005/0203127 A1 | 9/2005 | Cezanne et al. |
| 2005/0209247 A1 | 9/2005 | Cai et al. |
| 2005/0256157 A1 | 11/2005 | Gesner et al. |
| 2006/0019997 A1 | 1/2006 | Edwards et al. |
| 2006/0247212 A1 | 11/2006 | Murai et al. |
| 2007/0004679 A1 | 1/2007 | Schlienger et al. |
| 2007/0185178 A1 | 8/2007 | Edwards et al. |
| 2007/0254894 A1 | 11/2007 | Kane, Jr. et al. |
| 2007/0299110 A1 | 12/2007 | Gagliardi et al. |
| 2008/0009489 A1 | 1/2008 | Schlienger et al. |
| 2008/0070906 A1 | 3/2008 | Renhowe et al. |
| 2008/0103162 A1 | 5/2008 | Oyama et al. |
| 2008/0103163 A1 | 5/2008 | Oyama et al. |
| 2008/0146576 A1 | 6/2008 | Braeuer et al. |
| 2008/0227772 A1 | 9/2008 | Peters et al. |
| 2008/0306055 A1 | 12/2008 | Egner et al. |
| 2009/0118233 A1 | 5/2009 | Murai et al. |
| 2009/0181979 A1 | 7/2009 | Cai et al. |
| 2009/0221824 A1 | 9/2009 | Briner et al. |
| 2009/0281100 A1 | 11/2009 | Barsanti et al. |
| 2009/0326020 A1 | 12/2009 | Miller et al. |
| 2010/0004284 A1 | 1/2010 | Farina et al. |
| 2010/0041891 A1 | 2/2010 | Setoh et al. |
| 2010/0130482 A1 | 5/2010 | Peters et al. |
| 2010/0160355 A1 | 6/2010 | DeGoey et al. |
| 2010/0168138 A1 | 7/2010 | DeGoey et al. |
| 2010/0184754 A1 | 7/2010 | Renhowe et al. |
| 2010/0204234 A1 | 8/2010 | Hartmann et al. |
| 2010/0222353 A1 | 9/2010 | Humphrey |
| 2010/0298378 A1 | 11/2010 | Schwink et al. |
| 2011/0021531 A1 | 1/2011 | Chobanian et al. |
| 2011/0059958 A1 | 3/2011 | Nishida et al. |
| 2011/0130381 A1 | 6/2011 | Bastos et al. |
| 2011/0135650 A1 | 6/2011 | Chackalamannil et al. |
| 2011/0144056 A1 | 6/2011 | Lin et al. |
| 2011/0144107 A1 | 6/2011 | Chatterjee et al. |
| 2011/0144119 A1 | 6/2011 | Chobanian et al. |
| 2011/0212975 A1 | 9/2011 | Kao et al. |
| 2011/0230476 A1 | 9/2011 | Niu et al. |
| 2011/0257196 A1 | 10/2011 | Lu et al. |
| 2011/0275595 A1 | 11/2011 | Eckhardt et al. |
| 2011/0312944 A1 | 12/2011 | Bartolozzi et al. |
| 2011/0319420 A1 | 12/2011 | Yang et al. |
| 2012/0071524 A1 | 3/2012 | Lu et al. |
| 2012/0122847 A1 | 5/2012 | Cee et al. |
| 2012/0142701 A1 | 6/2012 | Kao et al. |
| 2012/0149715 A1 | 6/2012 | Kao et al. |
| 2012/0165298 A1 | 6/2012 | Miller-Moslin et al. |
| 2012/0177749 A1 | 7/2012 | Tapolsky et al. |
| 2012/0190654 A1 | 7/2012 | Chen et al. |
| 2012/0202828 A1 | 8/2012 | Castro Pineiro et al. |
| 2012/0208826 A1 | 8/2012 | Reddy et al. |
| 2012/0214787 A1 | 8/2012 | Bartolozzi et al. |
| 2012/0214803 A1 | 8/2012 | Buhr et al. |
| 2012/0252721 A1 | 10/2012 | Dousson et al. |
| 2012/0258949 A1 | 10/2012 | Varasi et al. |
| 2012/0264749 A1 | 10/2012 | Hadida-Ruah et al. |
| 2012/0277434 A1 | 11/2012 | Cai et al. |
| 2012/0289495 A1 | 11/2012 | Baloglu et al. |
| 2012/0322803 A1 | 12/2012 | Steurer |
| 2013/0012526 A1 | 1/2013 | Nantermet et al. |
| 2013/0018058 A1 | 1/2013 | Cai et al. |
| 2013/0030000 A1 | 1/2013 | Chobanian et al. |
| 2013/0039944 A1 | 2/2013 | Iadonato et al. |
| 2013/0039945 A1 | 2/2013 | Iadonato et al. |
| 2013/0059883 A1 | 3/2013 | Baloglu et al. |
| 2013/0065895 A1 | 3/2013 | Conn et al. |
| 2013/0096110 A1 | 4/2013 | Conn et al. |
| 2013/0115311 A1 | 5/2013 | Charrier et al. |
| 2013/0115312 A1 | 5/2013 | Charrier et al. |
| 2013/0115313 A1 | 5/2013 | Charrier et al. |
| 2013/0116231 A1 | 5/2013 | Wilson et al. |
| 2013/0123270 A1 | 5/2013 | Carson et al. |
| 2013/0324547 A1 | 12/2013 | Boivin et al. |
| 2015/0105370 A1 | 4/2015 | Carlson et al. |
| 2016/0030430 A1 | 2/2016 | Boivin et al. |
| 2016/0176841 A1 | 6/2016 | Boivin et al. |
| 2016/0326161 A1 | 11/2016 | Carlson et al. |

FOREIGN PATENT DOCUMENTS

| | | |
|---|---|---|
| JP | 2005132834 A | 5/2005 |
| JP | 2007045752 A | 2/2007 |
| JP | 2007131765 A | 5/2007 |
| JP | 2009037104 A | 2/2009 |
| JP | 2009108152 A | 5/2009 |
| JP | 2009149754 A | 7/2009 |
| JP | 2009242540 A | 10/2009 |
| JP | 2010059131 A | 3/2010 |
| JP | 2010066630 A | 3/2010 |
| JP | 2011006360 A | 1/2011 |
| JP | 2011008205 A | 1/2011 |
| JP | 2011042606 A | 3/2011 |
| JP | 2011207765 A | 10/2011 |
| WO | 9857936 A1 | 12/1998 |
| WO | 0108488 A1 | 2/2001 |
| WO | 0218335 A1 | 3/2002 |
| WO | 03024448 A2 | 3/2003 |
| WO | 2004018419 A2 | 3/2004 |
| WO | 2004087835 A1 | 10/2004 |
| WO | 2005/007672 A2 | 1/2005 |
| WO | 2005028488 A1 | 3/2005 |

(56) References Cited

FOREIGN PATENT DOCUMENTS

| WO | 2005087217 | A1 | 9/2005 |
|---|---|---|---|
| WO | 2005115361 | A2 | 12/2005 |
| WO | 2009058730 | A1 | 5/2009 |
| WO | 2009139438 | A1 | 11/2009 |
| WO | 2010010187 | A | 1/2010 |
| WO | 2010048149 | A2 | 4/2010 |
| WO | 2010065717 | A1 | 6/2010 |
| WO | 2011025565 | A1 | 3/2011 |
| WO | 2011068138 | A1 | 6/2011 |
| WO | 2011109059 | A1 | 9/2011 |
| WO | 2011117381 | A1 | 9/2011 |
| WO | 2011117382 | A1 | 9/2011 |
| WO | 2011133871 | A2 | 10/2011 |
| WO | 2011155623 | A1 | 12/2011 |
| WO | 2012016133 | A2 | 2/2012 |
| WO | 2012033390 | A2 | 3/2012 |
| WO | 2012052540 | A1 | 4/2012 |
| WO | 2012058645 | A1 | 5/2012 |
| WO | 2012084219 | A1 | 6/2012 |
| WO | 2012128582 | A2 | 9/2012 |
| WO | 2013004332 | A | 1/2013 |
| WO | 2013009810 | A1 | 1/2013 |
| WO | 2013009827 | A1 | 1/2013 |
| WO | 2013009830 | A1 | 1/2013 |
| WO | 2013042139 | A1 | 3/2013 |
| WO | 2015057655 | A1 | 4/2015 |
| WO | 2015057659 | A1 | 4/2015 |

OTHER PUBLICATIONS

International Search Report (Form PCT/ISA/210) and the Written Opinion of the International Searching Authority (Form PCT/ISA/237) mailed on Jan. 26, 2015, by the European Patent Office in corresponding International Application No. PCT/US2014/060412. (9 pages).
Non-Final Office Action in U.S. Appl. No. 14/513,556, "Selectively Substituted Quinoline Compounds", 2015.
Excerpt of http://www.sigmaaldrich.com/life-science/cell-culture/classical-media-salts/dmem.html, accessed Dec. 16, 2015, and cited on p. 5 of Dec. 21, 2015 Office Action in U.S. Appl. No. 14/513,556.
Banchereau et al., "Type I Interferon in Systemic Lupus Erythematosus and Other Autoimmune Diseases," Immunity, (Sep. 2006), vol. 25, No. 3, pp. 383-392.
Casanova et al., "Human TLRs and IL-1Rs in Host Defense: Natural Insights from Evolutionary, Epidemiological, and Clinical Genetics," Annual Review of Immunology, (2011), vol. 29, pp. 447-491.
Costedoat-Chalumeau et al., "Low Blood Concentration of Hydroxychloroquine Is a Marker for and Predictor of Disease Exacerbations in Patients with Systemic Lupus Erythematosus," Arthritis & Rheumatism, (Oct. 2006), vol. 54, No. 10, pp. 3284-3290.
Costedoat-Chalumeau et al., "Why all Systemic Lupus Erythematosus Patients Should be Given Hydroxychlorquine Treatment," Joint Bone Spine, (Jan. 2010), vol. 77, No. 1, pp. 4-5.
Deane et al., "Control of Toll-Like Receptor 7 Expression is Essential to Restrict Autoimmunity and Dendritic Cell Proliferation," Immunity, (Nov. 2007), vol. 27, No. 5, pp. 801-810.
Deng et al., "MicroRNA-3148 Modulates Allelic Expression of Toll-Like Receptor 7 Variant Associated with Systemic Lupus Erythematosus," PLOS Genetics, (Feb. 2013), vol. 9, issue. 2, e1003336, pp. 1-11.
Fairhurst et al., "Yaa Autoimmune Phenotypes are Conferred by Overexpression of TLR7," European Journal of Immunology, (Jul. 2008), vol. 38, No. 7, pp. 1971-1978.
Gorden et al., "Synthetic TLR Agonists Reveal Functional Differences between Human TLR7 and TLR8," The Journal of Immunology, (Feb. 1, 2005), vol. 174, No. 3, pp. 1259-1268.
Kirou et al., "Activation of the Interferon-alpha Pathway Identifies a Subgroup of Systemic Lupus Erythematosus Patients With Distinct Serologic Features and Active Disease," Arthritis & Rheumatism, (May 2005), vol. 52, No. 5, pp. 1491-1503.
Kono et al., "How dying Cells Alert the Immune System to Danger," Nature Reviews Immunology, (Apr. 2008), vol. 8, No. 4, pp. 279-289.
Lafyatis et al., "Antimalarial Agents: Closing the Gate on Toll-like Receptors?," Arthritis & Rheumatism, (Oct. 2006), vol. 54, No. 10, pp. 3068-3070.
Means et al., "Human Lupus Autoantibody-DNA Complexes Activate DCs Through Cooperation of CD32 and TLR9," The Journal of Clinical Investigation, (Feb. 2005), vol. 115, No. 2, pp. 407-417.
De Montigny et al., "New Route to Unsymmetrical 9,10-Disubstituted Ethynylanthracene Derivatives," Synthesis, (2006), No. 2, pp. 293-298.
Nickerson et al., "TLR9 Regulates TLR7- and MyD88-Dependent Autoantibody Production and Disease in a Murine Model of Lupus," The Journal of Immunology, (Feb. 15, 2010), vol. 184, No. 4, pp. 1840-1848.
Savarese et al., "Requirement of Toll-like Receptor 7 for Pristane-Induced Production of Autoantibodies and Development of Murine Lupus Nephritis," Arthrutis & Rheumatism, (Apr. 2008), vol. 58, No. 4, pp. 1107-1115.
Savarese et al., "U1 Small nuclear Ribonucleoprotein Immune Complexes Induce Type I Interferon in Plasmacytoid Dendritic Cells Through TLR7," Blood, (Apr. 15, 2006), vol. 107, No. 8, pp. 3229-3234.
Shen et al., "Sex-specific Association of X-linked Toll-like Receptor 7 (TLR7) with Male Systemic Lupus Erythematosus," PNAS, (Sep. 7, 2010), vol. 107, No. 36, pp. 15838-15843.
Tsuzuki et al., "Practical Synthesis of (3S,4S)-3-methoxy-4-methylaminopyrrolidine," Tetrahedron:Asymmetry, (Nov. 26, 2001), vol. 12, Issue 21, pp. 2989-2997.
Vollmer et al., "Immune Stimulation Mediated by Autoantigen Binding Sites within Small Nuclear RNAs Involves Toll-like Receptors 7 and 8," The Journal of Experimental Medicine, (Dec. 5, 2005), vol. 202, No. 11, pp. 1575-1585.
Notification of Transmittal of the International Search Report (Forms PCT/ISA/220 and PCT/ISA/210) and the Written Opinion of the International Searching Authority (Form PCT/ISA/237) Issued on Feb. 23, 2015, by the European Patent Office in International Application No. PCT/US2014/060418. (10 pages).

* cited by examiner

FIG 1C

| Gene Number | Gene Name |
|---|---|
| 1 | Bst2* |
| 2 | Ccr2 |
| 3 | Cmpk2* |
| 4 | Fcgr1* |
| 5 | Fpr1 |
| 6 | Herc6* |
| 7 | Ifi204* |
| 8 | Ifi27l2a* |
| 9 | Ifi44* |
| 10 | Ifih1* |
| 11 | Ifit1* |
| 12 | Ifit3* |
| 13 | Irf7* |
| 14 | Isg15* |
| 15 | Mmp8* |
| 16 | Mmp9 |
| 17 | Ms4a6c* |
| 18 | Oas3* |
| 19 | Oasl2* |
| 20 | Tnfsf13b* |
| 21 | Usp18* |
| 22 | Xaf1* |

Twenty two (22) genes significantly upregulated between Pristane + Vehicle vs. uninduced PBS control (P<0.05, at least 1.5 fold change)

* Significantly reduced by ER-888840 vs. vehicle-treated pristane-induced mice (19 genes) (P<0.05, at least 1.5 fold change)

* $P < 0.05$ vs. vehicle

| Gene number | Gene name |
|---|---|
| 1 | Irf7* |
| 2 | Ifi44* |
| 3 | Usp18* |
| 4 | Oas3 |
| 5 | Ifit1* |
| 6 | Ifi202b |
| 7 | Isg15* |
| 8 | Ifi204 |
| 9 | Mx1* |
| 10 | Oasl2 |
| 11 | Xaf1* |
| 12 | Ifi35 |
| 13 | Elane |
| 14 | Fcgr1 |
| 15 | Cxcl10 |
| 16 | Tnf |
| 17 | Rsad2* |
| 18 | Ccl2 |
| | |
| 18 genes were significantly upregulated between Pristane + Vehicle vs. uninduced PBS control (P<0.05, at least 1.5 fold change) ||
| * Significantly reduced by 100mg/kg ER-888840 vs. vehicle-treated pristane-induced mice (8 genes) (P<0.05, at least 1.5 fold change). No genes were affected by 33mg/kg ER-888840. ||

| ER-Number | Structure | MW | HEK/hTLR7 IC50 (uM) | HEK/hTLR9 IC50 (uM) | Chemical Name | 1H-NMR | MS |
|---|---|---|---|---|---|---|---|
| ER-878921 | C₁₅H₁₆N₄ | 252.3 | 0.3515 | 15.933 | (R)-5-(3-aminopiperidin-1-yl)quinoline-8-carbonitrile | ¹H NMR (400 MHz, METHANOL-d₄) d ppm 7.31 (d, J=7.91 Hz, 1 H) 7.67 (dd, J=8.64, 4.25 Hz, 1 H) 8.18 (d, J=7.91 Hz, 1 H) 8.65 (dd, J=8.64, 1.61 Hz, 1 H) 9.01 (dd, J=4.25, 1.61 Hz, 1 H) | |
| ER-888840 | C₁₆H₁₈N₄ | 266.3 | 0.0010 | > 2.0 | 5-((3R,5S)-3-amino-5-methylpiperidin-1-yl)quinoline-8-carbonitrile | | |
| ER-888840-HCl | C₁₆H₁₉ClN₄ | 302.8 | | | | ¹H-NMR: DMSO-d6 – 400 MHz:0.91 (d, 3H, J= 6.4 Hz), 1.12 (q, 1H, J= 12 Hz), 1.99 (m, 1H), 2.12 (d, 1H, J= 12 Hz), 2.42 (m, 1H), 2.68 (t, 1H, J= 11.2 Hz), 3.32 (d, 1H, J= 10.0 Hz), 3.43 (t, 1H, J= 11.2 Hz), 3.65 (d, 1H, J= 10.4 Hz), 7.17 (d, 1H, 10.0 Hz), 7.3-8.1 (br, 2H), 7.63 (dd, 1H, J= 4.0 & 8.8 Hz), 8.19 (d, 1H, 10.0 Hz), 8.45 (d, 1H, 8.8 Hz), 9.00 (m, 1H) | |
| ER-889591 | C₁₈H₂₂N₄ | 294.4 | 0.1910 | > 2.0 | 5-((3R,5S)-3-(dimethylamino)-5-methylpiperidin-1-yl)quinoline-8-carbonitrile | | |

FIG. 3A

| | | | | | |
|---|---|---|---|---|---|
| ER-895386-02 | [structure] C₁₇H₂₂Cl₂N₄ | 353.3 | 0.0080 | > 10.0 | (R)-5-(5-amino-3,3-dimethylpiperidin-1-yl)quinoline-8-carbonitrile dihydrochloride | |
| ER-896310 | [structure] C₁₈H₂₀N₄O | 308.4 | 0.2305 | > 10.0 | N-((3R,5S)-1-(8-cyanoquinolin-5-yl)-5-methylpiperidin-3-yl)acetamide | 1H NMR d ppm (8.83, dd, 1H), 8.57 (dd, 1H), 7.55 (d, 1H), 7.47 (dd, 1H), 7.10 (d, 1H), 4.26 (s, 1H), 4.14 (m, 1H), 3.43 (m, 1H), 3.20 (m, 1H), 2.34 (m, 2H), 2.05 (m, 2H), 1.03 (q, 1H), 0.96 (d, 3) |
| ER-896464 | [structure] C₁₆H₁₇N₃O | 267.3 | 0.0195 | > 10.0 | 5-((3R,5S)-3-hydroxy-5-methylpiperidin-1-yl)quinoline-8-carbonitrile | approx 4:1 mixture of hydroxy epimers resonances given for major isomer. 1H NMR (CDCl3) d ppm (9.02, 1H), 8.37 (dd, 1H), 7.99 (d, 1H), 7.47 (dd, 1H), 7.05 (d, 1H), 4.07 (m, 1H), 3.61 (m, 1H), 3.33 (m, 1H), 2.60 (dd, 1H), 2.41 (dd, 1H), 2.52 (m, 1H), 2.06 (m, 1H), 1.12 (q, 1H), 1.00 (d, 3H) LCMS (ESI+) calcd for: C16H17N3O(M+H+): 268.1, found 268.1 |
| ER-897184-HCl | [structure] C₁₇H₂₁ClN₄ | 316.8 | 0.0145 | 10.524 | 5-((3S,5R)-3-methyl-5-(methylamino)piperidin-1-yl)quinoline-8-carbonitrile hydrochloride | 1H NMR (CDCl3) d ppm 9.03 (d, 1H), 8.45 (d, 1H), 7.98 (d, 1H), 7.49 (dd, 1H), 7.05 (d, 1H), 4.43 (m, 1H), 3.40 (m, 1H), 2.79 (s, 3H), 2.75 (t, 1H), 2.43 (m, 1H), 2.10 (m, 1H), 1.96 (m, 1H), 1.37 (q, 1H), 1.00 (d, 1H) |

FIG. 3B

| ID | Structure | Formula | MW | | | Name | 1H NMR | LCMS |
|---|---|---|---|---|---|---|---|---|
| ER-897272 | | C20H25N5O | 351.5 | 0.0595 | 9.963 | N-((3R,5S)-1-(8-cyanoquinolin-5-yl)-5-methylpiperidin-3-yl)-2-(dimethylamino)acetamide | 1H NMR (CDCl3) d ppm 9.03 (dd, 1H), 8.49 (dd, 1H), 7.97 (d, 1H), 7.52 (dd, 1H), 7.10 (d, 1H), 7.03 (d, 1H), 4.30 (m, 1H), 3.75 (m, 1H), 3.37 (m, 1H), 2.93 (s, 2H), 2.45 (m, 2H), 2.26 (s, 6H), 2.14 (2H), 1.09 (q, 1H), 0.99 (d, 3H) | LCMS (ESI+) calcd. for: C20H25N5O (M+H+): 352.4, found 352.4 |
| ER-897273 | | C19H22N4O2 | 338.4 | 0.1740 | > 10.0 | N-((3R,5S)-1-(8-cyanoquinolin-5-yl)-5-methylpiperidin-3-yl)-2-methoxyacetamide | 1H NMR (CDCl3) d ppm 9.03 (dd, 1H), 8.48 (dd, 1H), 7.97 (d, 1H), 7.51 (dd, 1H), 7.02 (d, 1H), 6.41 (d, 1H), 4.33 (m, 1H), 3.83 (d, 2H), 3.75 (m, 1H), 3.39 (s, 3H), 3.37 (m, 1H), 2.46 (t, 1H), 2.15 (m, 2H), 1.09 (d, 1H), 1.00 (d, 3H) | LCMS (ESI+) calcd. for: C19H22N4O2 (M+H+): 339.2 found 339.2 |
| ER-897274 | | C18H21N5O | 323.4 | 0.0065 | > 10.0 | 2-amino-N-((3R,5S)-1-(8-cyanoquinolin-5-yl)-5-methylpiperidin-3-yl)acetamide | 1H NMR (CD3OD) d ppm 8.91 (dd, 1H), 8.57 (dd, 1H), 8.06 (d, 1H), 7.59 (dd, 1H), 7.16 (d, 1H), 4.21 (m, 1H), 3.65 (m, 1H), 3.37 (m, 2H), 3.33 (m, 1H), 2.50 (m, 1H), 2.08 (m, 1H), 1.62 (q, 1H), 0.99 (d, 1H) | LCMS (ESI+) calcd. for: C18 H21N5O (M+H+): 324.2, found 324.4 |
| ER-897275 | | C19H24N4O | 324.4 | 0.0480 | 9.848 | 5-((3R,5S)-3-((2-methoxyethyl)amino)-5-methylpiperidin-1-yl)quinoline-8-carbonitrile | 1H NMR (CD3OD) d ppm 9.04 (dd, 1H), 8.77 (dd, 1H), 8.23 9d, 1H), 7.79 (dd, 1H), 7.37 (d, 1H), 3.82 (m, 1H), 3.62 m, 1H), 3.56 (q, 1H), 3.47 (m, 1H), 2.87 (t, 1H), 2.77 (s, 3H), 2.55 (t, 1H), 2.37 (m, 1H), 2.20 (m, 1H), 1.21 ,q, 1H), 1.14 (t, 1H), 1.04 (d, 3H) | LCMS (ESI+) calcd. for: C19 H24N4O (M+H+): 325.2 found 325.2 |

FIG. 3C

| ID | Structure | MW | | | Name | NMR | LCMS |
|---|---|---|---|---|---|---|---|
| ER-897275-25 | C25H32N4O8 | 516.5 | 0.0480 | 9.848 | 5-((3R,5S)-3-((2-methoxyethyl)amino)-5-methylpiperidin-1-yl)quinoline-8-carbonitrile 2-hydroxypropane-1,2,3-tricarboxylate | | |
| ER-897607-HCl | C20H26ClN5O | 387.9 | 0.0400 | > 10.0 | 2-amino-N-((3R,5S)-1-(8-cyanoquinolin-5-yl)-5-methylpiperidin-3-yl)-2-methylpropanamide hydrochloride | 1H NMR (DMSO d6) d ppm 8.99 (dd, 1H), 8.46 (dd, 1H), 8.30 (d, 1H), 8.20 (br s, 2H), 8.17 (d, 1H), 7.62 (dd, 1H), 7.16 (d, 1H), 4.02 (m, 1H), 3.66 (m, 1H), 3.61 (m, 1H), 2.55 (m, 1H), 2.43 (m, 1H), 2.10 (m, 1H), 1.44 (s, 3H), 1.39 (s, 3H), 1.23 (q, 1H), 0.91 (d, 3H) | LCMS (ESI+) calcd for: C20H25N5 (M+H+): 352.2, found 352.2 |
| ER-897608-HCl | C19H24ClN5O | 373.9 | 0.0120 | > 10.0 | N-((3R,5S)-1-(8-cyanoquinolin-5-yl)-5-methylpiperidin-3-yl)-2-(methylamino)acetamide hydrochloride | 1H NMR (d6 DMSO) d ppm 8.96 (dd, 1H), 8.81 (br s, 2H), 8.63 (d, 1H), 8.46 (dd, 1H), 8.17 9d, 1H), 7.62 (dd, 1H), 7.14 (d, 1H), 4.05 (m, 1H), 3.63 (m, 2H), 3.42 (dd, 1H), 3.30 (m, 1H), 1.96 (m, 2H), 1.10 (q, 1H), 0.91 (d, 3H) | LCMS (ESI+) calcd for: C6H20N4O (M+H+): 338.2, found 338.4 |
| ER-897810-HCl | C16H21ClN4O | 320.8 | 0.3810 | 1.338 | 5-((3R,5S)-3-amino-5-methylpiperidin-1-yl)quinoline-8-carboxamide hydrochloride | 1HNMR (d6 DMSO) d ppm 10.16 (d, 1H), 8.97 (dd, 1H), 8.52 (dd, 1H),8.51 9d, 1H), 8.19 9b rs, 2H), 7.73 (d, 1H), 7.60 (dd, 1H), 7.25 9d, 1H), 3.57 (d, 1H0, 3.49 (m, 1H0, 3.242 (m, 1H), 2.2.65 (dd, 1H), 2.40 (m, 1H), 2.12 (m, 1H) 2.01 (m, 1H), 1.12 (q, 1H), 0.91 (d, 3H) | LCMS (ESI+) calcd. for: C16 H20 N4O (M+H+): 285.2, found: 285.2 |

FIG. 3D

| | | | | | |
|---|---|---|---|---|---|
| ER-897971 | [structure] C₁₈H₂₀N₄O₂ | 324.4 | 0.0040 | > 10.0 | N-{(3R,5S)-1-(8-cyanoquinolin-5-yl)-5-methylpiperidin-3-yl}-2-hydroxyacetamide | LCMS (ESI+) calcd. for C18H20N4O2 (M+H+): 325.16; found: 325.16 |
| ER-897972 | [structure] C₂₁H₂₆N₄O₂ | 366.5 | 0.0080 | > 10.0 | (S)-N-{(3R,5S)-1-(8-cyanoquinolin-5-yl)-5-methylpiperidin-3-yl}-2-hydroxy-3-methylbutanamide | LCMS (ESI+) calcd. for C21H26N4O2 (M+H+): 367.21; found: 367.21 |
| ER-897973 | [structure] C₂₃H₂₂N₄O₂ | 386.5 | 0.0200 | > 10.0 | N-{(3R,5S)-1-(8-cyanoquinolin-5-yl)-5-methylpiperidin-3-yl}-3-hydroxybenzamide | LCMS (ESI+) calcd. for C23H22N4O2 (M+H+): 387.18; found: 387.17 |
| ER-897975 | [structure] C₂₃H₂₂N₄O₂ | 386.5 | 0.1840 | > 10.0 | N-{(3R,5S)-1-(8-cyanoquinolin-5-yl)-5-methylpiperidin-3-yl}-4-hydroxybenzamide | LCMS (ESI+) calcd. for C23H22N4O2 (M+H+): 387.18; found: 387.17 |
| ER-897976 | [structure] C₁₉H₂₂N₄OS | 354.5 | 0.0490 | > 10.0 | N-{(3R,5S)-1-(8-cyanoquinolin-5-yl)-5-methylpiperidin-3-yl}-2-(methylthio)acetamide | LCMS (ESI+) calcd. for C19H22N4OS (M+H+): 355.15; found: 355.2 |
| ER-897977 | [structure] C₂₀H₂₄N₄OS | 368.5 | 0.0290 | > 10.0 | N-{(3R,5S)-1-(8-cyanoquinolin-5-yl)-5-methylpiperidin-3-yl}-2-(ethylthio)acetamide | LCMS (ESI+) calcd. for C20H24N4OS (M+H+): 369.17; found: 369.2 |

FIG. 3E

| ID | Structure | MW | Value | Value2 | Name | | LCMS |
|---|---|---|---|---|---|---|---|
| ER-897978 | C19H22N4O3S | 386.5 | 0.0270 | > 10.0 | N-((3R,5S)-1-(8-cyanoquinolin-5-yl)-5-methylpiperidin-3-yl)-2-(methylsulfonyl)acetamide | | LCMS (ESI+) calcd. for C19H22N4O3S (M+H+): 387.14; found: 387.1 |
| ER-897979 | C19H23N5O | 337.4 | 0.0030 | 3.902 | (S)-2-amino-N-((3R,5S)-1-(8-cyanoquinolin-5-yl)-5-methylpiperidin-3-yl)propanamide | | LCMS (ESI+) calcd. for C19H23N5O (M+H+): 338.19; found: 338.2 |
| ER-897980 | C19H23N5O | 337.4 | 0.0170 | 7.763 | (R)-2-amino-N-((3R,5S)-1-(8-cyanoquinolin-5-yl)-5-methylpiperidin-3-yl)propanamide | | LCMS (ESI+) calcd. for C19H23N5O (M+H+): 338.19; found: 338.2 |
| ER-897981 | C20H23N5O | 349.4 | 0.2970 | > 10.0 | 1-amino-N-((3R,5S)-1-(8-cyanoquinolin-5-yl)-5-methylpiperidin-3-yl)cyclopropanecarboxamide | | LCMS (ESI+) calcd. for C20H23N5O (M+H+): 350.19; found: 350.2 |
| ER-897982 | C19H23N5O2 | 353.4 | 0.0035 | > 10.0 | (R)-2-amino-N-((3R,5S)-1-(8-cyanoquinolin-5-yl)-5-methylpiperidin-3-yl)-3-hydroxypropanamide | | LCMS (ESI+) calcd. for C19H23N5O2 (M+H+): 354.19; found: 354.2 |
| ER-897983 | C21H25N5O | 363.5 | 0.0470 | 9.731 | (R)-N-((3R,5S)-1-(8-cyanoquinolin-5-yl)-5-methylpiperidin-3-yl)pyrrolidine-2-carboxamide | | LCMS (ESI+) calcd. for C21H25N5O (M+H+): 364.21; found: 364.2 |

FIG. 3F

| ID | Structure | MW | IC50 | ? | Name | | LCMS |
|---|---|---|---|---|---|---|---|
| ER-897984 | C21H25N5O | 363.5 | 0.1050 | >10.0 | 2-(azetidin-3-yl)-N-((3R,5S)-1-(8-cyanoquinolin-5-yl)-5-methylpiperidin-3-yl)acetamide | | LCMS (ESI+) calcd. for C21H25N5O (M+H+): 364.21; found: 364.2 |
| ER-897985 | C21H25N5O | 363.5 | 0.0630 | 3.897 | N-((3R,5S)-1-(8-cyanoquinolin-5-yl)-5-methylpiperidin-3-yl)pyrrolidine-3-carboxamide | | LCMS (ESI+) calcd. for C21H25N5O (M+H+): 364.21; found: 364.2 |
| ER-897986 | C21H27N5O | 365.5 | 0.0270 | >10.0 | 2-amino-N-((3R,5S)-1-(8-cyanoquinolin-5-yl)-5-methylpiperidin-3-yl)-3-methylbutanamide | | LCMS (ESI+) calcd. for C21H27N5O (M+H+): 366.22; found: 366.2 |
| ER-897987 | C21H27N5O | 365.5 | 0.0180 | >10.0 | (S)-2-amino-N-((3R,5S)-1-(8-cyanoquinolin-5-yl)-5-methylpiperidin-3-yl)-3-methylbutanamide | | LCMS (ESI+) calcd. for C21H27N5O (M+H+): 366.22; found: 366.2 |
| ER-897988 | C21H27N5O | 365.5 | 0.0550 | >10.0 | 5-amino-N-((3R,5S)-1-(8-cyanoquinolin-5-yl)-5-methylpiperidin-3-yl)pentanamide | | LCMS (ESI+) calcd. for C21H27N5O (M+H+): 366.22; found: 366.2 |

FIG. 3G

| ID | Structure | MW | IC50 | ? | Name | | LCMS |
|---|---|---|---|---|---|---|---|
| ER-897989 | (structure) C21H27N5O | 365.5 | 0.0030 | 7.373 | (S)-2-amino-N-((3R,5S)-1-(8-cyanoquinolin-5-yl)-5-methylpiperidin-3-yl)pentanamide | | LCMS (ESI+) calcd. for C21H27N5O (M+H+): 366.22; found: 366.2 |
| ER-897990 | (structure) C20H25N5O2 | 365.5 | 0.0090 | > 10.0 | (S)-2-amino-N-((3R,5S)-1-(8-cyanoquinolin-5-yl)-5-methylpiperidin-3-yl)-3-methoxypropanamide | | LCMS (ESI+) calcd. for C20H25N5O2 (M+H+): 368.20; found: 368.2 |
| ER-897991 | (structure) C20H25N5O2 | 367.5 | 0.2540 | > 10.0 | (2R,3S)-2-amino-N-((3R,5S)-1-(8-cyanoquinolin-5-yl)-5-methylpiperidin-3-yl)-3-hydroxybutanamide | | LCMS (ESI+) calcd. for C20H25N5O2 (M+H+): 368.20; found: 368.2 |
| ER-897992 | (structure) C22H27N5O | 377.5 | 0.1500 | > 10.0 | N-((3R,5S)-1-(8-cyanoquinolin-5-yl)-5-methylpiperidin-3-yl)piperidine-4-carboxamide | | LCMS (ESI+) calcd. for C22H27N5O (M+H+): 378.23; found: 378.2 |
| ER-897993 | (structure) C22H27N5O | 377.5 | 0.0810 | > 10.0 | N-((3R,5S)-1-(8-cyanoquinolin-5-yl)-5-methylpiperidin-3-yl)piperidine-3-carboxamide | | LCMS (ESI+) calcd. for C22H27N5O (M+H+): 378.23; found: 378.2 |

FIG. 3H

| | | | | |
|---|---|---|---|---|
| ER-897994 | 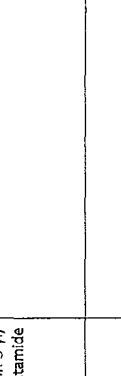 377.5 | 0.1800 | > 10.0 | N-{(3R,5S)-1-(8-cyanoquinolin-5-yl)-5-methylpiperidin-3-yl}-2-(pyrrolidin-3-yl)acetamide | LCMS (ESI+) calcd. for C22H27N5O (M+H+): 378.23; found: 378.2 |
| ER-897995 |  378.5 | 0.0840 | > 10.0 | N-{(3R,5S)-1-(8-cyanoquinolin-5-yl)-5-methylpiperidin-3-yl}piperazine-2-carboxamide | LCMS (ESI+) calcd. for C21H26N6O (M+H+): 379.22; found: 379.2 |
| ER-897996 | 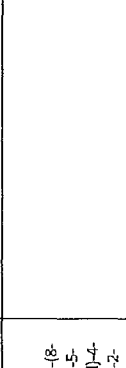 379.5 | 0.1900 | > 10.0 | (2S,4R)-N-{(3R,5S)-1-(8-cyanoquinolin-5-yl)-5-methylpiperidin-3-yl}-4-hydroxypyrrolidine-2-carboxamide | LCMS (ESI+) calcd. for C21H25N5O2 (M+H+): 380.20; found: 380.2 |
| ER-897997 |  379.5 | 0.0190 | > 10.0 | (2S,3S)-2-amino-N-{(3R,5S)-1-(8-cyanoquinolin-5-yl)-5-methylpiperidin-3-yl}-3-methylpentanamide | LCMS (ESI+) calcd. for C21H25N5O2 (M+H+): 380.20; found: 380.2 |
| ER-897998 | 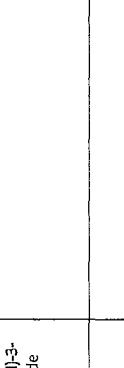 379.5 | 0.0120 | 8.446 | (R)-2-amino-N-{(3R,5S)-1-(8-cyanoquinolin-5-yl)-5-methylpiperidin-3-yl}-4-methylpentanamide | LCMS (ESI+) calcd. for C21H25N5O2 (M+H+): 380.20; found: 380.2 |

FIG. 31

| ID | Structure | MW | IC50 | Value | Name | | LCMS |
|---|---|---|---|---|---|---|---|
| ER-897999 | C₂₂H₂₉N₅O | 379.5 | 0.0090 | 7.574 | (S)-2-amino-N-((3R,5S)-1-(8-cyanoquinolin-5-yl)-5-methylpiperidin-3-yl)-4-methylpentanamide | | LCMS (ESI+) calcd. for C21H25N5O2 (M+H+): 380.20; found: 380.2 |
| ER-898000 | C₂₂H₂₉N₅O | 379.5 | 0.0490 | > 10.0 | (S)-2-amino-N-((3R,5S)-1-(8-cyanoquinolin-5-yl)-5-methylpiperidin-3-yl)-3,3-dimethylbutanamide | | LCMS (ESI+) calcd. for C21H25N5O2 (M+H+): 380.20; found: 380.2 |
| ER-898001 | C₂₂H₂₉N₅O | 379.5 | 0.0413 | 9.028 | 2-amino-N-((3R,5S)-1-(8-cyanoquinolin-5-yl)-5-methylpiperidin-3-yl)-3,3-dimethylbutanamide | | LCMS (ESI+) calcd. for C21H25N5O2 (M+H+): 380.20; found: 380.2 |
| ER-898334 | C₂₂H₂₉N₅O | 379.5 | 0.0200 | > 10.0 | N-((3R,5S)-1-(8-cyanoquinolin-5-yl)-5-methylpiperidin-3-yl)-3-methyl-2-(methylamino)butanamide | | LCMS (ESI+) calcd. for C21H25N5O2 (M+H+): 380.20; found: 380.2 |
| ER-898335 | C₂₀H₂₄N₆O₂ | 380.4 | 0.1580 | > 10.0 | (S)-2-amino-N1-((3R,5S)-1-(8-cyanoquinolin-5-yl)-5-methylpiperidin-3-yl)succinamide | | LCMS (ESI+) calcd. for C20H24N6O2 (M+H+): 381.20; found: 381.2 |
| ER-898336 | C₂₀H₂₄N₆O₂ | 380.4 | 0.0895 | > 10.0 | (S)-2-amino-N1-((3R,5S)-1-(8-cyanoquinolin-5-yl)-5-methylpiperidin-3-yl)succinamide | | LCMS (ESI+) calcd. for C20H24N6O2 (M+H+): 381.20; found: 381.2 |

FIG. 3J

| ID | Structure | MW | IC50 | ? | Name | | LCMS |
|---|---|---|---|---|---|---|---|
| ER-898337 | (structure) C20H24N6O2 | 380.4 | 0.3190 | >10.0 | (R)-2-amino-N1-((3R,5S)-1-(8-cyanoquinolin-5-yl)-5-methylpiperidin-3-yl)succinamide | | LCMS (ESI+) calcd. for C20H24N6O2 (M+H+): 381.20; found: 381.2 |
| ER-898338 | (structure) C20H23N5OS | 381.5 | 0.0629 | >10.0 | (S)-N-((3R,5S)-1-(8-cyanoquinolin-5-yl)-5-methylpiperidin-3-yl)thiazolidine-4-carboxamide | | LCMS (ESI+) calcd. for C20H23N5OS (M+H+): 382.17; found: 382.2 |
| ER-898339 | (structure) C23H23N5O | 385.5 | 0.1510 | >10.0 | 4-amino-N-((3R,5S)-1-(8-cyanoquinolin-5-yl)-5-methylpiperidin-3-yl)benzamide | | LCMS (ESI+) calcd. for C23H23N5O (M+H+): 386.19; found: 386.2 |
| ER-898341 | (structure) C23H29N5O | 391.5 | 0.0380 | >10.0 | N-((3R,5S)-1-(8-cyanoquinolin-5-yl)-5-methylpiperidin-3-yl)-2-(piperidin-4-yl)acetamide | | LCMS (ESI+) calcd. for C23H29N5O (M+H+): 392.24; found: 392.2 |
| ER-898342 | (structure) C23H29N5O | 391.5 | 0.0370 | 6.779 | N-((3R,5S)-1-(8-cyanoquinolin-3-yl)-5-methylpiperidin-3-yl)-4-methylpiperidine-4-carboxamide | | LCMS (ESI+) calcd. for C23H29N5O (M+H+): 392.24; found: 392.2 |

FIG. 3K

| | | | | | |
|---|---|---|---|---|---|
| ER-898343 | (structure) 393.5 $C_{22}H_{27}N_5O_2$ | 0.0358 | 8.031 | 1-amino-N-((3R,5S)-1-(8-cyanoquinolin-5-yl)-5-methylpiperidin-3-yl)-3-hydroxycyclopentanecarboxamide | LCMS (ESI+) calcd. for C22H27N5O2 (M+H+): 394.22; found: 394.2 |
| ER-898344 | (structure) 379.5 $C_{22}H_{29}N_5O$ | 0.0319 | > 10.0 | (S)-N-((3R,5S)-1-(8-cyanoquinolin-5-yl)-5-methylpiperidin-3-yl)-3-methyl-2-(methylamino)butanamide | LCMS (ESI+) calcd. for C23H31N5O (M+H+): 380.24; found: 380.3 |
| ER-898345 | (structure) 393.5 $C_{23}H_{31}N_5O$ | 0.0113 | 8.472 | (S)-2-amino-N-((3R,5S)-1-(8-cyanoquinolin-5-yl)-5-methylpiperidin-3-yl)-4,4-dimethylpentanamide | LCMS (ESI+) calcd. for C22H27N5O2 (M+H+): 394.22; found: 394.3 |
| ER-898346 | (structure) 393.5 $C_{23}H_{31}N_5O$ | 0.0493 | 7.903 | (S)-N-((3R,5S)-1-(8-cyanoquinolin-5-yl)-5-methylpiperidin-3-yl)-2-(methylamino)hexanamide | LCMS (ESI+) calcd. for C22H27N5O2 (M+H+): 394.22; found: 394.3 |
| ER-898347 | (structure) 394.5 $C_{21}H_{26}N_6O_2$ | 0.1480 | > 10.0 | (S)-2-amino-N1-((3R,5S)-1-(8-cyanoquinolin-5-yl)-5-methylpiperidin-3-yl)pentanediamide | LCMS (ESI+) calcd. for C21H26N6O2 (M+H+): 395.22; found: 395.2 |

FIG. 3L

| | | | | | LCMS (ESI+) calcd. for C21H27N5OS (M+H+): 398.20; found: 398.2 |
|---|---|---|---|---|---|
| ER-898348 | [structure] 397.5 C21H27N5OS | 0.0116 | 8.657 | (R)-2-amino-N-((3R,5S)-1-(8-cyanoquinolin-5-yl)-5-methylpiperidin-3-yl)-3-(ethylthio)propanamide | |
| ER-898349 | [structure] 397.5 C21H27N5OS | 0.0216 | > 10.0 | 2-amino-N-((3R,5S)-1-(8-cyanoquinolin-5-yl)-5-methylpiperidin-3-yl)-4-(methylthio)butanamide | LCMS (ESI+) calcd. for C21H27N5OS (M+H+): 398.20; found: 398.2 |
| ER-898350 | [structure] 399.5 C24H25N5O | 0.0110 | > 10.0 | (R)-2-amino-N-((3R,5S)-1-(8-cyanoquinolin-5-yl)-5-methylpiperidin-3-yl)-2-phenylacetamide | LCMS (ESI+) calcd. for C24H25N5O (M+H+): 400.21; found: 400.2 |
| ER-898351 | [structure] 399.5 C24H25N5O | 0.2300 | > 10.0 | (S)-2-amino-N-((3R,5S)-1-(8-cyanoquinolin-5-yl)-5-methylpiperidin-3-yl)-2-phenylacetamide | LCMS (ESI+) calcd. for C24H25N5O (M+H+): 400.21; found: 400.2 |
| ER-898352 | [structure] 403.5 C22H25N7O | 0.1840 | 8.476 | (S)-2-amino-N-((3R,5S)-1-(8-cyanoquinolin-5-yl)-5-methylpiperidin-3-yl)-3-(1H-imidazol-5-yl)propanamide | LCMS (ESI+) calcd. for C22H25N7O (M+H+): 404.22; found: 404.2 |
| ER-898353 | [structure] 405.5 C24H31N5O | 0.0303 | > 10.0 | N-((3R,5S)-1-(8-cyanoquinolin-5-yl)-5-methylpiperidin-3-yl)-3-(piperidin-2-yl)propanamide | LCMS (ESI+) calcd. for C24H31N5O (M+H+): 406.26; found: 406.3 |

FIG. 3M

| ID | Structure | MW | Value | Value2 | Name | | LCMS |
|---|---|---|---|---|---|---|---|
| ER-898354 | C24H31N5O | 405.5 | 0.0452 | > 10.0 | N-((3R,5S)-1-(8-cyanoquinolin-5-yl)-5-methylpiperidin-3-yl)-3-(piperidin-3-yl)propanamide | | LCMS (ESI+) calcd. for C24H31N5O (M+H+): 406.26; found: 406.3 |
| ER-898355 | C25H29N5O2 | 407.5 | 0.0874 | > 10.0 | 1-amino-N-((3R,5S)-1-(8-cyanoquinolin-5-yl)-5-methylpiperidin-3-yl)-4-hydroxycyclohexanecarboxamide | | LCMS (ESI+) calcd. for C23H29N5O2 (M+H+): 408.24; found: 408.2 |
| ER-898356 | C25H27N5O | 413.5 | 0.4590 | 7.739 | (R)-2-amino-N-((3R,5S)-1-(8-cyanoquinolin-5-yl)-5-methylpiperidin-3-yl)-3-phenylpropanamide | | LCMS (ESI+) calcd. for C25H27N5O (M+H+): 414.22; found: 414.2 |
| ER-898357 | C21H27N5O2S | 413.5 | 0.0543 | > 10.0 | (2S)-2-amino-N-((3R,5S)-1-(8-cyanoquinolin-5-yl)-5-methylpiperidin-3-yl)-4-(methylsulfinyl)butanamide | | LCMS (ESI+) calcd. for C21H27N5O2S (M+H+): 414.19; found: 414.2 |
| ER-898358 | C24H26N6O | 414.5 | 0.0438 | > 10.0 | (S)-2-amino-N-((3R,5S)-1-(8-cyanoquinolin-5-yl)-5-methylpiperidin-3-yl)-3-(pyridin-2-yl)propanamide | | LCMS (ESI+) calcd. for C24H26N6O (M+H+): 415.22; found: 415.2 |

FIG. 3N

| ID | Structure | | | | Name | | LCMS |
|---|---|---|---|---|---|---|---|
| ER-898359 | (structure) C24H26N6O | 414.5 | 0.0143 | 7.398 | (S)-2-amino-N-((3R,5S)-1-(8-cyanoquinolin-5-yl)-5-methylpiperidin-3-yl)-3-(pyridin-4-yl)propanamide | | LCMS (ESI+) calcd. for C24H26N6O (M+H+): 415.22; found: 415.2 |
| ER-898360 | (structure) C24H26N6O | 414.5 | 0.0127 | > 10.0 | (S)-2-amino-N-((3R,5S)-1-(8-cyanoquinolin-5-yl)-5-methylpiperidin-3-yl)-3-(pyridin-3-yl)propanamide | | LCMS (ESI+) calcd. for C24H26N6O (M+H+): 415.22; found: 415.2 |
| ER-898361 | (structure) C24H26N6O | 414.5 | 0.1950 | > 10.0 | (R)-2-amino-N-((3R,5S)-1-(8-cyanoquinolin-5-yl)-5-methylpiperidin-3-yl)-3-(pyridin-4-yl)propanamide | | LCMS (ESI+) calcd. for C24H26N6O (M+H+): 415.22; found: 415.2 |
| ER-898362 | (structure) C23H25N7O | 15.498 | 0.1110 | 2.613 | N-((3R,5S)-1-(8-cyanoquinolin-5-yl)-5-methylpiperidin-3-yl)-4,5,6,7-tetrahydro-1H-pyrazolo[4,3-c]pyridine-3-carboxamide | | LCMS (ESI+) calcd. for C23H25N7O (M+H+): 416.22; found: 416.2 |
| ER-898364 | (structure) C25H33N5O | 414.5 | 0.0100 | 1.857 | 2-(1-(aminomethyl)cyclohexyl)-N-((3R,5S)-1-(8-cyanoquinolin-5-yl)-5-methylpiperidin-3-yl)acetamide | | LCMS (ESI+) calcd. for C25H33N5O (M+H+): 420.27; found: 420.3 |

| ID | Structure | MW | IC50 | Value | Name | | LCMS |
|---|---|---|---|---|---|---|---|
| ER-898365 | C22H24N6OS | 403.5 | 0.0158 | 8.802 | (S)-2-amino-N-((3R,5S)-1-(8-cyanoquinolin-5-yl)-5-methylpiperidin-3-yl)-3-(thiazol-4-yl)propanamide | | LCMS (ESI+) calcd. for C22H24N6OS (M+H+): 421.18; found: 421.2 |
| ER-898366 | C26H29N5O | 427.5 | 0.4740 | 5.075 | (S)-N-((3R,5S)-1-(8-cyanoquinolin-5-yl)-5-methylpiperidin-3-yl)-2-(methylamino)-3-phenylpropanamide | | LCMS (ESI+) calcd. for C26H29N5O (M+H+): 428.24; found: 428.2 |
| ER-898367 | C26H29N5O | 427.5 | 0.4730 | 8.048 | (R)-N-((3R,5S)-1-(8-cyanoquinolin-5-yl)-5-methylpiperidin-3-yl)-2-(methylamino)-3-phenylpropanamide | | LCMS (ESI+) calcd. for C26H29N5O (M+H+): 428.24; found: 428.2 |
| ER-898368 | C25H27N5O2 | 427.5 | 0.0221 | 6.152 | (S)-2-amino-N-((3R,5S)-1-(8-cyanoquinolin-5-yl)-5-methylpiperidin-3-yl)-3-(4-hydroxyphenyl)propanamide | | LCMS (ESI+) calcd. for C25H27N5O2 (M+H+): 430.22; found: 430.2 |
| ER-898369 | C21H27N5O3S | 429.5 | 0.0451 | > 10.0 | (S)-2-amino-N-((3R,5S)-1-(8-cyanoquinolin-5-yl)-5-methylpiperidin-3-yl)-4-(methylsulfonyl)butanamide | | LCMS (ESI+) calcd. for C21H27N5O3S (M+H+): 430.19; found: 430.2 |
| ER-898758 | C18H17F3N4O | 362.4 | 0.1850 | > 10.0 | N-((3R,5S)-1-(8-cyanoquinolin-5-yl)-5-methylpiperidin-3-yl)-2,2,2-trifluoroacetamide | | |

| ID | Structure | MW | value1 | value2 | Name | NMR/LCMS |
|---|---|---|---|---|---|---|
| ER-898760 | (structure) C19H24N4O2S | 372.5 | 0.3340 | > 10.0 | N-((3R,5S)-1-(8-cyanoquinolin-5-yl)-5-methylpiperidin-3-yl)propane-2-sulfonamide | |
| ER-898761 | (structure) C19H19F3N4O | 376.4 | 0.0650 | > 10.0 | N-((3R,5S)-1-(8-cyanoquinolin-5-yl)-5-methylpiperidin-3-yl)-3,3,3-trifluoropropanamide | |
| ER-898763 | (structure) C22H29N5O | 379.5 | 0.0760 | 4.59 | (S)-3-amino-N-((3R,5S)-1-(8-cyanoquinolin-5-yl)-5-methylpiperidin-3-yl)-4-methylpentanamide | |
| ER-898765 | (structure) C20H25N5O | 351.5 | 0.0430 | 1.31 | (S)-3-amino-N-((3R,5S)-1-(8-cyanoquinolin-5-yl)-5-methylpiperidin-3-yl)butanamide | |
| ER-898771 | (structure) C18H19F3N4 | 348.4 | 0.2030 | >10.0 | 5-((3S,5R)-3-methyl-5-((2,2,2-trifluoroethyl)amino)piperidin-1-yl)quinoline-8-carbonitrile | 1H NMR (400 MHz, CHLOROFORM-d) d ppm 0.96 (d, J=11.86 Hz, 1 H) 0.99 - 1.04 (m, 3 H) 2.03 - 2.16 (m, 1 H) 2.20 (d, J=12.44 Hz, 1 H) 2.35 - 2.54 (m, 2 H) 2.92 (d, J=29.80 Hz, 1 H) 3.07 - 3.19 (m, 1 H) 3.19 - 3.35 (m, 2 H) 3.38 (dt, J=11.81, 1.96 Hz, 1 H) 3.60 (dt, J=11.27, 2.01 Hz, 1 H) 7.02 - 7.12 (m, 1 H) 7.50 (dd, J=8.54, 4.20 Hz, 1 H) 7.98 - 8.05 (m, 1 H) 8.38 (dd, J=8.55, 1.68 Hz, 1 H) 9.06 (dd, J=4.20, 1.68 Hz, 1 H) LCMS (ESI+) calcd. for C18H19F3N4 (M+H+): 349.16; found: 348.9 |

FIG. 3Q

| | | | | |
|---|---|---|---|---|
| ER-898772 | [structure] C₁₈H₂₀F₂N₄ | 330.4 | 0.1070 | > 10.0 | 5-((3R,5S)-3-((2,2-difluoroethyl)amino)-5-methylpiperidin-1-yl)quinoline-8-carbonitrile | 1H NMR (400 MHz, CHLOROFORM-d) δ ppm 0.96 (d, J=11.86 Hz, 1 H) 0.99 - 1.04 (m, 4 H) 2.03 - 2.16 (m, 1 H) 2.20 (d, J=12.44 Hz, 1 H) 2.35 - 2.54 (m, 2 H) 2.92 (d, J=29.80 Hz, 1 H) 3.07 - 3.19 (m, 1 H) 3.19 - 3.35 (m, 2 H) 3.38 (dt, J=11.81, 1.96 Hz, 1 H) 3.60 (dt, J=11.27, 2.01 Hz, 1 H) 7.02 - 7.12 (m, 1 H) 7.50 (dd, J=8.54, 4.20 Hz, 1 H) 7.98 - 8.06 (m, 1 H) 8.38 (dd, J=8.55, 1.58 Hz, 1 H) 9.06 (dd, J=4.20, 1.68 Hz, 1 H) | LCMS (ESI+) calcd. for C18H20F2N4 (M+H+): 331.17; found: 330.9 |
| ER-898881 | [structure] C₂₁H₂₅N₅O₂ | 379.5 | 0.1150 | >10.0 | N-((3R,5S)-1-(8-cyanoquinolin-5-yl)-5-methylpiperidin-3-yl)morpholine-2-carboxamide | | |
| ER-898901 | [structure] C₂₀H₂₅N₅O | 351.5 | 0.0460 | 8.82 | (S)-N-((3R,5S)-1-(8-cyanoquinolin-5-yl)-5-methylpiperidin-3-yl)-2-(methylamino)propanamide | | |
| ER-898902 | [structure] C₂₂H₂₉N₅O | 379.5 | 0.0670 | 5.23 | (R)-3-amino-N-((3R,5S)-1-(8-cyanoquinolin-5-yl)-5-methylpiperidin-3-yl)-4-methylpentanamide | | |
| ER-898912 | [structure] C₂₁H₂₁N₅O₂ | 375.4 | 0.1830 | > 10.0 | N-((3R,5S)-1-(8-cyanoquinolin-5-yl)-5-methylpiperidin-3-yl)-5-methylisoxazole-3-carboxamide | 1H NMR (CD3OD) δ ppm 8.93 (dd, 1H), 8.62 (dd, 1H), 8.08 (d, 1H), 7.62 (dd, 1H), 7.20 (d, 1H), 6.41 (s, 1H), 4.39 (m, 1H), 3.70 (m, 1H), 3.44 (m, 1H), 2.66 (ddd, 1H), 2.52 (ddd, 1H), 2.43 (s, 3H), 2.13 (m, 1H), 1.31 (q, 1H), 1.01 (d, 3H) | LCMS (ESI+) calcd. for: C21H21N5O2 (M+H+) 376.2, found 376.2 |

FIG. 3R

| ID | Structure | Formula / MW | Value | Value2 | Name | NMR | MS |
|---|---|---|---|---|---|---|---|
| ER-898976 | 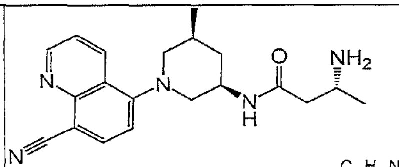 | C20H25N5O / 351.5 | 0.0320 | 0.78 | (R)-3-amino-N-((3R,5S)-1-(8-cyanoquinolin-5-yl)-5-methylpiperidin-3-yl)butanamide | | |
| ER-898977 | 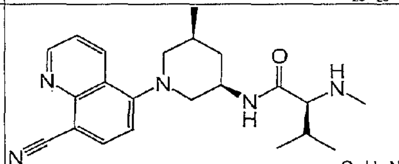 | C22H29N5O / 379.5 | 0.0480 | 9.47 | (S)-N-((3R,5S)-1-(8-cyanoquinolin-5-yl)-5-methylpiperidin-3-yl)-3-methyl-2-(methylamino)butanamide | | |
| ER-898979 | 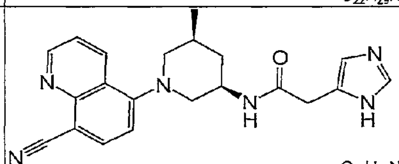 | C21H22N6O / 374.4 | 0.0280 | >10.0 | N-((3R,5S)-1-(8-cyanoquinolin-5-yl)-5-methylpiperidin-3-yl)-2-(1H-imidazol-5-yl)acetamide | 1H NMR (CD3OD) d ppm 8.89 (dd, 1H), 8.55 (dd, 1H), 8.04 (d, 1H), 7.59 (s, 1H), 7.57 (dd, 1H), 7.14 (d, 1H), 6.91 (s, 1H), 4.16 (m, 1H), 3.68 (m, 1H), 3.47 (s, 2H), 3.38 (m, 1H), 2.47 (m, 2H), 2.07 (m, 2H), 1.13 (q, 1H), 0.98 (d, 3H) | LCMS (ESI+) calcd. for: C21H22N6O (M+H+) 375.2, found 375.2 |
| ER-898980 | 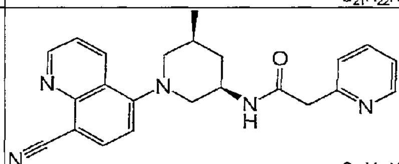 | C23H23N5O / 385.5 | 0.0930 | >10.0 | N-((3R,5S)-1-(8-cyanoquinolin-5-yl)-5-methylpiperidin-3-yl)-2-(pyridin-2-yl)acetamide | 1H NMR (CDCl3) d 9.02 (dd, 1H), 8.53 (m, 1H), 8.47 (dd, 1H), 7.95 (D, 1H), 7.65 (m, 1H), 7.51 (m, 2H), 7.18 (m, 1H), 7.00 (d, 1H), 4.26 9m, 1HO, 3.77 (m, 1H), 3.70 (s, 2H), 3.35 (m, 1H), 2.43 (m, 12H), 2.12 (m, 2H), 1.06 (q, 1H), 0.98. (d, 3H) | [ESI+] calcd. for: C23H23N5O 385.2, found 386.2 (M+1) |
| ER-898981 | 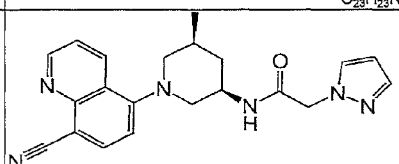 | C21H22N6O / 374.4 | 0.1040 | >10.0 | N-((3R,5S)-1-(8-cyanoquinolin-3-yl)-5-methylpiperidin-3-yl)-2-(1H-pyrazol-1-yl)acetamide | 1H NMR (CDCl3) d 9.03 (dd, 1H), 8.45 (dd,1H), 7.97 (d, 1H), 7.61 (d, 1H), 7.51 (dd, 1H), 7.44 (d, 1H), 7.00 (d, 1H), 6.36 (d, 1H), 6.33 (dd, 1H), 4.79, s, 2H), 4.24 (m, 1H), 3.69 (m, 1H), 3.34 (m, 1H), 2.40 (m, 2H), 2.09 (m, 2H), 0.98 d, 3H). 0.96 ( q, 1H) | LCMS (ESI+) calcd. for: C21H22N6O (M+H+) 375.2, found 375.2 |
| ER-898982 | 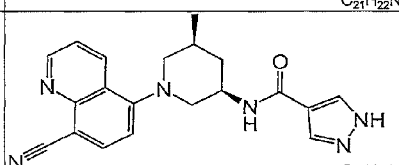 | C20H20N6O / 360.4 | 0.1950 | >10.0 | N-((3R,5S)-1-(8-cyanoquinolin-5-yl)-5-methylpiperidin-3-yl)-1H-pyrazole-4-carboxamide | H1 NMR (CD3OD) d ppm 8.89 (dd, 1H), 8.57 (dd, 1H), 8.04 (s, 1H), 8.02 (d, 1H), 7.58 (dd, 1H), 7.14 (d, 1H), 4.87 (s, 1H), 4.34 (m, 1H), 3.73 (dd, 1H), 3.40 (m, 1H), 2.57 (dd, 1H), 2.48 (dd, 1H), 2.12 (m, 1H), 1.25 (q, 1H), 0.99 (d, 3H) | LCMS (ESI+) calcd. for: C20H20N6O (M+H+) 361.2, found 361.2 |

FIG. 3S

| ID | Structure | MW | | | Name | 1H NMR | LCMS |
|---|---|---|---|---|---|---|---|
| ER-898984 | C22H21N5O | 371.4 | 0.2170 | >10.0 | N-((3R,5S)-1-(8-cyanoquinolin-5-yl)-5-methylpiperidin-3-yl)nicotinamide | 1H NMR (CD3OD), d ppm 8.84 (m, 2H), 8.64 (m, 2H), 8.21 (m, 1H), 8.07 (d, 1H), 7.63 (dd, 1H), 7.50 (m, 1H), 7.20 (d, 1H), 4.42 (m, 1H), 3.78 (m, 1H), 3.45 (m, 1H), 2.64 (dd, 1H), 2.53 (dd, 1H), 2.18 (m, 1H), 1.31 (q, 1H), 1.03 (d, 3H) | LCMS (ESI+) calcd. for: C22H21N5O (M+2H+) 373.2, found 373.2 |
| ER-898985 | C21H22N6O | 374.4 | 0.0830 | >10.0 | N-((3R,5S)-1-(8-cyanoquinolin-3-yl)-5-yl)-5-methylpiperidin-3-yl)-1-methyl-1H-imidazole-5-carboxamide | 1H NMR (CD3OD) mixture of rotamers d ppm 8.92 (m, 1H), 8.60 (m, 1H), 8.07 (dd, 1H), 7.69 (s, 1H), 7.62 (m, 1H), 7.76 (s, 1H), 7.18 (dd, 1H), 4.34 (m, 1H), 3.98 (m, 1H), 3.87 (s, 3H), 3.71 (m, 2H), 3.42 (m, 2H), 2.52-2.41 (m, 2H) 1.012-0.96 (m, 3H) | LCMS (ESI+) calcd. for: C21H22N6O (M+H+) 375.2, found 375.2 |
| ER-898986 | C21H22N6O | 374.4 | 0.2620 | >10.0 | N-((3R,5S)-1-(8-cyanoquinolin-5-yl)-5-methylpiperidin-3-yl)-1-methyl-1H-pyrazole-5-carboxamide | 1H NMR (CD3OD) d ppm 8.92 (dd, 1H), 8.61 (dd, 1H), 8.07 (d, 1H), 7.61 (dd, 1H), 7.41 (d, 1H), 7.20 (d, 1H), 6.76 (d, 1H), 4.35 (m, 1H), 4.06 (s, 3H), 3.72 (m, 1H), 3.43 (m, 1H), 2.61 (dd, 1H), 2.51 (dd, 1H), 2.15 (m, 1H), 1.27 (q, 1H), 1.01 (d, 3H) | LCMS (ESI+) calcd. for: C21H22N6O (M+H+) 375.2, found 375.2 |
| ER-898991 | C19H20F3N5O | 391.4 | 0.0400 | >10.0 | (S)-2-amino-N-((3R,5S)-1-(8-cyanoquinolin-5-yl)-5-methylpiperidin-3-yl)-3,3,3-trifluoropropanamide | | |
| ER-898993 | C19H20F3N5O | 391.4 | 0.1010 | >10.0 | (R)-2-amino-N-((3R,5S)-1-(8-cyanoquinolin-5-yl)-5-methylpiperidin-3-yl)-3,3,3-trifluoropropanamide | | |

FIG. 3T

| | | | | | |
|---|---|---|---|---|---|
| ER-899014 | [structure] C₁₉H₂₁F₃N₄ | 362.4 | 0.0240 | > 10.0 | 5-[(3S,5R)-3-methyl-5-((3,3,3-trifluoropropyl)amino)piperidin-1-yl]quinoline-8-carbonitrile | 1H NMR (400 MHz, CHLOROFORM-d) d ppm 1.03 (d, J=6.52 Hz, 4 H) 1.08 (dd, J=23.70, 11.80 Hz, 1 H) 2.08 - 2.25 (m, 2 H) 2.43 - 2.53 (m, 2 H) 3.40 (dt, J=11.74, 1.85 Hz, 1 H) 3.75 - 3.84 (m, 1 H) 4.34 - 4.47 (m, 1 H) 5.46 (d, J=7.44 Hz, 1 H) 7.05 (d, J=8.01 Hz, 1 H) 7.52 - 7.57 (m, 1 H) 8.00 (d, J=7.97 Hz, 1 H) 8.18 (s, 1 H) 8.48 (dd, J=8.58, 1.68 Hz, 1 H) 9.05 (dd, J=4.22, 1.66 Hz, 1 H) LCMS (ESI+) calcd. for C19H21F3N4 (M+H+): 363.18, found: 363.3 |
| ER-899016 | [structure] C₁₈H₁₉N₅ | 305.4 | 0.0050 | 8.355 | 5-[(3R,5S)-3-((cyanomethyl)amino)-5-methylpiperidin-1-yl]quinoline-8-carbonitrile | 1H NMR (400 MHz, CHLOROFORM-d) d ppm 0.91 - 1.12 (m, 6 H) 2.08 - 2.25 (m, 3 H) 2.35 - 2.60 (m, 3 H) 3.22 - 3.45 (m, 3 H) 3.52 - 3.79 (m, 3 H) 7.07 (d, J=7.93 Hz, 1 H) 7.47 - 7.59 (m, 1 H) 8.01 (dd, J=7.95, 0.97 Hz, 1 H) 8.42 (d, J=8.55 Hz, 1 H) 8.99 - 9.13 (m, 1 H) LCMS (ESI+) calcd. for C18H19N5 (M+H+): 306.17, found: 305.9 |
| ER-899072 | [structure] C₂₁H₂₄N₄O₂ | 364.4 | 0.0241 | >10.0 | N-[(3R,5S)-1-(8-cyanoquinolin-5-yl)-5-methylpiperidin-3-yl]-3-methyloxetane-3-carboxamide | |
| ER-899075 | [structure] C₂₁H₂₅N₅O | 350.5 | 0.1615 | >10.0 | 5-[(3S,5R)-3-methyl-5-(((3-methyloxetan-3-yl)methyl)amino)piperidin-1-yl]quinoline-8-carbonitrile | |
| ER-899127 | [structure] C₂₁H₂₅N₅O₂ | 379.5 | 0.0520 | >10.0 | (R)-N-((3R,5S)-1-(8-cyanoquinolin-5-yl)-5-methylpiperidin-3-yl)morpholine-3-carboxamide | 1H NMR (400 MHz, CHLOROFORM-d) d ppm 1.01 (d, J=6.37 Hz, 4 H) 1.11 (q, J=11.76 Hz, 2 H) 1.19 - 1.28 (m, 1 H) 1.28 - 1.43 (m, 2 H) 2.06 - 2.36 (m, 8 H) 2.22 - 2.22 (m, 1 H) 2.45 (q, J=11.39 Hz, 3 H) 2.88 - 3.07 (m, 2 H) 3.08 - 3.17 (m, 1 H) 3.38 (d, J=9.99 Hz, 1 H) 3.51 (dd, J=8.01, 3.51 Hz, 1 H) 3.58 (ddd, J=11.38, 7.01, 4.35 Hz, 1 H) 3.65 (dd, J=11.18, 8.24 Hz, 1 H) 3.74 (d, J=11.44 Hz, 2 H) 3.97 (dd, J=11.37, 3.36 Hz, 1 H) 4.20 - 4.35 (m, 1 H) 6.97 - 7.09 (m, 2 H) 7.53 (ddd, J=8.54, 4.18, 1.20 Hz, 1 H) 7.97 (dd, J=7.97, 1.22 Hz, 1 H) 8.44 - 8.53 (m, 1 H) 8.99 - 9.07 (m, 1 H) LCMS (ESI+) calcd. for C21H25N5O2 (M+H+): 381.20, found: 381 |

FIG. 3U

| Compound | Structure | Formula | MW | IC50 | >value | Name | NMR | LCMS |
|---|---|---|---|---|---|---|---|---|
| ER-899128 | (morpholine carboxamide, piperidine, cyanoquinoline) | C21H25N5O2 | 379.5 | 0.1970 | >10.0 | (S)-N-((3R,5S)-1-(8-cyanoquinolin-5-yl)-5-methylpiperidin-3-yl)morpholine-3-carboxamide | 1H NMR (400 MHz, CHLOROFORM-d) d ppm 0.98 (d, J=6.37 Hz, 3 H) 1.10 (dd, J=24.07, 11.90 Hz, 1 H) 1.18 - 1.39 (m, 3 H) 1.96 - 2.20 (m, 2 H) 2.29 - 2.56 (m, 2 H) 2.74 - 3.03 (m, 3 H) 3.11 (q, J=7.34 Hz, 1 H) 3.36 (d, J=10.07 Hz, 1 H) 3.45 - 3.65 (m, 3 H) 3.55 - 3.81 (m, 2 H) 3.83 - 4.03 (m, 1 H) 4.10 - 4.33 (m, 1 H) 7.02 (d, J=8.01 Hz, 1 H) 7.15 (d, J=7.78 Hz, 1 H) 7.51 (dd, J=8.53, 4.18 Hz, 1 H) 7.96 (d, J=7.97 Hz, 1 H) 8.44 (dd, J=8.53, 1.43 Hz, 1 H) 9.01 (dd, J=4.10, 1.43 Hz, 1 H) | LCMS (ESI+) calcd. for C21H25N5O2 (M+H+): 381.20, found: 381 |
| ER-899350-HCl | (oxetane carboxamide NH2, piperidine, cyanoquinoline) HCl | C20H24ClN5O2 | 401.9 | 0.1240 | >10.0 | 3-amino-N-((3R,5S)-1-(8-cyanoquinolin-5-yl)-5-methylpiperidin-3-yl)oxetane-3-carboxamide hydrochloride | 1H NMR (d4 DMSO) d ppm 8.98 (dd, 1H0, 8.59 (d, 1H), 8.47 (dd, 1H), 8.18 (d, 1H), 7.95 (br s, 2H), 7.63 (m, 1H), 7.16 (d, 1H), 4.78 (dd, 2H), 4.51 (dd, 2H), 4.10 (m, 1H), 3.52 (m, 1H), 3.37 (m, 1H), 2.62 (dd, 1H), 2.45 (dd, 1H), 1.99 (m, 1H), 1.29 (q, 1H), 0.91 (d, 3H) | |
| ER-899369-HCl | (oxetane CH2NH2, piperidine, cyanoquinoline) HCl | C20H25ClN5O | 387.9 | 0.0090 | >10.0 | 5-((3R,5S)-3-(((3-aminooxetan-3-yl)methyl)amino)-5-methylpiperidin-1-yl)quinoline-8-carbonitrile hydrochloride | 1H NMR (d6 DMSO) d ppm 9.00 (dd, 1H), 8.45 (dd, 1H), 8.20 (, 1H), 7.64 (dd, 1H), 7.19 (d, 1H), 4.52 (s, 4H), 3.97 (dd, 1H), 3.73 (m 1H), 3.34 (m, 2H), 2.68 (m, 1H), 2.42 (m, 1H), 2.21, (m, 1H), 1.94 (s, 2H), 1.12 (q, 1H), 0.91 (d, 3H | LCMS (ESI+) calcd. For C20H24N4O2 (M+H+): 352.2, found 352.2 |
| ER-899504 | (ethyl acetate NH, piperidine, cyanoquinoline) | C20H24N4O2 | 352.4 | 0.0900 | >10.0 | ethyl 2-(((3R,5S)-1-(8-cyanoquinolin-5-yl)-5-methylpiperidin-3-yl)amino)acetate | | LCMS (ESI+) calcd. for C20H24N4O2 (M+H+): 353.19, found: 353 |
| ER-899505 | (diethyl diacetate N, piperidine, cyanoquinoline) | C24H30N4O4 | 438.5 | 0.0720 | >10.0 | diethyl 2,2'-(((3R,5S)-1-(8-cyanoquinolin-5-yl)-5-methylpiperidin-3-yl)azanediyl)diacetate | 1H NMR (400 MHz, CHLOROFORM-d) d ppm 0.87 (t, J=6.90 Hz, 1 H) 0.99 (d, J=6.60 Hz, 3 H) 1.10 (q, J=11.85 Hz, 1 H) 1.19 - 1.43 (m, 8 H) 1.95 - 2.09 (m, 1 H) 2.14 (d, J=12.21 Hz, 1 H) 2.38 (t, J=11.41 Hz, 1 H) 2.62 (t, J=11.10 Hz, 1 H) 3.22 - 3.41 (m, 2 H) 3.56 - 3.71 (m, 4 H) 4.05 - 4.29 (m, 4 H) 7.04 (d, J=8.01 Hz, 1 H) 7.48 (dd, J=8.55, 4.20 Hz, 1 H) 7.99 (d, J=8.01 Hz, 1 H) 8.38 (dd, J=8.55, 1.68 Hz, 1 H) 9.04 (dd, J=4.20, 1.68 Hz, 1 H) | LCMS (ESI+) calcd. for C24H30N4O4 (M+H+): 439.29, found: 439 |

FIG. 3V

| | | | | | |
|---|---|---|---|---|---|
| ER-899506 | 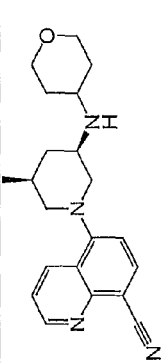<br>$C_{21}H_{26}N_4O$ | 350.5 | 0.0280 | >10.0 | 5-((3S,5R)-3-methyl-5-((tetrahydro-2H-pyran-4-yl)amino)piperidin-1-yl)quinoline-8-carbonitrile | 1H NMR (400 MHz, CHLOROFORM-d) d ppm 1.00 (d, J=6.52 Hz, 4 H) 1.45 (d, J=9.61 Hz, 1 H) 1.74 - 2.00 (m, 2 H) 2.02 - 2.26 (m, 2 H) 2.40 (t, J=11.41 Hz, 1 H) 2.87 (t, J=10.43 Hz, 1 H) 3.32 - 3.48 (m, 4 H) 3.60 (d, J=9.27 Hz, 1 H) 3.99 (dd, J=7.02, 4.46 Hz, 2 H) 7.08 (d, J=8.01 Hz, 1 H) 7.50 (dd, J=8.53, 4.22 Hz, 1 H) 8.03 (d, J=7.97 Hz, 1 H) 8.40 (dd, J=8.54, 1.60 Hz, 1 H) 9.07 (dd, J=4.16, 1.60 Hz, 1 H) | LCMS (ESI+) calcd. for C21H26N4O (M+H+): 351.21, found: 350.9 |
| ER-899508 | 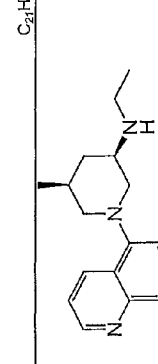<br>$C_{18}H_{22}N_4$ | 294.4 | 0.1450 | >10.0 | 5-((3R,5S)-3-(ethylamino)-5-methylpiperidin-1-yl)quinoline-8-carbonitrile | 1H NMR (400 MHz, CHLOROFORM-d) d ppm 1.03 (d, J=6.52 Hz, 4 H) 1.08 (dd, J=23.70, 11.80 Hz, 1 H) 2.08 - 2.25 (m, 2 H) 2.43 - 2.53 (m, 2 H) 3.40 (dt, J=11.74, 1.85 Hz, 1 H) 3.76 - 3.84 (m, 1 H) 4.34 - 4.47 (m, 1 H) 5.46 (d, J=7.44 Hz, 1 H) 7.05 (d, J=8.01 Hz, 1 H) 7.52 - 7.57 (m, 1 H) 8.00 (d, J=7.97 Hz, 1 H) 8.18 (s, 1 H) 8.48 (dd, J=8.58, 1.68 Hz, 1 H) 9.05 (dd, J=4.22, 1.66 Hz, 1 H) | LCMS (ESI+) calcd. for C18H22N4 (M+H+): 295.19, found: 295 |
| ER-899541 | 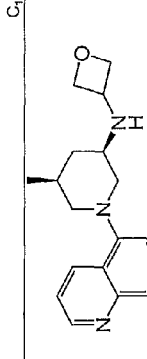<br>$C_{19}H_{22}N_4O$ | 322.4 | 0.0140 | >10.0 | 5-((3S,5R)-3-methyl-5-(oxetan-3-ylamino)piperidin-1-yl)quinoline-8-carbonitrile | 1H NMR (400 MHz, METHANOL-d4) d ppm 0.89 - 1.07 (m, 4 H) 2.03 - 2.17 (m, 3 H) 2.37 - 2.56 (m, 2 H) 2.93 - 3.09 (m, 1 H) 3.35 (s, 1 H) 3.41 (dt, 1 H) 3.47 - 3.57 (m, 1 H) 4.11 - 4.23 (m, 1 H) 4.51 (dt, 1 H) 4.78 (t, 1 H) 4.84 (t, 1 H) 7.20 (d, 1 H) 7.63 (dd, 1 H) 8.05 - 8.17 (m, 1 H) 8.52 (d, 1 H) 8.96 (dd, 1 H) | LCMS (ESI+) calcd. for C19H22N4O (M+H+): 323.18, found: 323.18 |
| ER-899543 | 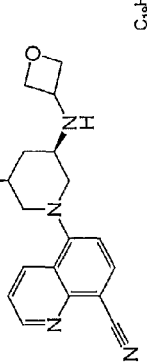<br>$C_{23}H_{22}F_3N_5$ | 425.5 | 0.0480 | >10.0 | 5-((3S,5R)-3-methyl-5-(((5-(trifluoromethyl)pyridin-2-yl)methyl)amino)piperidin-1-yl)quinoline-8-carbonitrile | 1H NMR (400 MHz, METHANOL-d4) d ppm 0.88 - 1.10 (m, 3 H) 2.08 (dd, 1 H) 2.25 (d, 1 H) 2.47 (t, 1 H) 2.57 (t, 1 H) 2.99 - 3.22 (m, 1 H) 3.33 - 3.48 (m, 1 H) 3.73 (d, 1 H) 3.93 - 4.19 (m, 2 H) 4.77 (s, 1 H) 7.10 - 7.26 (m, 1 H) 7.58 (dd, 1 H) 7.68 (d, 1 H) 7.75 (d, 1 H) 8.03 - 8.20 (m, 2 H) 8.46 (dd, 1 H) 8.79 (br. s., 1 H) 8.85-8.93 (m, 1H) | LCMS (ESI+) calcd. for C23H22F3N5 (M+H+): 426.19, found: 426.45 |
| ER-899544 | 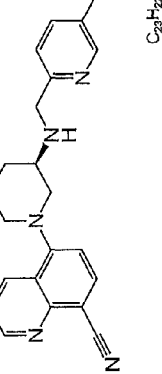<br>$C_{20}H_{24}N_4O$ | 322.4 | 0.0400 | >10.0 | 5-((3S,5R)-3-methyl-5-((tetrahydrofuran-3-yl)amino)piperidin-1-yl)quinoline-8-carbonitrile | 1H NMR (400 MHz, METHANOL-d4) d ppm 0.82 -1.11 (m, 6 H) 1.18 - 1.38 (m, 1 H) 1.63 - 1.85 (m, 1 H) 2.00 - 2.28 (m, 2 H) 2.35 - 2.58 (m, 2 H) 2.99 - 3.16 (m, 1 H) 3.37 (d, 1 H) 3.42 - 3.59 (m, 1 H) 3.59 - 3.68 (m, 1 H) 3.72 (tt, 1 H) 3.77 - 3.97 (m, 1 H) 7.12 - 7.24 (m, 1 H) 7.56 (dd,1 H) 7.96 - 8.08 (m, 1 H) 8.47 (d, 1 H) 8.89 (br. s., 1 H) | LCMS (ESI+) calcd. for C20H24N4O (M+H+): 337.20, found: 337.43 |

FIG. 3W

| ID | Structure | | | NMR / MS |
|---|---|---|---|---|
| ER-899547 | [structure] C18H21N5O | 323.4 | 0.0695 | > 10.0 | 2-(((3R,5S)-1-(8-cyanoquinolin-5-yl)-5-methylpiperidin-3-yl)amino)acetamide | 1H NMR (400 MHz, CHLOROFORM-d) d ppm 0.88 - 1.08 (m, 4 H) 1.79 (br. s., 3 H) 1.98 - 2.15 (m, 1 H) 2.21 (d, J=12.47 Hz, 1 H) 2.34 - 2.55 (m, 2 H) 3.00 (tt, J=10.74, 3.96 Hz, 1 H) 3.28 - 3.47 (m, 3 H) 3.54 - 3.66 (m, 1 H) 5.86 (br. s., 1 H) 7.05 (d, J=8.01 Hz, 2 H) 7.50 (dd, J=8.51, 4.20 Hz, 1 H) 7.99 (d, J=7.97 Hz, 1 H) 8.36 (dd, J=8.53, 1.55 Hz, 1 H) 9.03 (dd, J=4.12, 1.53 Hz, 1 H) | LCMS (ESI+) calcd. for C18H21N5O (M+H+): 324.18, found: 324 |
| ER-899548 | [structure] C19H23N5O | 337.4 | 0.0350 | > 10.0 | 2-(((3R,5S)-1-(8-cyanoquinolin-5-yl)-5-methylpiperidin-3-yl)amino)-N-methylacetamide | 1H NMR (400 MHz, METHANOL-d4) d ppm 0.90 - 1.09 (m, 4 H) 1.28 (br. s., 1 H) 2.37 - 2.61 (m, 2 H) 2.76 (s, 3 H) 3.00 (br. s., 1 H) 3.61 (br. s., 4 H) 7.22 (d, J=8.01 Hz, 1 H) 7.62 (dd, J=8.60, 4.22 Hz, 1 H) 8.12 (d, J=8.01 Hz, 1 H) 8.53 (dd, J=8.65, 1.71 Hz, 1 H) 8.96 (dd, J=4.27, 1.71 Hz, 1 H) | LCMS (ESI+) calcd. for C19H23N5O (M+H+): 338.19, found: 338 |
| ER-899549 | [structure] C20H25N5O | 351.5 | 0.0430 | > 10.0 | 2-(((3R,5S)-1-(8-cyanoquinolin-5-yl)-5-methylpiperidin-3-yl)amino)-N-ethylacetamide | 1H NMR (400 MHz, CHLOROFORM-d) d ppm 0.95 (dd, J=23.61, 11.94 Hz, 1 H) 1.01 (d, J=6.64 Hz, 3 H) 1.16 (t, J=7.29 Hz, 3 H) 1.75 (br. s., 4 H) 2.00 - 2.15 (m, 1 H) 2.21 (d, J=12.51 Hz, 1 H) 2.33 - 2.56 (m, 3 H) 2.98 (tt, J=10.79, 3.99 Hz, 1 H) 3.22 - 3.47 (m, 6 H) 3.59 (dt, J=11.24, 1.95 Hz, 1 H) 7.02 - 7.09 (m, 1 H) 7.13 (m, 1 H) 7.51 (dd, J=8.55, 4.23 Hz, 1 H) 8.01 (d, J=7.97 Hz, 1 H) 8.37 (dd, J=8.56, 1.70 Hz, 1 H) 9.06 (dd, J=4.22, 1.70 Hz, 1 H) | LCMS (ESI+) calcd. for C20H25N5O (M+H+): 352.21, found: 352 |
| ER-899550 | [structure] C20H25N5O | 351.5 | 0.0110 | > 10.0 | 2-(((3R,5S)-1-(8-cyanoquinolin-5-yl)-5-methylpiperidin-3-yl)amino)-N,N-dimethylacetamide | 1H NMR (400 MHz, CHLOROFORM-d) d ppm 0.96 - 1.07 (m, 4 H) 1.07 - 1.20 (m, 1 H) 2.09 (s, 2 H) 2.23 (d, J=12.51 Hz, 1 H) 2.44 (t, J=11.44 Hz, 1 H) 2.62 - 2.72 (m, 1 H) 2.97 (m, J=9.46 Hz, 5 H) 3.00 - 3.09 (m, 2 H) 3.13 (d, J=4.81 Hz, 1 H) 3.40 (d, J=8.09 Hz, 1 H) 3.55 (d, J=3.24 Hz, 2 H) 3.58 - 3.67 (m, 1 H) 7.09 (d, J=8.01 Hz, 1 H) 7.50 (dd, J=8.49, 4.29 Hz, 1 H) 8.03 (d, J=7.93 Hz, 1 H) 8.40 (dd, J=8.54, 1.49 Hz, 1 H) 9.07 (dd, J=4.06, 1.51 Hz, 1 H) | LCMS (ESI+) calcd. for C20H25N5O (M+H+): 352.21, found: 352.1 |

FIG. 3X

| ID | Structure | Formula | MW | IC50 | >10 | Name | NMR | MS |
|---|---|---|---|---|---|---|---|---|
| ER-899551 | (furan structure) | C20H21N5O | 347.4 | 0.0430 | >10.0 | 5-(((3S,5R)-3-methyl-5-(((oxazol-2-yl)methyl)amino)piperidin-1-yl)quinoline-8-carbonitrile | 1H NMR (400 MHz, METHANOL-d4) d ppm 0.95 - 1.13 (m, 4 H) 1.93 - 2.14 (m, 2 H) 2.14 - 2.26 (m, 2 H) 2.49 (dt, 2 H) 2.91 - 3.14 (m, 1 H) 3.41 (dt, 1 H) 3.55 - 3.76 (m, 1 H) 4.01 (s, 1 H) 7.07 - 7.25 (m, 2 H) 7.62 (dd, 1 H) 7.91 (d, 1 H) 8.10 (d, 1 H) 8.49 (dd, 1 H) 8.95 (dd, 1 H) | LCMS (ESI+) calcd. for C20H21N5O (M+H+): 348.18, found: 348.3 |
| ER-899552 | (imidazole structure) | C21H24N6 | 360.5 | 0.2070 | 1.969 | 5-(((3S,5R)-3-methyl-5-(((1-methyl-1H-imidazol-4-yl)methyl)amino)piperidin-1-yl)quinoline-8-carbonitrile | 1H NMR (400 MHz, METHANOL-d4) d ppm 0.95 - 1.13 (m, 4 H) 1.93 - 2.14 (m, 2 H) 2.14 - 2.26 (m, 2 H) 2.49 (dt, 3 H) 2.91 - 3.14 (m, 2 H) 3.41 (dt, 2 H) 3.55 - 3.76 (m, 1 H) 4.01 (s, 1 H) 7.07 - 7.25 (m, 2 H) 7.62 (dd, 1 H) 7.91 (d, 1 H) 8.10 (d, 1 H) 8.49 (dd, 1 H) 8.95 (dd, 1 H) | LCMS (ESI+) calcd. for C21H24N6 (M+H+): 361.21, found: 361.34 |
| ER-899563 | (trifluoromethylpyridine structure) | C23H22F3N5 | 425.5 | 0.0550 | >10.0 | 5-(((3S,5R)-3-methyl-5-(((6-(trifluoromethyl)pyridin-3-yl)methyl)amino)piperidin-1-yl)quinoline-8-carbonitrile | 1H NMR (400 MHz, METHANOL-d4) d ppm 0.95 - 1.13 (m, 3 H) 1.93 - 2.14 (m, 2 H) 2.14 - 2.26 (m, 2 H) 2.49 (dt, 3 H) 2.91 - 3.14 (m, 1 H) 3.41 (dt, 1 H) 3.55 - 3.76 (m, 1 H) 4.01 (s, 1 H) 7.07 - 7.25 (m, 2 H) 7.62 (dd, 1 H) 7.91 (d, 1 H) 8.10 (d, 1 H) 8.49 (dd, 1 H) 8.95 (dd, 1 H) | LCMS (ESI+) calcd. for C23H22F3N5 (M+H+): 426.19, found: 426.34 |
| ER-899564 | (pyrazole structure) | C20H22N6 | 346.4 | 0.0930 | >10.0 | 5-((3R,5S)-3-(((1H-pyrazol-5-yl)methyl)amino)-5-methylpiperidin-1-yl)quinoline-8-carbonitrile | 1H NMR (400 MHz, METHANOL-d4) d ppm 0.97 (d, 4 H) 1.26 (q, 1 H) 1.81 - 1.99 (m, 1 H) 2.09 (d, 1 H) 2.41 (t, 1 H) 2.61 - 2.80 (m, 1 H) 3.12 (d, 1 H) 3.53 (d, 1 H) 3.79 (br. s., 4 H) 6.28 (br. s., 2 H) 7.08 (d, 1 H) 7.55 (dd, 1 H) 8.02 (d, 1 H) 8.26 (d, 1 H) 8.89 (dd, 1 H) | LCMS (ESI+) calcd. for C20H22N6 (M+H+): 347.19, found: 347.31 |
| ER-899565 | (dimethylpyrazole structure) | C22H26N6 | 374.5 | 0.0930 | >10.0 | 5-((3R,5S)-3-(((1,4-dimethyl-1H-pyrazol-3-yl)methyl)amino)-5-methylpiperidin-1-yl)quinoline-8-carbonitrile | 1H NMR (400 MHz, METHANOL-d4) d ppm 0.99 (d, 3 H) 1.27 - 1.43 (m, 1 H) 1.74 - 2.01 (m, 2 H) 2.01 - 2.10 (m, 1 H) 2.13 (s, 1 H) 2.43 (t, 1 H) 2.79 - 2.93 (m, 1 H) 3.02 - 3.17 (m, 1 H) 3.27 (dt, 1 H) 3.33 (d, 2 H) 3.39 - 3.56 (m, 3 H) 3.65 - 3.79 (m, 3 H) 7.12 (d, 1 H) 7.26 (s, 1 H) 7.53 (dd, 1 H) 8.04 (d, 1 H) 8.26 (dd, 1 H) 8.90 (dd, 1 H) | LCMS (ESI+) calcd. for C22H26N6 (M+H+): 375.23, found: 375.34 |
| ER-899566 | (dimethylisoxazole structure) | C22H25N5O | 375.5 | 0.0650 | 4.486 | 5-((3S,5S)-3-(((3,5-dimethylisoxazol-4-yl)methyl)amino)-5-methylpiperidin-1-yl)quinoline-8-carbonitrile | 1H NMR (400 MHz, METHANOL-d4) d ppm 0.91 - 1.10 (m, 4 H) 2.02 - 2.16 (m, 2 H) 2.16 - 2.25 (m, 3 H) 2.28 (br. s., 1 H) 2.33 (s, 3 H) 2.36 - 2.59 (m, 3 H) 2.95 - 3.10 (m, 1 H) 3.39 (d, 1 H) 3.59 (d, 1 H) 3.60 - 3.72 (m, 1 H) 7.17 (d, 1 H) 7.57 (dd, 1 H) 8.05 (d, 1 H) 8.47 (dd, 1 H) 8.90 (dd, 1 H) | LCMS (ESI+) calcd. for C22H25N5O (M+H+): 376.21, found: 376.29 |

FIG. 3Y

| ID | Structure | MW | Value | Value2 | Name | 1H NMR | LCMS |
|---|---|---|---|---|---|---|---|
| ER-899577 | C20H23N5O | 349.4 | 0.0170 | > 10.0 | 5-(((3S,5R)-3-methyl-5-((2-oxopyrrolidin-3-yl)amino)piperidin-1-yl)quinoline-8-carbonitrile | 1H NMR (400 MHz, METHANOL-d4) d ppm 0.97 - 1.17 (m, 6 H) 2.03 - 2.29 (m, 3 H) 2.47 (q, 3 H) 3.40 (d, 1 H) 3.54 - 3.76 (m, 1 H) 3.86 - 4.02 (m, 3 H) 4.70 (s, 1 H) 7.17 (d, 1 H) 7.64 (dd, 1 H) 8.06 (d, 1 H) 8.56 (dd, 1 H) 8.92 (dd, 1 H) | LCMS (ESI+) calcd. for C20H23N5O (M+H+): 350.19; found: 350.32 |
| ER-899602 | C20H26N4O2S | 386.5 | 0.3810 | 5.5 | 5-(((3S,5R)-3-methyl-5-((3-(methylsulfonyl)propyl)amino)piperidin-1-yl)quinoline-8-carbonitrile | 1H NMR (400 MHz, METHANOL-d4) d ppm 0.93 - 1.21 (m, 6 H) 1.96 - 2.17 (m, 3 H) 2.23 (d, 1 H) 2.49 (dt, 2 H) 2.71 - 2.90 (m, 1 H) 2.97 (s, 3 H) 3.08 (ddd, 1 H) 3.16 - 3.28 (m, 1 H) 3.35 (s, 1 H) 3.44 (d, 1 H) 3.69 (d, 1 H) 7.23 (d, 1 H) 7.63 (dd, 1 H) 8.12 (d, 1 H) 8.55 (dd, 1 H) 8.96 (dd, 1 H) | LCMS (ESI+) calcd. for C20H26N4O2S (M+H+): 387.18; found: 387.18 |
| ER-899604 | C22H25N5 | 359.5 | 0.0112 | > 10.0 | 5-(((3R,5S)-3-(2-cyanocyclopentyl)amino)-5-methylpiperidin-1-yl)quinoline-8-carbonitrile | 1H NMR (400 MHz, METHANOL-d4) d ppm 1.01 - 1.23 (m, 7 H) 1.80 - 1.90 (m, 4 H) 2.05 - 2.21 (m, 1 H) 2.26 (d, 1 H) 2.43 - 2.59 (m, 3 H) 3.36 - 3.48 (m, 2 H) 3.66 - 3.81 (m, 1 H) 6.46 (d, 1 H) 7.13 - 7.38 (m, 1 H) 7.63 (dd, 1 H) 8.00 - 8.24 (m, 1 H) 8.74 (dd, 1 H) 8.96 (dd, 1 H) | LCMS (ESI+) calcd. for C22H25N5 (M+H+): 360.21; found: 360.21 |
| ER-899607 | C23H25N5 | 371.5 | 0.14489 | > 10.0 | 5-(((3S,5R)-3-methyl-5-((1-(pyridin-2-yl)ethyl)amino)piperidin-1-yl)quinoline-8-carbonitrile | 1H NMR (400 MHz, METHANOL-d4) d ppm 0.95 - 1.15 (m, 3 H) 1.31 (q, 1 H) 1.53 - 1.71 (m, 3 H) 2.00 - 2.11 (m, 1 H) 2.31 (d, 1 H) 2.43 (d, 1 H) 2.51 (td, 1 H) 2.61 - 2.73 (m, 3 H) 2.75 - 2.92 (m, 1 H) 3.34 - 3.50 (m, 1 H) 3.72 (d, 1 H) 4.79 (q, 1 H) 7.24 (dd, 1 H) 7.39 - 7.52 (m, 1 H) 7.52 - 7.58 (m, 1 H) 7.61 (dd, 1 H) 7.84 - 7.98 (m, 1 H) 8.12 (d, 1 H) 8.31 - 8.43 (m, 1 H) 8.92 - 9.01 (m, 1 H) | LCMS (ESI+) calcd. for C23H25N5 (M+H+): 372.21; found: 372.35 |
| ER-899621 | C21H26N4O | 350.5 | 0.0806 | > 10.0 | 5-(((3S,5R)-3-methyl-5-((tetrahydro-2H-pyran-3-yl)amino)piperidin-1-yl)quinoline-8-carbonitrile | 1H NMR (400 MHz, METHANOL-d4) d ppm 1.07 (d, 4 H) 1.19 - 1.39 (m, 1 H) 1.59 - 1.78 (m, 1 H) 1.78 - 1.97 (m, 2 H) 2.09 - 2.31 (m, 3 H) 2.31 - 2.44 (m, 1 H) 2.50 (t,1 H) 2.85 - 2.96 (m, 1 H) 3.35 - 3.58 (m, 2 H) 3.60 - 3.90 (m, 3 H) 3.95 - 4.14 (m, 1 H) 7.26 (d, 1 H) 7.63 (dd, 1 H) 8.08 (d, 1 H) 8.38 (br. s., 1 H) 8.55 (dd, 1 H) 8.94 (dt, 1 H) | LCMS (ESI+) calcd. for C21H26N4O (M+H+): 351.21; found: 351.46 |

FIG. 3Z

| ID | Structure | Formula | MW | IC50 | Ratio | Name | NMR | MS |
|---|---|---|---|---|---|---|---|---|
| ER-899630 | | C22H28N4O | 364.5 | 0.0182 | 5.073 | 5-((3R,5S)-3-(((1s,4S)-4-hydroxycyclohexyl)amino)-5-methylpiperidin-1-yl)quinoline-8-carbonitrile | 1H NMR (400 MHz, METHANOL-d4) d ppm 0.87 - 1.06 (m, 6 H) 1.06 - 1.36 (m, 4 H) 1.83 - 2.03 (m, 3 H) 2.08 (td, 1 H) 2.16 (d, 1 H) 2.26 - 2.52 (m, 3 H) 2.52 - 2.71 (m, 1 H) 3.06 - 3.23 (m, 1 H) 3.39 (dd, 1 H) 3.44 - 3.55 (m, 1 H) 3.55 - 3.67 (m,1 H) 7.18 (d, 1 H) 7.52 - 7.76 (m, 1 H) 8.03 - 8.23 (m, 1 H) 8.51 (dd, 1 H) 8.84 - 9.04 (m, 1 H) | LCMS (ESI+) calcd. for C22H28N4O (M+H+): 365.23; found: 365.23 |
| ER-899631 | | C22H28N4O | 364.5 | 0.0305 | 3.144 | 5-((3R,5S)-3-(((1r,4R)-4-hydroxycyclohexyl)amino)-5-methylpiperidin-1-yl)quinoline-8-carbonitrile | 1H NMR (400 MHz, METHANOL-d4) d ppm 0.85 - 1.07 (m, 5 H) 1.48 - 1.78 (m, 8H) 1.95 - 2.10 (m, 1 H) 2.15 (d, 1 H) 2.32 - 2.53 (m, 3 H) 2.68 (dd, 1 H) 3.11 - 3.24 (m, 1 H) 3.34 - 3.45 (m, 1 H) 3.48 - 3.75 (m, 1 H) 3.75 - 3.94 (m, 1 H) 7.15 (d, 1 H) 7.56 (dd, 1 H) 8.05 (d, 1 H) 8.49 (dd, 1 H) 8.90 (dd, 1 H) | LCMS (ESI+) calcd. for C22H28N4O (M+H+): 365.23; found: 365.23 |
| ER-899632 | | C22H26N4O | 362.5 | 0.0461 | 4.128 | 5-((3S,5R)-3-methyl-5-((4-oxocyclohexyl)amino)piperidin-1-yl)quinoline-8-carbonitrile | 1H NMR (400 MHz, METHANOL-d4) d ppm 1.01 - 1.15 (m, 4 H) 1.27 (q, 1 H) 1.96 - 2.14 (m, 1 H) 2.34 - 2.63 (m, 7 H) 2.63 - 2.70 (m, 2 H) 2.74 - 2.96 (m, 1 H) 3.33 - 3.38 (m, 1 H) 3.43 - 3.60 (m, 1 H) 3.70 - 3.91 (m, 2 H) 7.22 - 7.44 (m, 1 H) 7.66 (dd, 1H) 8.16 (d, 1 H) 8.34 (s, 1 H) 8.44 - 8.59 (m, 1 H) 8.99 (dt, 1 H) | LCMS (ESI+) calcd. for C22H26N4O (M+H+): 363.21; found: 363.21 |
| ER-899633 | | C21H26N4O2S | 398.5 | 0.2750 | >10.0 | 5-((3R,5S)-3-((1,1-dioxidotetrahydro-2H-thiopyran-4-yl)amino)-5-methylpiperidin-1-yl)quinoline-8-carbonitrile | 1H NMR (400 MHz, METHANOL-d4) d ppm 0.98 - 1.06 (m, 3 H) 1.84 - 2.09 (m, 2 H) 2.16 - 2.38 (m, 4 H) 2.38 - 2.61 (m, 3 H) 2.99 - 3.26 (m, 4 H) 3.35 (s, 1 H) 3.44 (d, 1 H) 3.66 (dd, 1 H) 7.22 (d, 1 H) 7.63 (dd, 1 H) 8.11 (d, 1 H) 8.55 (dd, 1 H) 8.96 (dd, 1 H) | LCMS (ESI+) calcd. for C21H26N4O2S (M+H+):399.18; found: 399.18 |
| ER-899634 | | C24H27N5 | 385.5 | 0.1280 | 4.563 | 5-((3S,5R)-3-methyl-5-((1-(6-methylpyridin-2-yl)ethyl)amino)piperidin-1-yl)quinoline-8-carbonitrile | 1H NMR (400 MHz, METHANOL-d4) d ppm 0.90 - 1.15 (m, 4 H) 1.23 - 1.46 (m, 3 H) 1.84 - 2.11 (m, 2 H) 2.28 (d, 1 H) 2.36 - 2.59 (m, 3 H) 2.76 - 2.92 (m, 1 H) 3.33 - 3.46 (m, 3 H) 4.11 (q, 1 H) 7.03 - 7.24 (m, 3 H) 7.24 - 7.37 (m, 1 H) 7.47 - 7.57 (m, 1 H) 7.67 (t, 1 H) 8.00 - 8.14 (m, 1 H) 8.30 (dd, 1 H) 8.89 - 8.99 (m, 1 H) | LCMS (ESI+) calcd. for C24H27N5 (M+H+): 386.23; found: 386.23 |

FIG. 3AA

| ID | Structure | Formula | MW | Value | Value2 | Name | NMR | LCMS |
|---|---|---|---|---|---|---|---|---|
| ER-899669-HCl | (structure with sulfonamide, NH2, piperidine, quinoline-CN, HCl) | C18H24ClN5O2S | 409.9 | 0.1350 | 1.493 | 2-amino-N-((3R,5S)-1-(8-cyanoquinolin-5-yl)-5-methylpiperidin-3-yl)ethanesulfonamide hydrochloride | 1H NMR (400 MHz, METHANOL-d4) d ppm 1.03 (d, J=5.62 Hz, 3 H) 1.17 (q, J=11.75 Hz, 1 H) 2.03 - 2.30 (m, 2 H) 2.48 (t, J=11.43 Hz, 1 H) 2.64 (t, J=12.18 Hz, 1 H) 3.02 - 3.15 (m, 2 H) 3.19 - 3.28 (m, 2 H) 3.35 - 3.49 (m, 1 H) 3.67 - 3.84 (m, 2 H) 7.22 (d, J=8.12 Hz, 1 H) 7.63 (dd, J=8.55, 4.27 Hz, 1 H) 8.12 (d, J=8.12 Hz, 1 H) 8.57 (dd, J=8.55, 1.71 Hz, 1 H) 8.97 (dd, J=4.27, 1.71 Hz, 1 H) | LCMS (ESI+) calcd. for C18H23N5O2S (M+H+): 374.13; found: 374.25 |
| ER-899671-HCl | (structure with N-methyl) | C20H28ClN5O2S | 438.0 | 0.2490 | 5.37 | N-((3R,5S)-1-(8-cyanoquinolin-5-yl)-5-methylpiperidin-3-yl)-2-(dimethylamino)ethanesulfonamide hydrochloride | | |
| ER-899672-HCl | (structure) | C21H30ClN5O2S | 452.0 | 0.0276 | 3.139 | N-((3R,5S)-1-(8-cyanoquinolin-3-yl)-5-methylpiperidin-3-yl)-3-(dimethylamino)propane-1-sulfonamide hydrochloride | 1H NMR (400 MHz, METHANOL-d4) d ppm 1.03 (d, J=6.41 Hz, 3 H) 1.17 (q, J=11.68 Hz, 1 H) 1.89 - 2.05 (m, 2 H) 2.06 - 2.22 (m, 2 H) 2.26 (s, 6 H) 2.39 - 2.53 (m, 3 H) 2.62 (t, J=12.18 Hz, 1 H) 3.07 - 3.20 (m, 2 H) 3.37 - 3.47 (m, 1 H) 3.67 - 3.81 (m, 2 H) 7.22 (d, J=7.90 Hz, 1 H) 7.62 (dd, J=8.55, 4.27 Hz, 1 H) 8.12 (d, J=8.12 Hz, 1 H) 8.57 (dd, J=8.76, 1.71 Hz, 1 H) 8.96 (dd, J=4.27, 1.71 Hz, 1 H) | LCMS (ESI+) calcd. for C21H30ClN5O2S (M+H+): 416.18; found: 416.32 |
| ER-899715-14 | (structure with oxetane, acetate) | C22H28N4O3 | 396.5 | 0.4840 | > 10.0 | 5-((3S,5R)-3-methyl-5-(methyl(oxetan-3-yl)amino)piperidin-1-yl)quinoline-8-carbonitrile acetate | 1H NMR (CDCl3) d ppm 9.03 (dd, 1H), 8.33 (dd, 1H), 8.00 (d, 1H), 7.47 (dd, 1H), 7.03 (d, 1H), 4.94 (m, 2H), 4.64 (m, 2H), 4.02 (dd, 1H), 3.40 (m, 1H), 3.38 (s, 3H), 3.30 (m, 1H), 2.82 (m, 1H), 2.65 (dd, 1H), 2.35 (dd, 1H), 2.27 (s, 3H), 2.00 (m, 1H), 1.10 (q, 1H), 0.99 (d, 3H) | LCMS (ESI+) calcd. for C20H24N4O: 337.2, found 337.2 |
| ER-899823 | (structure with hydroxypropyl NH) | C19H24N4O | 396.5 | 0.1090 | 8.71 | 5-((5S)-3-((1-hydroxypropan-2-yl)amino)-5-methylpiperidin-1-yl)quinoline-8-carbonitrile | mixture of 4 diastereomers 1H NMR (CDCl3) d ppm 9.04-8.88 9m, 1H), 8.69-8.35 (m, 1H), 8.00-7.88 9M, 1H), 7.50-7.34 (m, 1H), 7.06-6.82 (m, 1H), 3.62-2.80 (overlapping multiplets, 6H), 2.52-2.0 (overlapping multiplets, 3H), 1.23-0.90 (overlapping multiplets 8H) | LCMS (ESI+) calcd. for C19H24N4O (M+H+): 325.2, found 325.2 |

FIG. 3BB

SELECTIVELY SUBSTITUTED QUINOLINE COMPOUNDS

BACKGROUND

Field of the Disclosure

Embodiments of the disclosure relate to selectively substituted quinoline compounds and pharmaceutical agents comprising one or more of those compounds as active ingredient(s). More particularly, embodiments of the disclosure relate to those compounds that act as an antagonist or inhibitor for Toll-like receptors (TLR) 7 and 8, and their use in a pharmaceutical composition effective for treatment of systemic lupus erythematosus (SLE) and lupus nephritis.

Description of Related Art

Systemic lupus erythematosus (SLE) and lupus nephritis are autoimmune diseases characterized by inflammation and tissue damage. For example, SLE may cause damage to the skin, liver, kidneys, joints, lungs, and central nervous system. SLE sufferers may experience general symptoms such as extreme fatigue, painful and swollen joints, unexplained fever, skin rash, and kidney dysfunction. Because organ involvement differs amongst patients, symptoms may vary. SLE is predominantly a disease of younger women, with peak onset between 15-40 years of age and an approximate 10-fold higher prevalence in women vs. men.

Current treatments for SLE typically involve immunomodulatory drugs such as belimumab, hydroxychloroquine, prednisone, and cyclophosphamide. All of these drugs may have dose-limiting side effects, and many patients still have poorly controlled disease.

BRIEF SUMMARY OF THE DISCLOSURE

Embodiments of the disclosure provide compounds and methods of use for preventing or treating diseases or conditions characterized by Toll-like receptor 7 or 8 activation in patients. One embodiment features a compound of formula (I):

A further embodiment provides a compound of Formula (I):

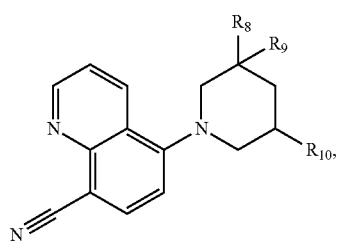

(I)

wherein
$R_8$ is H or methyl;
$R_9$ is —H, methyl, or hydroxyl;
$R_{10}$ is —H, methyl, hydroxyl, or $NR_{11}R_{12}$; and
wherein $R_{11}$ and $R_{12}$ are independently selected, and wherein
$R_{11}$ is —H, methyl, or —CH$_2$—C(O)CH$_2$CH$_3$; and
$R_{12}$ is
—H, oxopyrrolidinyl, dioxidothiopyranyl, isopropylsulfonyl, tetrahydropyranyl, oxetanyl, tetrahydropyranyl, hydroxyl, dimethylaminethanesulfonyl, aminethanesulfonyl, dimethylaminpropanesulfonyl, $C_1$-$C_6$ alkyl that is linear, branched, or cyclic, optionally substituted with methoxy, —F, ≡N, methyl oxetanyl, ethoxy, oxo-, methyl imidazolyl, methylthio piperazinyl optionally substituted with methyl or —CF$_3$,
acetamidyl optionally substituted with methyl or ethyl,
oxazolyl optionally substituted with methyl,
pyrazolyl optionally substituted with methyl, cyano, or hydroxyl,
—C(O)R$_{13}$, wherein
R$_{13}$ is
$C_1$ to $C_7$ alkyl that is cyclic, branched, or linear, optionally substituted with
$NR_{15}R_{14}$, wherein $R_{15}$ and $R_{14}$ are independently selected from methyl and —H;
methoxy, hydroxyl, methylthio, ethylthio, methylsulfonyl, thiazolidinyl, pyridinyl, pyrazolopyridinyl, methyl amino, thiazolyl, —F, morpholinyl, methylisoxazolyl, methyl oxetanyl, aminooxetanyl,
phenyl optionally substituted with hydroxyl, —C(O)NH$_2$;
a five membered cycloalkyl, saturated or unsaturated, in which 1 or 2 carbon atoms are replaced by nitrogen atoms, wherein the cycloamine or cyclodiamine is optionally substituted with hydroxyl or methyl.

In a further embodiment the compound is 5-((3R,5S)-3-amino-5-methylpiperidin-1-yl)quinoline-8-carbonitrile.

In a further embodiment the compound or pharmaceutically effective salt thereof of a compound of the preceding paragraphs has an IC50 less than or equal to 20 nM against human TLR7 receptors expressed in a HEK-293 cell line. In a further embodiment the compound or pharmaceutically effective salt thereof of the preceding paragraph of this disclosure has an IC50 less than or equal to 100 nM against human TLR7 receptors expressed in a HEK-293 cell line. In a further embodiment the IC50 against human TLR7 receptors expressed in a HEK-293 cell line is measured by (1) plating cells of the HEK-293 cell line stably expressing TLR7 in Dulbecco's modified Eagle's medium containing 10% fetal bovine serum at a density of 2.22×105 cells/ml into a 384-well plate and incubating for 2 days at 37° C., 5% CO$_2$; (2) adding the compound or pharmaceutically acceptable salt thereof and incubating the cells for 30 minutes; (3) adding CL097 (InvivoGen) at 3 ug/ml and incubating the cells for approximately 20 hours; and (4) quantifying NF-kappaB dependent reporter activation by measuring luminescence.

In further embodiments of the disclosure, compounds have an IC50 against human TLR7 receptors expressed in a HEK-293 cell line less than or equal to 200 nM, less than or equal to 180 nM, less than or equal to 160 nM, less than or equal to 140 nM, less than or equal to 120 nM, less than or equal to 100 nM, less than or equal to 80 nM, less than or equal to 60 nM, less than or equal to 40 nM, or less than or equal to 20 nM. In further embodiments of the disclosure, compounds have an IC50 against human TLR7 receptors expressed in a HEK-293 cell line from 10 nM to 30 nM, from 10 nM to 50 nM, from 10 nM to 100 nM, from 30 nM to 50 nM, from 30 nM to 100 nM, or from 50 nM to 100 nM. In further embodiments the IC50 against human TLR7 receptors expressed in a HEK-293 cell line is measured by (1) plating cells of the HEK-293 cell line stably expressing TLR7 in Dulbecco's modified Eagle's medium containing 10% fetal bovine serum at a density of 2.22×105 cells/ml into a 384-well plate and incubating for 2 days at 37° C., 5% CO$_2$; (2) adding the compound or pharmaceutically acceptable salt thereof and incubating the cells for 30 minutes; (3)

adding CL097 (InvivoGen) at 3 ug/ml and incubating the cells for approximately 20 hours; and (4) quantifying NF-kappaB dependent reporter activation by measuring luminescence.

Further embodiments provide methods for treatment of lupus, including but not limited to treatment of systemic lupus erythematosus, cutaneous lupus, neuropsychiatric lupus, fetal heart block, and antiphospholipid syndrome, including administering a pharmaceutically effective amount of a compound or pharmaceutically acceptable salt of the disclosure.

Further embodiments provide methods for antagonizing TLR7, including administering a pharmaceutically effective amount of a compound or pharmaceutically acceptable salt of the disclosure.

Further embodiments provide methods for antagonizing TLR8, including administering a pharmaceutically effective amount of a compound or pharmaceutically acceptable salt of the disclosure.

Further embodiments provide pharmaceutical compositions comprising at least one compound or pharmaceutically acceptable salt of the disclosure and at least one pharmaceutically acceptable carrier.

Further embodiments provide methods for treatment of systemic lupus erythematosus or lupus, including administering a pharmaceutically effective amount of a compound or pharmaceutically acceptable salt of the disclosure.

Further embodiments provide methods for antagonizing TLR7, including administering a pharmaceutically effective amount of a compound or pharmaceutically acceptable salt of the disclosure.

Further embodiments provide methods for antagonizing TLR8, including administering a pharmaceutically effective amount of a compound or pharmaceutically acceptable salt of the disclosure.

Further embodiments provide pharmaceutical compositions comprising at least one compound or pharmaceutically acceptable salt of the disclosure and at least one pharmaceutically acceptable carrier.

The term "optionally substituted," as used herein, means that the subject structure may include, but is not required to include, one or more substituents independently selected from lower alkyl, methoxy-, —OH, —NH$_2$, —CH$_2$—NH—CH$_2$, —OCH$_2$CH$_2$CH$_3$, or —OCH(CH$_3$)$_2$. If the optionally substituted moiety is cyclic, then the optional substitution may be a methyl bridge between two atoms in the ring.

The symbol "C(O)" as used herein refers to a carbonyl group having the formula C=O.

Unless otherwise specified, "a" and "an" as used in this disclosure, including the claims, mean "one or more."

As used herein, "lower alkyl" refers to straight, or, in the case of three- and four-carbon groups, straight, branched, or cyclic saturated hydrocarbons having between one and four carbon atoms.

As used herein, the term "attached through a nitrogen" when referring to a heterocyclic moiety including nitrogen, means that a point of attachment of the moiety to another structure is through a nitrogen that is part of the heterocycle.

As used herein, the term "TLR7/8" means "TLR7 and TLR8" or "TLR7 or TLR8" or "TLR7 and/or TLR8." The particular meaning can be understood by a person skilled in the art based upon the context in which "TLR7/8" appears.

Heterocyclic moieties recited herein include azetidinyl, pyrrolidinyl, piperidinyl, methylazetidinyl, pyrazolyl, piperazinyl, morpholinyl, thiazolyl, pyrrolopyrrolyl, imidazolidinyl, and isothiazolyl. Where a heterocyclic group is mentioned, unless otherwise indicated it will be understood that the heterocyclic atom(s) in the group may be at any position in the group. It will further be understood that imidazolyl, pyrazolyl, thiazolyl, and pyrrolyl may be unsaturated or partially unsaturated. An embodiment of the disclosure may include a pharmaceutical composition that includes one or more compounds of the disclosure with a pharmaceutically acceptable excipient. These pharmaceutical compositions may be used to treat or prevent a disease or condition characterized by TLR7/8 activation in a patient, typically a human patient, who has or is predisposed to have such a condition or disease. Examples of diseases or conditions characterized by TLR7/8 activation include systemic lupus erythematosus (SLE) and lupus nephritis.

As used herein, "effective amount" of a compound of an embodiment of the disclosure is effective amount of the above-identified compounds in an amount sufficient to treat or prevent SLE and lupus nephritis.

Embodiments presented herein may include asymmetric or chiral centers. Embodiments include the various stereoisomers and mixtures thereof. Individual stereoisomers of compounds of embodiments of the disclosure may be prepared synthetically from commercially available starting materials that contain asymmetric or chiral centers, or by preparation of mixtures of enantiomeric compounds followed by resolution of those compounds. Suitable methods of resolution include attachment of a racemic mixture of enantiomers, designated (+/−), to a chiral auxiliary, separation of the resulting diastereomer by chromatography or recrystallization and separation of the optically pure product from the auxiliary; or direct separation of the mixture of optical enantiomers on chiral chromatographic columns.

Embodiments of the disclosure also include a pharmaceutical composition including any compound of the disclosure as well as a pharmaceutically acceptable excipient. The pharmaceutical compositions can be used to treat or prevent SLE and lupus nephritis. Therefore, embodiments of the disclosure may also feature a method for treating or preventing SLE or lupus nephritis in a human patient having or predisposed to having lupus nephritis or SLE.

Embodiments of the disclosure include pharmaceutically acceptable salts of the compounds presented herein. The term "pharmaceutically acceptable salt" refers to those salts that are, within the scope of sound medical judgment, suitable for use in contact with the tissues of humans and animals without undue toxicity, irritation, or allergic response. Pharmaceutically acceptable salts are well known in the art. For example, S. M. Berge, et al., describes pharmaceutically acceptable salts in detail in *J. Pharmaceutical Sciences* 66:1-19, 1977. Salts can be prepared in situ during final isolation and purification of a compound or separately by reacting a free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, monomaleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, trifluoroacetate, undecanoate, valerate salts, and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The term "pharmaceutically acceptable ester," as used herein, represents esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl group typically has not more than 6 carbon atoms. Examples of particular esters include formates, acetates, propionates, butyates, acrylates, and ethylsuccinates.

In this application enantiomers are designated by the symbols "R" or "S" or are drawn by conventional means with a bolded line defining a substituent above the plane of the page in three-dimensional space and a hashed or dashed line defining a substituent beneath the plane of the printed page in three-dimensional space. If no stereochemical designation is made, then the structure definition includes both stereochemical options. If a structure or chemical name includes "REL" or "rel" then that structure is understood to show relative stereochemistry.

BRIEF SUMMARY OF THE FIGURES

FIG. 1A through FIG. 1D show results of treatment with ER-888840 (5-((3R,5S)-3-amino-5-methylpiperidin-1-yl) quinoline-8-carbonitrile) in the DBA/1 pristane model. Figure Legend: Female DBA/1 mice at 10 weeks of age were given an intraperitoneal injection of 0.5 ml pristane or PBS. At 18 weeks of age animals were bled for pre-dosing baseline auto-antibody titers. Once-a-day oral dosing with Vehicle (Veh; 0.5% methyl-cellulose) or 11 mg/kg, 33 mg/kg, or 100 mg/kg of ER-888840 was begun at 18 weeks of age, 8 weeks after pristane injection and continued for 12 weeks of treatment. At the end of the experiment plasma samples were taken and anti-dsDNA and anti-histone (FIG. 1A) and anti-Sm/RNP and anti-RiboP (FIG. 1B) titers were determined by ELISA. (FIG. 1C) The expression of IFN-regulated genes in whole blood was measured by a qPCR panel after 8 weeks of treatment. The genes upregulated by pristane treatment, and modulated by compound treatment in pristane treated mice are listed. (FIG. 1D) The interferon scores of individual mice were calculated (see Pharmacology Materials and Methods section for details regarding IFN score calculation) and groups compared using the Mann-Whitney t test.

(FIG. 2E). The expression of IFN-regulated genes in whole blood was measured by a qPCR panel after 12 weeks of treatment, and an IFN gene signature score was calculated (see Pharmacology Materials and Methods section for details regarding IFN score calculation). The table shows the full list of 18 genes significantly upregulated by pristane treatment vs. PBS controls. The interferon scores for individual animals in each treatment group are plotted and compared using the Mann-Whitney test.

FIG. 3A through 3BB, which includes multiple pages, shows structures and corresponding chemical names according to various embodiments presented herein. "ER-Number" is a reference number assigned to each compound. Where available, activity against a HEK cell line stably expressing human TLR7, activity against a HEK cell line stably expressing human TLR9, 1H NMR data, and mass spectrometry data are also included.

DETAILED DESCRIPTION OF THE DISCLOSURE

I. TLRs and Lupus

Figure 1A:
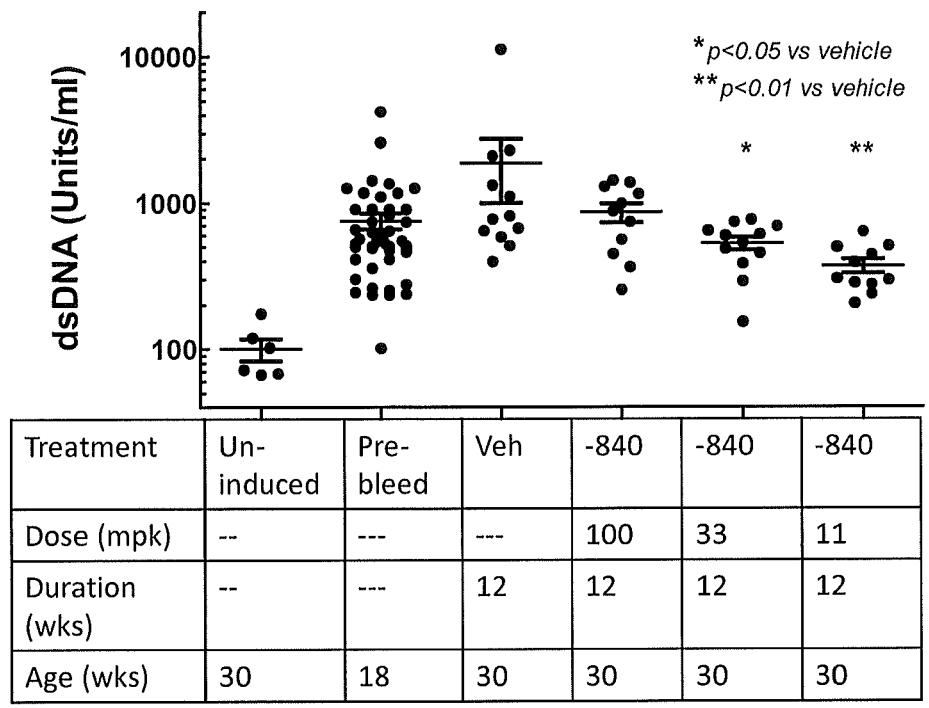
Figure 1A:
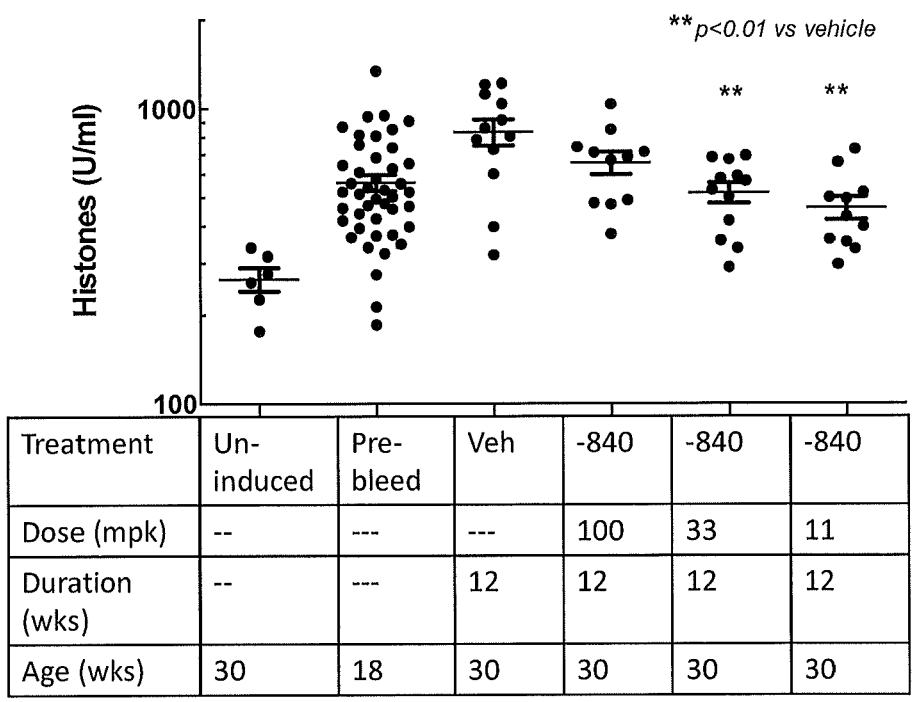
Figure 1B:
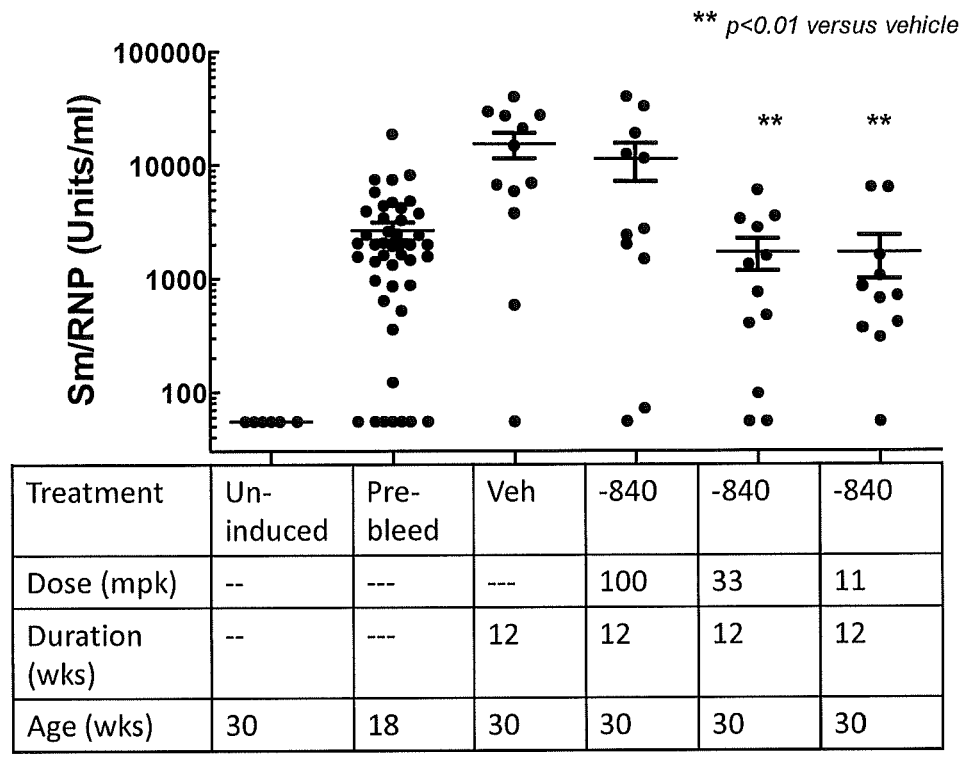
Figure 1B:
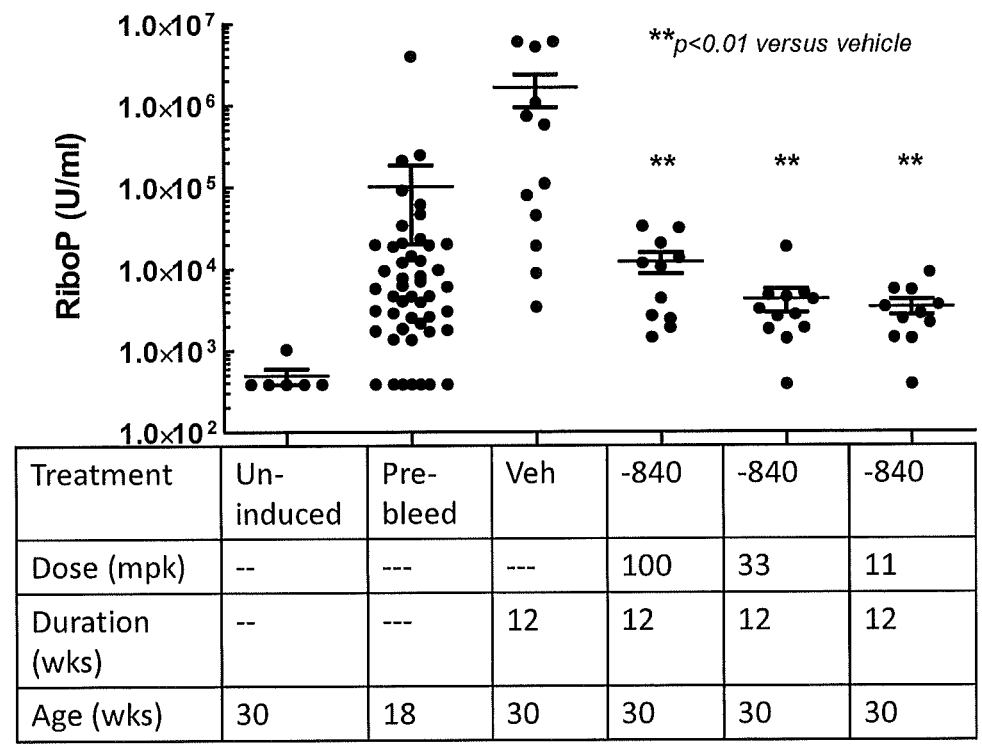
Figure 1D:
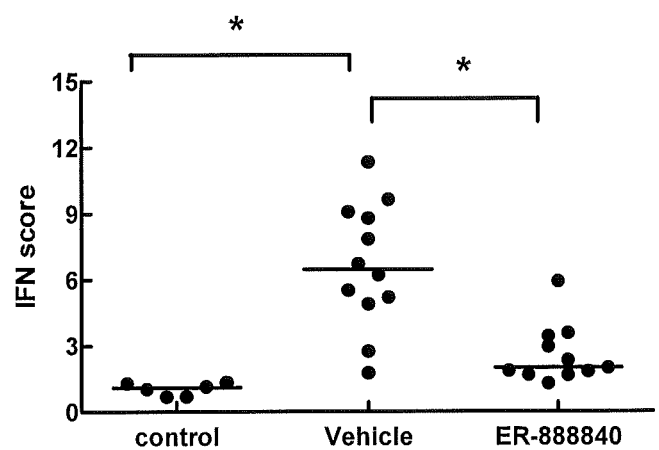
Figure 2A:
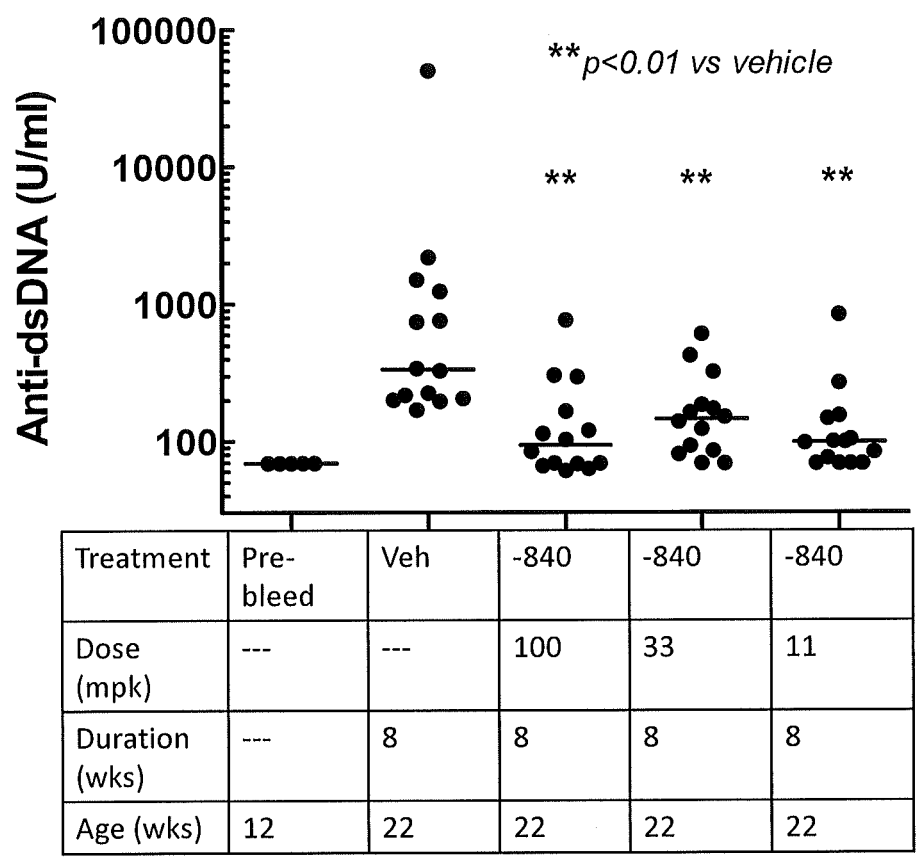
FIG. 2A through 2E show results of treatment with ER-888840 in the DBA/1 pristane model. Figure Legend: Female DBA/1 mice at 10 weeks of age were given an intraperitoneal injection of 0.5 ml pristane or PBS. At 12 weeks of age animals were bled for baseline auto-antibody titers. Once-a-day oral dosing with Vehicle (Veh; 0.5% methyl-cellulose) or 33 mg/kg, 100 mg/kg, or 300 mg/kg of ER-888840 was begun at 14 weeks of age, 4 weeks after pristane injection and continued for 8 weeks of treatment. At the end of the experiment plasma was taken and anti-dsDNA (FIG. 2A), anti-RiboP (FIG. 2B), anti-histone (FIG. 2C) and anti-Sm/RNP (FIG. 2D) titers were determined by ELISA.
Figure 2B:
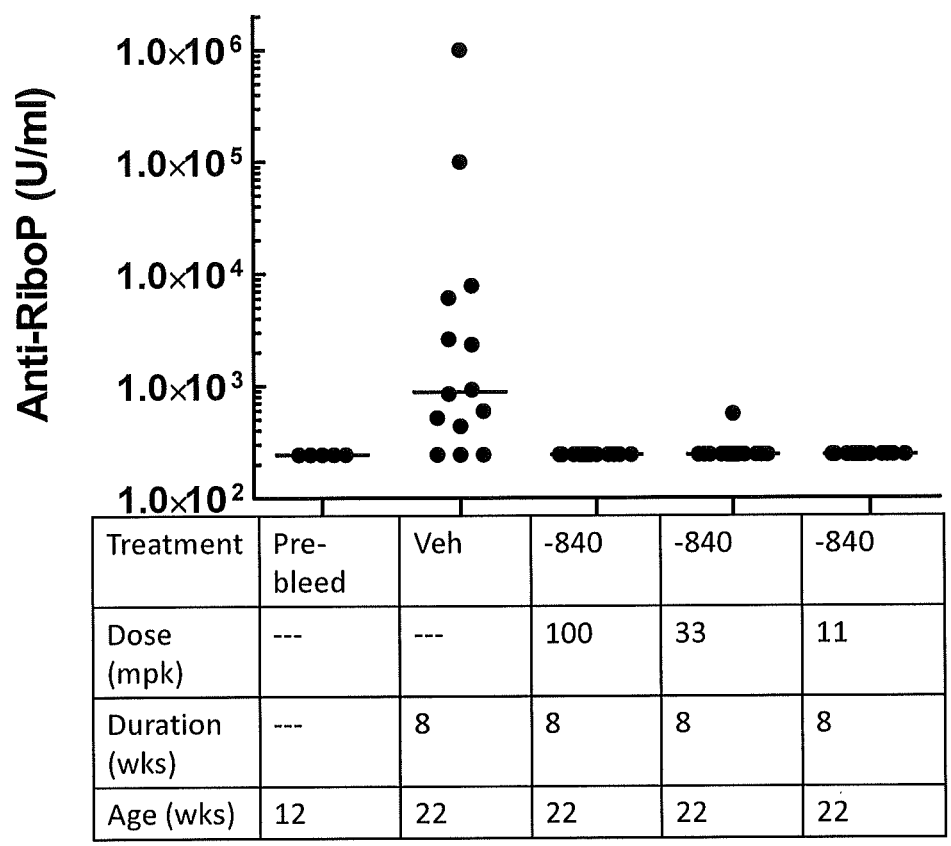
Figure 2C:
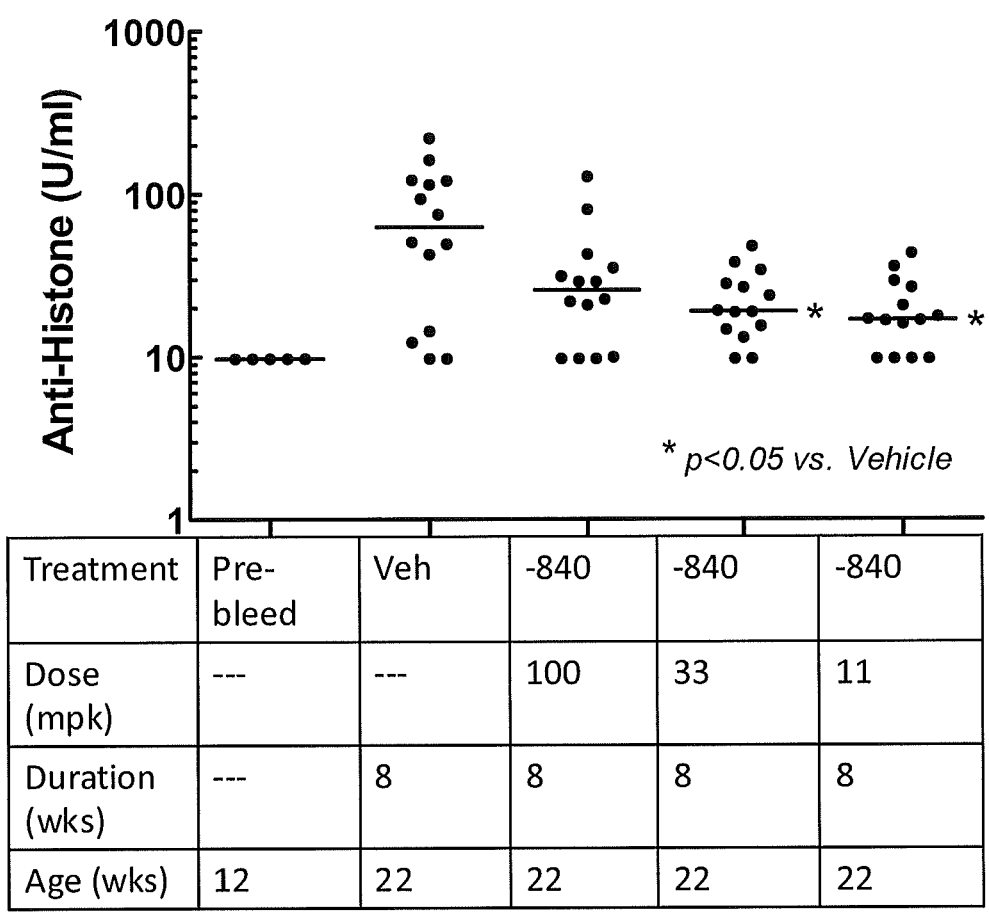
Figure 2D:
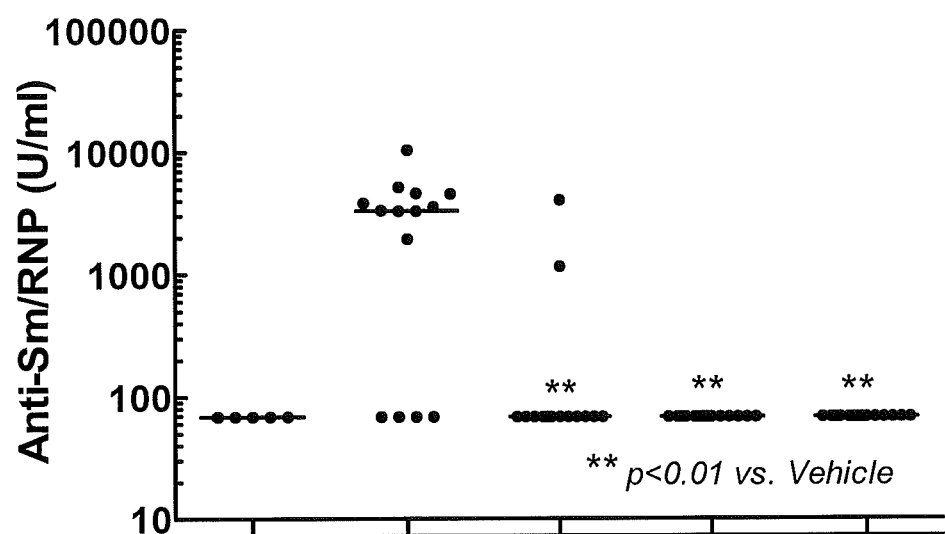
Figure 2E:
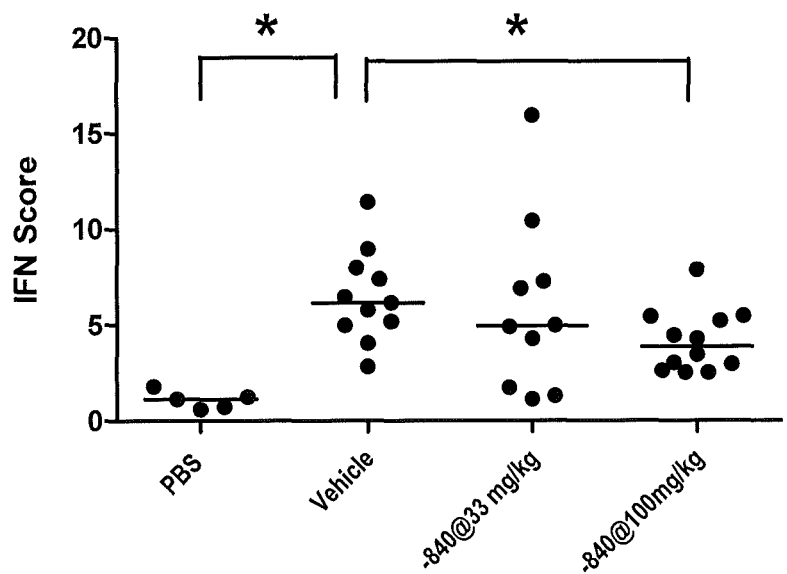

In addition to their role as innate immune receptors capable of detecting exogenous ("non-self") pathogen-associated molecular patterns (PAMPs—i.e., bacterial LPS detection by TLR4), mammalian Toll-like receptors (TLRs) are also capable of recognizing endogenous stimuli (DAMPs) released following host tissue damage or stress. Kono, H. and K. L. Rock, *How dying cells alert the immune system to danger.* Nat Rev Immunol, 2008. 8(4): p. 279-89. In the last decade an appreciation for the link between TLR activation by endogenous ("self") danger-associated molecular patterns (DAMPs) and the etiology of autoimmune disorders has emerged. Specifically, TLR7 can be activated by single-stranded RNA (ssRNA) derived from both mammalian and viral sources, whereas TLR9 can be activated by DNA derived from mammalian, viral, and bacterial sources.

Lupus is characterized by auto-antibodies reactive against double-stranded DNA (dsDNA) itself and associated proteins (histones) as well as against a broad array of RNA-associated proteins such as Ro, La, Smith (Sm), and U1 snRNP. Kirou, K. A., et al., *Activation of the interferon-alpha pathway identifies a subgroup of systemic lupus erythematosus patients with distinct serologic features and active disease.* Arthritis Rheum, 2005. 52(5): p. 1491-503. A second common hallmark of lupus, which was shown to correlate directly with disease severity, is dysregulated expression of type-1 interferons (IFNs), in particular IFNα, and the corresponding elevation of a large panel of IFNalpha-regulated genes in lupus patients' PBMC (the so called "type-1 IFN gene signature"). Kirou, K. A., et al., supra. A major source of IFN in the blood is a specialized immunocyte called a plasmacytoid dendritic cell (pDC), which constitutively expresses both TLR7 and TLR9.

A causal relationship between these two disease characteristics, auto-antibodies and IFN levels, was postulated when a number of research groups collectively demonstrated that antibody complexes isolated from lupus patients but not from healthy donors are capable of driving IFN production by pDC in a TLR7/9- and RNA/DNA-dependent manner. Means, T. K., et al., *Human lupus autoantibody-DNA complexes activate DCs through cooperation of CD32 and TLR9.* J Clin Invest, 2005. 115(2): p. 407-17; Vollmer, J., et al., *Immune stimulation mediated by autoantigen binding sites within small nuclear RNAs involves Toll-like receptors 7 and 8.* J Exp Med, 2005. 202(11): p. 1575-85; Savarese, E., et al., *U1 small nuclear ribonucleoprotein immune complexes induce type I interferon in plasmacytoid dendritic cells through TLR7.* Blood, 2006. 107(8): p. 3229-34. Moreover, IFN stimulates increased TLR7/9 expression on B-cells, thereby enhancing TLR/BCR (B-cell receptor) activation of auto-reactive B-cells to differentiate to antibody-producing plasma cells. Banchereau, J. and V. Pascual, *Type I interferon in systemic lupus erythematosus and other autoimmune diseases*. Immunity, 2006. 25(3): p. 383-92; In this fashion, levels of auto-antibody complexes containing nucleic acid TLR7/9 ligands drive the pro-inflammatory cycle and lupus disease progression. We believe it is likely that pharmacological antagonism of TLR7/8 will offer therapeutic benefit to lupus patients by disrupting this pro-inflammatory cycle, decreasing IFN levels, and dampening the autoimmune disease process mediated by pDC and B-cells.

Several other lines of evidence suggest a role for TLR7 in human lupus etiology and support the notion that TLR receptors are valid targets for disease intervention. Specific polymorphisms in the 3' UTR of TLR7 have been identified and shown to correlate with both elevated TLR7 expression and enhanced IFN gene signature. Shen, N., et al., *Sex-specific association of X-linked Toll-like receptor 7 (TLR7) with male systemic lupus erythematosus*. Proc Natl Acad Sci USA, 2010. 107(36): p. 15838-43. Deng, Y. et al., *MicroRNA-3148 modulates allelic expression of toll-like receptor 7 variant associated with systemic lupus erythematosus*. PLOS Genetics, 2013. e1003336. In addition, lupus standard-of-care (SOC) anti-malarial drugs such as chloroquine disrupt endosomal TLR7/9 signaling and inhibit PBMC and/or pDC IFNalpha production induced by ssRNA-ribonucleoprotein complexes or lupus patient serum. Moreover, myeloid DC and monocytes produce IL-12p40, TNF alpha, and IL-6 following self-RNA/TLR8 signaling, suggesting the additional contribution of TLR8-dependent pro-inflammatory cytokines to human lupus etiology in addition to TLR7-driven IFN by pDC. Vollmer, supra; Gorden, K. B., et al., *Synthetic TLR agonists reveal functional differences between human TLR7 and TLR8*. J Immunol, 2005. 174(3): p. 1259-68.

Mouse model evidence also exists for the role of TLR in lupus. Published studies have collectively demonstrated that both single TLR7 or dual TLR7/9 gene deletion or dual TLR7/9 pharmacologic inhibition reduces disease severity in four distinct lupus models. Nickerson, K. M., et al., *TLR9 regulates TLR7- and MyD88-dependent autoantibody production and disease in a murine model of lupus*. J Immunol, 2010. 184(4): p. 1840-8; Fairhurst, A. M., et al., *Yaa autoimmune phenotypes are conferred by overexpression of TLR7*. Eur J Immunol, 2008. 38(7): p. 1971-8; Deane, J. A., et al., *Control of toll-like receptor 7 expression is essential to restrict autoimmunity and dendritic cell proliferation*. Immunity, 2007. 27(5): p. 801-10; Savarese, E., et al., *Requirement of Toll-like receptor 7 for pristane-induced production of autoantibodies and development of murine lupus nephritis*. Arthritis Rheum, 2008. 58(4): p. 1107-15. Highlighting the role of TLR7 as a critical determinant of autoimmunity, transgenic overexpression of TLR7 alone leads to spontaneous anti-RNA auto-reactivity and nephritis in the normally disease-resistant C57BL/6 strain. Deane, supra.

From a safety perspective, there are no reports that TLR7, 8, or 9-single or 7/8- and 7/9-dual gene deficient mice are immune-compromised to the extent that infection by opportunistic pathogens is observed. Likewise, SOC anti-malarials are thought to be largely safe and effective for long-term use in humans to control lupus disease flare at doses predicted to at least partially inhibit TLR7/9 signaling. Lafyatis, R., M. York, and A. Marshak-Rothstein, *Antimalarial agents: closing the gate on Toll-like receptors?* Arthritis Rheum, 2006. 54(10): p. 3068-70; Costedoat-Chalumeau, N., et al., *Low blood concentration of hydroxychloroquine is a marker for and predictor of disease exacerbations in patients with systemic lupus erythematosus*. Arthritis Rheum, 2006. 54(10): p. 3284-90. In fact, save for increased susceptibility to Gram-positive bacterial infections in childhood and to a lesser extent in adulthood, humans with highly compromised TLR and IL-1R signaling pathways (MyD88- or IRAK-4-deficiency) are nonetheless healthy and maintain sufficient host defense mechanisms. Casanova, J. L., L. Abel, and L. Quintana-Murci, *Human TLRs and IL-1Rs in Host Defense: Natural Insights from Evolutionary, Epidemiological, and Clinical Genetics*, Annu Rev Immunol, 2010.

Based on this and other information, we believe that TLR7 in particular is a well-validated target in the context of mouse pre-clinical SLE models. Both genetic and functional human studies support the hypothesis that antagonism of the TLR7 and/or TLR8 pathways will afford therapeutic benefit to lupus patients. Moreover, both mouse TLR gene deletion studies and the long-term use of anti-malarials in humans suggest that pharmacological TLR7, 8 and/or 9 suppression can be undertaken without significantly compromising host defense.

A compound that suppresses TLR7, TLR8, or both TLR7 and TLR8 may therefore be expected to act as a therapeutic or prophylactic agent for SLE or lupus nephritis.

We have found compounds that suppress TLR 7 and/or 8 and are therefore expected to have a prophylactic or therapeutic effect on SLE or lupus nephritis. Compounds and methods of the disclosure are described herein.

II. Therapeutic Use

Dosage levels of active ingredients in the pharmaceutical compositions of the disclosure may be varied to obtain an amount of the active compound(s) that achieves the desired therapeutic response for a particular patient, composition, and mode of administration. The selected dosage level depends upon the activity of the particular compound, the route of administration, the severity of the condition being treated, and the condition and prior medical history of the patient being treated. Doses are determined for each particular case using standard methods in accordance with factors unique to the patient, including age, weight, general state of health, and other factors that can influence the efficacy of the compound(s) of the disclosure. In general, in the case of oral administration, the compound according to the present disclosure or a pharmaceutically acceptable salt thereof is administered at a dose of approximately 30 μg to 100 μg, a dose of 30 μg to 500 μg, a dose of 30 μg to 10 g, a dose of 100 μg to 5 g, or a dose of 100 μg to 1 g per adult per day. In the case of administration via injection, it is administered at a dose of approximately 30 μg to 1 g, a dose of 100 μg to 500 mg, or a dose of 100 μg to 300 mg per adult per day. In both cases, a dose is administered once or divided over several administrations. Dosage may be simulated, for example, using the Simcyp® program.

It is not intended that the administration of a compound of the disclosure to a mammal, including humans, be limited to a particular mode of administration, dosage, or frequency of dosing. The present disclosure contemplates all modes of administration, including oral, intraperitoneal, intramuscular, intravenous, intraarticular, intralesional, subcutaneous, or any other route sufficient to provide a dose adequate to prevent or treat SLE or lupus nephritis. One or more compounds of the disclosure may be administered to a mammal in a single dose or multiple doses. When multiple doses are administered, the doses may be separated from one another by, for example, several hours, one day, one week, one month, or one year. It is to be understood that, for any particular subject, specific dosage regimes should be adjusted over time according to the individual need and the professional judgment of the person administering or supervising the administration of a pharmaceutical composition that includes a compound of the disclosure.

For clinical applications, a compound of the present disclosure may generally be administered intravenously, subcutaneously, intramuscularly, colonically, nasally, intraperitoneally, rectally, buccally, or orally. Compositions containing at least one compound of the disclosure that is suitable for use in human or veterinary medicine may be presented in forms permitting administration by a suitable route. These compositions may be prepared according to the customary methods, using one or more pharmaceutically acceptable adjuvants or excipients. The adjuvants comprise, inter alia, diluents, sterile aqueous media, and various non-toxic organic solvents. Acceptable carriers or diluents for therapeutic use are well known in the pharmaceutical field, and are described, for example, in Remington: The Science and Practice of Pharmacy (20th ed.), ed. A. R. Gennaro, Lippincott Williams & Wilkins, 2000, Philadelphia, and Encyclopedia of Pharmaceutical Technology, eds. J. Swarbrick and J. C. Boylan, 1988, 1999, Marcel Dekker, New York. The compositions may be presented in the form of tablets, pills, granules, powders, aqueous solutions or suspensions, injectable solutions, elixirs, or syrups, and the compositions may optionally contain one or more agents chosen from the group comprising sweeteners, flavorings, colorings, and stabilizers to obtain pharmaceutically acceptable preparations.

The choice of vehicle and the content of active substance in the vehicle are generally determined in accordance with the solubility and chemical properties of the product, the particular mode of administration, and the provisions to be observed in pharmaceutical practice. For example, excipients such as lactose, sodium citrate, calcium carbonate, and dicalcium phosphate and disintegrating agents such as starch, alginic acids, and certain complex silicates combined with lubricants (e.g., magnesium stearate, sodium lauryl sulfate, and talc) may be used for preparing tablets. To prepare a capsule, it is advantageous to use lactose and high molecular weight polyethylene glycols. When aqueous suspensions are used, they may contain emulsifying agents that facilitate suspension. Diluents such as sucrose, ethanol, polyethylene glycol, propylene glycol, glycerol, chloroform, or mixtures thereof may also be used.

For parenteral administration, emulsions, suspensions, or solutions of the compositions of the disclosure in vegetable oil (e.g., sesame oil, groundnut oil, or olive oil), aqueous-organic solutions (e.g., water and propylene glycol), injectable organic esters (e.g., ethyl oleate), or sterile aqueous solutions of the pharmaceutically acceptable salts are used. The solutions of the salts of the compositions of the disclosure are especially useful for administration by intramuscular or subcutaneous injection. Aqueous solutions that include solutions of the salts in pure distilled water may be used for intravenous administration with the proviso that (i) their pH is adjusted suitably, (ii) they are appropriately buffered and rendered isotonic with a sufficient quantity of glucose or sodium chloride, and (iii) they are sterilized by heating, irradiation, or microfiltration. Suitable compositions containing a compound of the disclosure may be dissolved or suspended in a suitable carrier for use in a nebulizer or a suspension or solution aerosol, or may be absorbed or adsorbed onto a suitable solid carrier for use in a dry powder inhaler. Solid compositions for rectal administration include suppositories formulated in accordance with known methods and containing at least one compound of the disclosure.

Dosage formulations of a compound of the disclosure to be used for therapeutic administration should be sterile. Sterility is readily accomplished by filtration through sterile membranes (e.g., 0.2 micron membranes) or by other conventional methods. Formulations typically are stored in lyophilized form or as an aqueous solution. The pH of the compositions of this disclosure in some embodiments, for example, may be between 3 and 11, may be between 5 and 9, or may be between 7 and 8, inclusive.

While one route of administration is by oral dosage administration, other methods of administration may be used. For example, compositions may be administered subcutaneously, intravenously, intramuscularly, colonically, rectally, nasally, or intraperitoneally in a variety of dosage forms such as suppositories, implanted pellets or small cylinders, aerosols, oral dosage formulations, and topical formulations such as ointments, drops, and dermal patches. Compounds of embodiments of the disclosure may be incorporated into shaped articles such as implants, including but not limited to valves, stents, tubing, and prostheses, which may employ inert materials such as synthetic polymers or silicones, (e.g., Silastic® compositions, silicone rubber, or other commercially available polymers). Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, a compound of the disclosure may be coupled to a class of biodegradable polymers useful in achieving controlled release of a drug, for example polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates, and cross linked or amphipathic block copolymers of hydrogels.

A compound of the disclosure may also be administered in the form of liposome delivery systems, such as small unilamellar vesicles, large unilamellar vesicles, and multi-lamellar vesicles. Liposomes can be formed from a variety of lipids, such as cholesterol, stearylamine, or phosphatidylcholines. A compound of the disclosure may also be delivered using antibodies, antibody fragments, growth factors, hormones, or other targeting moieties to which the compound molecules are coupled (e.g., see Remington: The Science and Practice of Pharmacy, vide supra), including in vivo conjugation to blood components of a compound of an embodiment of the disclosure.

III. Synthesis

General and specific synthesis routes are provided that we found useful for preparation of embodiments of the disclosure. Those skilled in the art may recognize that certain variations or modifications of these procedures could also lead to synthesis of compounds according to the disclosure. In some situations the phrase "such as" is used to enumerate various alternatives for more generic compounds or structures. It will be understood that "such as" should not be construed to be limiting, and that its meaning is in accord with "including, for example, but not limited to."

Certain conditions were common to specific examples presented below. Microwave heating was done using a Biotage® Emrys Liberator or Initiator microwave reactor. Column chromatography was carried out using Biotage® SP4 flash chromatography system. Solvent removal was carried out using either a Büchii rotary evaporator or a Genevac® centrifugal evaporator. NMR spectra were recorded at 400 MHz on a Varian Unity® spectrometer using deuterated solvents. Chemical shifts are reported relative to residual protonated solvent.

Thin layer chromatography was performed on Whatman® glass plates precoated with a 0.25 mm layer of silica gel using various ratios of one or more of the following solvents: EtOAc, heptane, dichloromethane or MeOH.

Analytical LC/MS was performed for many examples on a Waters Acquity™ system using an XBridge™ C18 1.7 μm 2.1×50 mm column. Solvents A and B are Water w/0.1% formic acid and Acetonitrile w/0.1% formic acid, respectively. 5 minute total method time with 5% B to 99% B over 4 minutes with a flow rate of 0.3 ml/min. Mass spectral data were acquired on a Waters SQD from 100-2000 amu in electrospray positive mode.

Alternatively, purity and mass confirmation were carried out on a Waters Autopurification system using an XBridge™ C8 3.5 μm 4.6×50 mm column. Solvents A and B are water w/0.1% formic acid and acetonitrile w/0.1% formic acid, respectively. 6 minute total method time with 10% B to 95% B over 5 minutes with a flow rate of 2.5 ml/min. Mass spectral data were acquired on a Micromass ZQ™ from 130-1000 amu in electrospray positive mode.

Preparative reverse phase LC/MS was carried out for many examples on a Waters Autopurification system using an XBridge™ C8 5 μm, 19×100 mm column. Solvents A and B are water w/0.1% formic acid and Acetonitrile w/0.1% formic acid, respectively. 12 minute total method time with 30% B to 95% B over 10 minutes with a flow rate of 20 ml/min. Mass spectral data were acquired on a Micromass ZQ™ from 130-1000 amu in electrospray positive mode.

Preparative HPLC resolution of racemic compounds was carried out for many examples using one of the following chiral columns: Chiralpak® IA (5 cm×50 cm or 2 cm×25 cm), Chiralpak® AD (2 cm×25 cm) or Chiralcel® OD (2 cm×25 cm). Enantiomer ratios of purified compounds were determined by HPLC analysis on a 0.45 cm×25 cm column comprised of the same stationary phase (IA, AD or OD).

General methods and experimentals for preparing compounds of the present disclosure are set forth below. In certain cases, a particular compound is described by way of example. However, it will be appreciated that in each case a series of compounds of the present disclosure were prepared in accordance with the schemes and experimentals described below. For those compounds where NMR and/or mass spectrometry data are available, the data is presented in FIG. 3.

The following abbreviations are used herein:
Definitions: The following abbreviations have the indicated meanings:
  AcOH: acetic acid
  anhyd: anhydrous
  aq.: aqueous
  Bn: benzyl
  Boc: tert-butoxycabonyl
  CSA: Camphor sulfonic acid
  d: day(s)
  DAMP: Danger-Associated Molecular Pattern
  DBU: 1,8-Diazobicyclo[5.4.0]undec-7-ene
  DCE: 1,2-dichloroethane
  DCM: dichloromethane
  DIPEA: N,N-diisopropylethylamine
  DMA: N,N-Dimethylacetamide
  DMAP: 4-Dimethylaminopyridine
  DMF: N,N-dimethylformamide
  DMSO: Dimethyl sulfoxide
  dsDNA: double-stranded DNA
  EDC: 1-(3-dimethylaminopropyl)-3-ethylcarbodiimide hydrochloride
  ee: enantiomeric excess
  EtOAc: ethyl acetate
  EtOH: ethanol
  h: hour(s)
  HATU: N,N,N',N'-Tetramethyl-O-(7-azabenzotriazol-1-yl)uronium hexafluorophosphate
  HCl: hydrochloric acid
  HCQ: hydroxychloroquine
  hep: n-heptane
  HEPES: 4-(2-hydroxyethyl)-1-piperazineethanesulfonic acid
  HPLC: high performance liquid chromatography
  IFN: interferon
  IPA: isopropyl alcohol or isopropanol
  $K_2CO_3$: potassium carbonate
  MeOH: methanol
  $MgSO_4$: magnesium sulfate (anhydrous)
  min: minute(s)
  MTBE: methyl tert-butyl ether
  $Na_2CO_3$: sodium carbonate
  $Na_2SO_4$: sodium sulfate (anhydrous)
  $NaBH_4$: sodium borohydride
  NaCl: sodium chloride
  NaH: 60% sodium hydride dispersed in oil
  NaHCO3: sodium bicarbonate
  NaOH: sodium hydroxide
  NBS: N-bromosuccinimide
  $NH_4Cl$: ammonium chloride
  $NH_4Cl$: ammonium chloride
  $NH_4OH$: ammonium hydroxide
  NMP: N-methylpyrrolidone
  Ns: Nosyl or o-nitrobenzenesulfonyl
  ° C.: degrees Celsius
  PAMP: Pathogen-Associated Molecular Pattern
  PBMC: peripheral blood mononuclear cell
  PBS: phosphate buffered saline
  pDC: plasmacytoid dendritic cell
  $PhNTf_2$: N-phenyltrifluoromethanesulfonimide
  qPCR: quantitative polymerase chain reaction
  R848: resiquimod
  rt: room temperature
  sat: saturated
  SNAP: BIOTAGE® brand flash chromatography cartridge
  SOC: standard-of-care
  ssRNA: single-stranded RNA
  T3P: Propylphosphonic anhydride
  tBuOK: potassium tert-butyloxide
  TEA: triethylamine
  TEMPO: 2,2,6,6-Tetramethylpiperidine 1-oxyl
  Tf: trifluoromethanesulfonate
  TFA: trifluoroacetic acid
  THF: tetrahydrofuran
  TLDA: Taqman® Low Density Array
  TLR: Toll-like receptor
  TSA: p-toluenesulfonic acid
  General Synthetic Methods:

Compounds of the invention were made according to the general synthetic methods shown in the following schemes:

Scheme 1

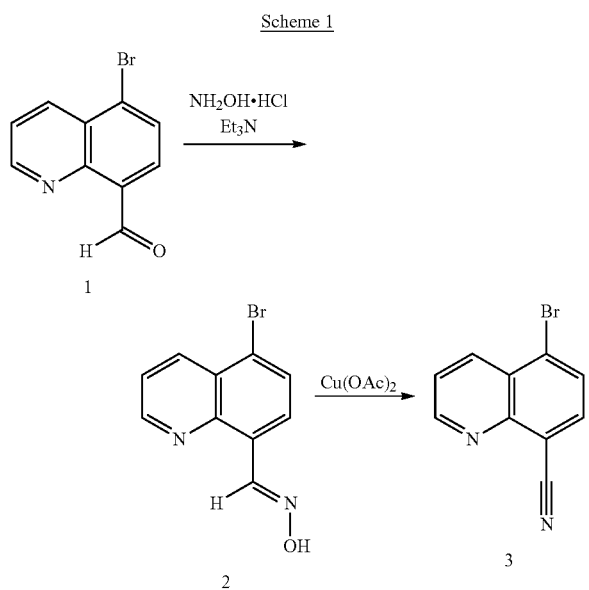

The preparation of at least one example uses intermediate 3, which can be prepared according to the route depicted in Scheme 1. The commercially available 5-bromoquinoline-8-carbaldehyde 1 (Frédérieric de Montigny, Gilles Argouarch, Claude Lapinte, "New Route to Unsymmetrical 9,10-Disubstituted Ethynylanthracene Derivatives," *Synthesis*, 2006, 293-298.) is treated with hydroxylamine hydrochloride to provide the oxime 2. 2 is subsequently converted to the corresponding nitrile 3 in the presence of catalytic amount of copper acetate to provide one of the key intermediates for this invention. Intermediate 3 is used for the generation of the compounds of this invention by the displacement of the 5-position of 5-bromoquinoline-8-carbaldehyde with appropriate aromatic, heteroaromatic and saturated heterocyclic compounds such as piperidines, piperazines and morpholines using appropriate conditions described in detail below.

An alternative method for the generation of the key intermediate 3 is shown in Scheme 2 wherein triethylamine for the first step of the synthesis is replaced with sodium acetate.

Scheme 2

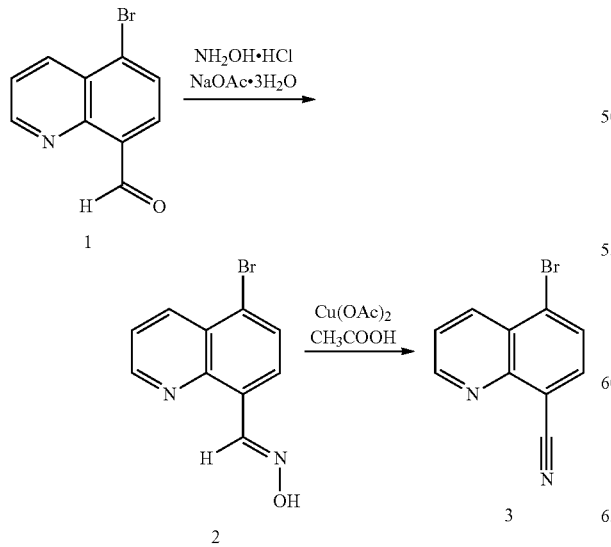

The methodology for another set of example compounds for this invention is shown in Scheme 3. Starting from the appropriately substituted, commercially available pyridine 48, the free amine is protected to provide 49 after which time the pyridine nitrogen is activated to form 50. Reduction of the pyridinium salt using borohydride or other reducing agents provides the unsaturated piperidine 51 followed by additional reducing conditions using hydrogen in the presence of a palladium catalyst to yield the disubstituted piperidine as a racemic mixture or 52 and 53. Resolution of the desired enantiomer can be performed via formation of a mixtures of diastereomeric salts using one equivalent a chiral acid such as (2R,3R)-2,3-bis((4-methoxybenzoyl)oxy)succinic acid where upon the desired diastereomeric salt crystallizes out of solution. Collection, recrystallization, and desalting of the resultant crystals allows one to obtained the desired enantiomer 53 in high ee. 53 is then coupled with the 5-bromoquinoline 3 using an appropriate coupling reagent to provide the Boc-protected 54, which is easily deprotected to example 55 or ER-888840. The alcohol analog 56 can be easily generated by subjecting the amine 55 to sodium nitrite.

Scheme 3

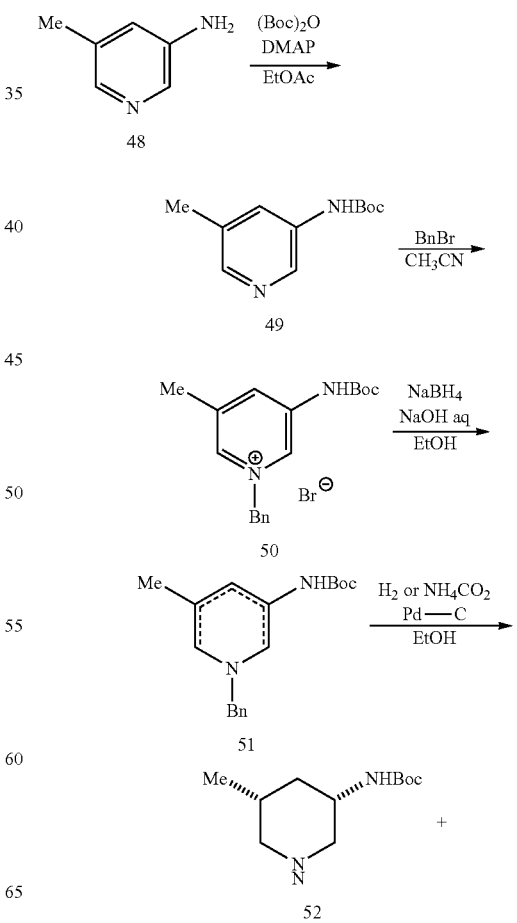

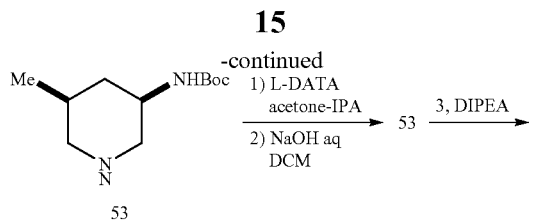
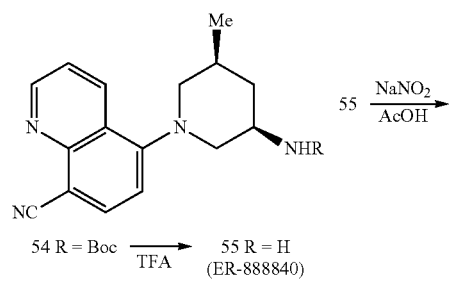
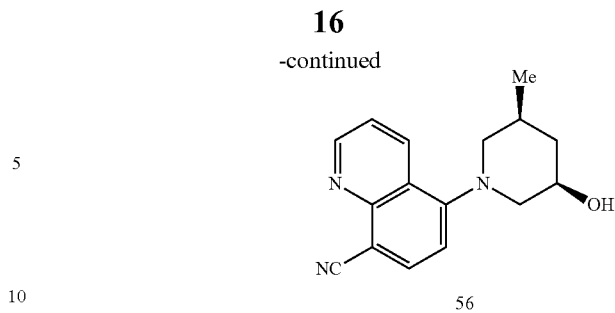

Additional example compounds can be prepared using 54 or 55 as key intermediates as shown in Schemes 4 and Scheme 5. Alkylation of 54 is possible by deprotonation of the amide proton with a strong base followed by the addition of an appropriately activated alkylating agent. Alkylation of 55 is possible by reductive amination methodology to provide examples depicted by the general structure 57. Alkylation of 55 is also possible by use an appropriate base in the presence of appropriate substituted alkyl, aryl, groups containing an appropriate leaving group (LG) provides a mixture of mono- and disubstituted examples with the general structure 57 and 58 as depicted in Scheme 4.

Scheme 4

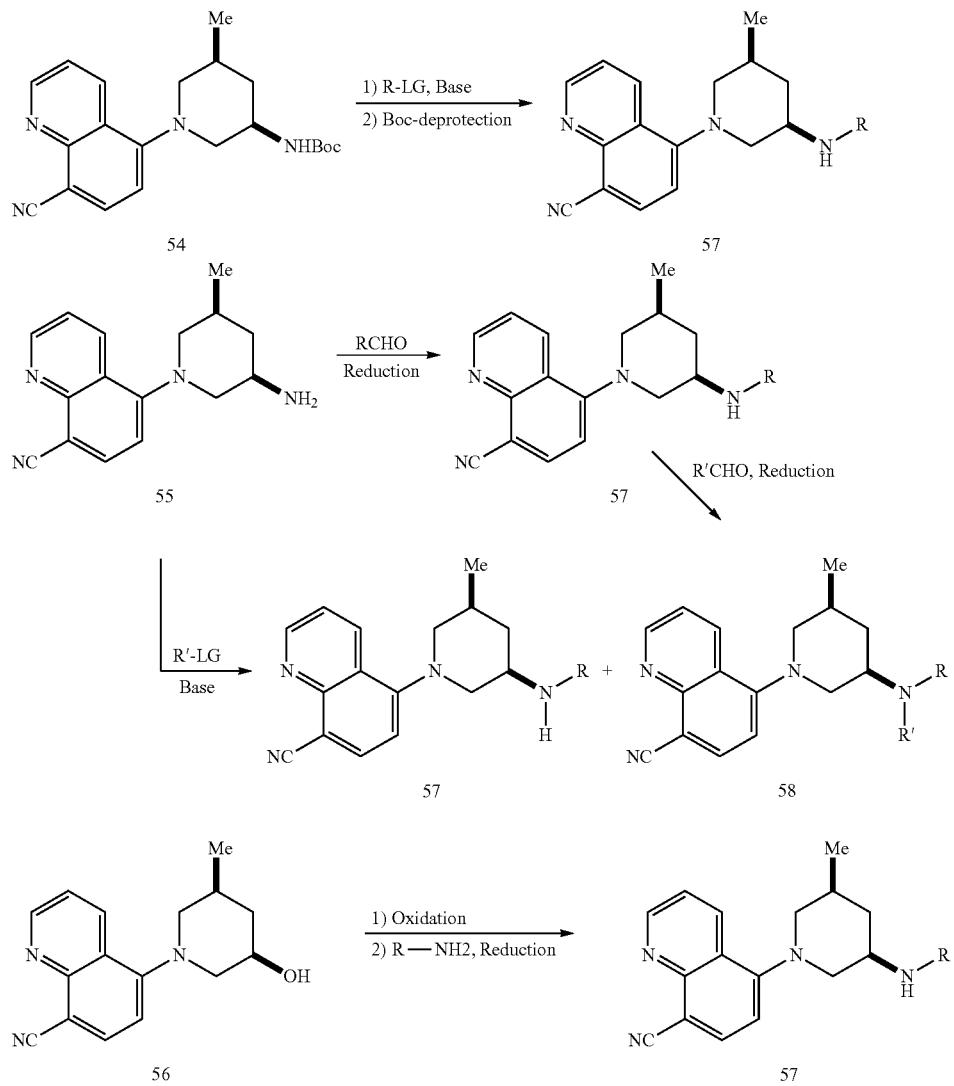

Acylation of 55 using an activated acid or using various amide or peptide coupling reagents provides amides of general structure 59 as depicted in Scheme 5. Alkylation of 59 under basic conditions provides examples depicted in general structure 60. Sulfonamides of 55 likewise can be obtained using conditions familiar to persons in the art using an activated alkyl or aryl sulfonyl reagent to form examples depicted by general structure 61.

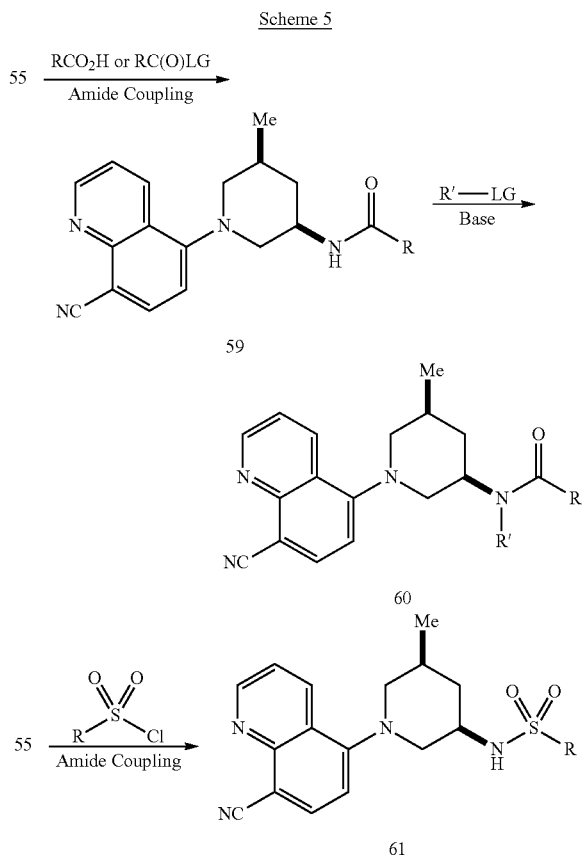

Preparation of Examples

Compound 3—Scheme 1

To a suspension of 5-bromoquinoline-8-carbaldehyde 1 (1.00 g, 4.24 mmol) and hydroxylamine hydrochloride (1.177 g, 16.94 mmol) in acetonitrile (110 mL) was added TEA (2.362 mL, 16.94 mmol) followed by heating to reflux for 3 h to afford a yellow suspension. The completed reaction completion was cooled to rt, the precipitate was filtered, and the filter cake rinsed with acetonitrile (50 mL). The crude solid was purified over a short pad of silica gel (10 g) eluting with EtOAc (300 mL) providing the aldoxime 2 as a yellow solid.

Aldoxime 2 (1.001 g, 4.0 mmol) and copper (II) acetate monohydrate (84.6 mg, 0.424 mmol) in anhydrous acetonitrile (180 mL) were stirred at reflux for 12 h. The completed reaction was cooled to rt, filtered and the filter pad washed with $H_2O$ to afford a brown solid. The crude solid was purified over a short pad of silica gel (ca. 10 g) eluting with (DCM 100 mL) to provide 5-bromoquinoline-8-carbonitrile, 3 (0.783 g, 3.4 mmol, 79.3% yield over 2 steps) as a white-beige solid after concentration and drying in vacuo the eluted product. See: Frédérieric de Montigny, Gilles Argouarch, Claude Lapinte, *Synthesis*, 2006, 293.

Compound 3—Scheme 2

To a stirred solution of sodium acetate trihydrate (31.6 g, 0.232 mol) in EtOH (0.498 L) at 15° C. was added 5-bromoquinoline-8-carbaldehyde (49.84 g, 0.211 mol) followed by hydroxylamine hydrochloride (15.55 g, 0.223 mol). The resultant mixture was heated to 70° C. for 3 h after which time the reaction was cooled to 35° C. and then diluted with water (250 mL). The mixture was partially concentrated to approximately 250 mL after which time water (250 mL), 2-methoxy-2-methylpropane (120 mL), and heptane (120 mL) were added followed by re-concentrated the mixture to approximately 250 mL. The resultant slurry was diluted with water (250 mL) and cooled to 0° C. after which time 1 M NaOH in water (211 mL) was added and the final mixture was stirred vigorously for 10 min. The suspension was filtered, rinsed with water (498 mL) and the filter cake dried at 30° C. for 18 h to afford aldoxime 2 (49.75 g, 0.198 mol, 93.9% yield) as tan powder.

To a stirred suspension of 2 (48.21 g, 0.192 mol) in acetonitrile (386 mL) at 15° C. was added copper (II) acetate (0.523 g, 2.9 mmol) followed by acetic acid (13.1 mL, 0.229 mol). The resultant mixture was heated to reflux for 21 h after which time the completed reaction was cooled to 50° C. Water (0.39 L) was added and the mixture was partially concentrated followed by dilution with water (290 mL) and cooled to 5° C. 1 M NaOH in water (230 mL) was added and vigorous stirring was continued for 10 min. The suspension was filtered, the filter cake rinsed with water (500 mL) and dried to afford compound 3 (42.80 g, 0.183 mol, 95.6% yield) as dark gray powder.

Synthesis of ER-888840 Using Scheme 3

Compound 50: To a stirred solution of commercially available 5-methylpyridin-3-amine 48 (17.52 g, 162.01 mmol) in EtOAc (52.6 mL) at 17° C. was added DMAP (0.990 g, 8.10 mmol) and the mixture was warmed up to 30° C. after which time a solution of di-tert-butyl dicarbonate (39.5 mL, 170.11 mmol) in EtOAc (35.0 mL) was slowly added to the initial reaction mixture over a 1-h period while controlling $CO_2$ evolution and temperature at <40° C. The resultant mixture was stirred at 35-40° C. for additional 1 h then heated at reflux for 18 h. The final mixture was cooled to rt, diluted with toluene (175 mL) followed by the addition of silica gel (17.52 g). The resultant slurry was stirred at 20-23° C. for 30 h then filtered and the filter cake was rinsed with a mixture of EtOAc (88 mL) and toluene (88 mL). The filtrate was partially concentrated to dry to provide crude tert-butyl (5-methylpyridin-3-yl)carbamate, 49, as an orange/brown solid.

To a stirred solution of crude 49 in acetonitrile (175 mL) was added benzyl bromide (19.85 mL, 167 mmol) at 20° C. followed by heating to reflux for 2 h. The completed reaction was the cooled to rt, diluted with toluene (315 mL), cooled to 0° C. and stirred for 1 h. The crude mixture was filtered, rinse with toluene (175 mL) and the resultant solid was dried in a vacuo at 45° C. for 17 h to provide 1-benzyl-3-((tert-butoxycarbonyl)amino)-5-methylpyridin-1-ium bromide, 50 (35.59 g, 93.8 mmol) as an off-white powder. The filtrate was concentrated and suspended in a mixture of EtOAc (150 mL) and ethanol (15 mL) and the resultant solid was filtered, rinsed with EtOAc (50 mL) and dried in vacuo to provide additional 50 (5.20 g, 13.7 mmol, or 66.4% overall yield for 2 steps).

Compound 52 and 53: To a stirred solution of 50 (9.85 g, 26.0 mmol) in ethanol (89 ml) at −3° C. was added a cooled (0° C.) solution of NaBH$_4$ (3.013 g, 79.6 mmol) in 0.10 M NaOH (20 ml, 2.0 mmol) maintaining the temperature at <3° C., after which time the reaction was stirred at 0-3° C. for 3 h. The completed reaction was diluted with MTBE (0.10 L) and water (0.05 L) maintaining the temperature at <10° C. followed by the addition 20 wt % citric acid (50 g) while controlling H$_2$ evolution and temperature at <10° C. The resultant mixture was vigorously stirred at 5-10° C. for 10 min then partially concentrated to approximately 50 ml. MTBE (100 mL) was added under vigorous stirring and the mixture was re-concentrated to approximately 50 ml. Resultant mixture was extracted with MTBE (0.10 L×2) and the combined organic layers were washed with water (20 ml), 9 wt % NaHCO$_3$ (3 g), concentrated, and azeotroped two times with ethanol (50 ml each). The resultant mixture was diluted with MTBE (50 ml) and filtered. The filtrate was concentrated and diluted with ethanol to adjust total weight of 50.0 g of crude 51 which was used in the next step without further concentration or purification.

Formation of 52 & 53 via hydrogenation with H$_2$ gas: A 5.0 g aliquot of 51 (10% of total above) was diluted with ethanol (10 ml) and subjected to hydrogenation with 10 wt % Pd—C (0.272 g) under 1.04 bar H$_2$ gas. After 24 h, the reaction mixture was filtered through a pad of Celite (2 g). Reactor and filter cake were rinsed with ethanol (10 ml) and filtrate was concentrated dry to give tert-butyl ((3S,5R)-5-methylpiperidin-3-yl)carbamate, 52 & tert-butyl ((3R,5S)-5-methylpiperidin-3-yl)carbamate, 53 (0.472 g, 2.21 mmol, 85% yield, 1:5-6 ratio of 52:53 via 1H-NMR) as white solid.

Formation of 52 & 53 via transfer hydrogenation: 10 g aliquot of 51 (20% of total above) was concentrated and mixed with water (10 ml) followed by the addition of ammonium formate (3.28 g, 52 mmol) and ethanol (20 ml). 5 wt % Pd—C (0.548 g) was added under N$_2$ atmosphere after which time the resultant mixture was stirred at 25-30° C. for 20 h. The completed reaction was filtered through a pad of Celite 545 (4 g), the filter cake was rinsed with ethanol (20 ml) and the filtrate was concentrated to dry. 1.0 M NaOH (6 ml) was added and the mixture was extracted two times with DCM (40 ml each). The combined organic layers were washed with 25 wt % NaCl (6 ml), dried over Na$_2$SO$_4$ (4 g), filtered and concentrated to give 52 & 53 as yellow-white solid (0.844 g, 3.94 mmol, 75% yield, cis/trans 3:1).

Compound 52 can also be prepared according to the reported method (WO2010/009014, incorporated by reference herein).

Resolution of 53: The racemic mixture of 52 & 53 (84 g, 0.392 mol) was suspended in acetone/IPA 95:5 (1596 ml & 84 ml). (2R,3R)-2,3-bis((4-methoxybenzoyl)oxy)succinic acid (L-DATA; 164 g, 0.392 mol) was added at ambient temperature and resultant mixture was stirred overnight (20 h). White precipitates were collected by filtration, rinsed with pre-chilled acetone (1600 ml), and dried under vacuum. Recovered diastereomeric salt (dr=94.9:5.1) was subjected to re-slurring in acetone (1000 ml). Filtration followed by drying gave 65 g of 53½ L-DATA salt (dr=98.5:1.5, 0.15 mol, 39% yield). Chiral HPLC conditions: Lux 3u Cellulose-4 column (00G-4490-E0), mobile phase using isocratic mixture of 90% A (MeCN+0.1% DEA) and 10% B (MeOH+0.1% DEA).

To stirred suspension of 53¼ L-DATA salt (156 g, 0.368 mol) in DCM (1248 ml) was added 1.0 M NaOH (624 ml, 0.624 mol) slowly at ambient temperature. After 111, the layers were partitioned. The aqueous layer was extracted with DCM (1200 ml). The combined organic layers were washed with water (1500 ml) and concentrated to give 53 as white solid (75 g, 0.350 mol, 95% yield).

Compound 55 (ER-888840): To a stirred suspension of 53 (2.52 g, 11.74 mmol) and 3 (2.28 g, 9.78 mmol) in DMA (6.84 ml) was added DIPEA (3.42 ml) followed by heating and refluxing for 3 h. The completed reaction was cooled to rt, partitioned between EtOAc/n-heptane 2:1 (180 ml) and 5 wt % NaCl (60 ml), and filtered through a pad of Celite 545 (5 g). The organic layer was washed with 5 wt % NaCl (60 ml), treated with Florisil (7.7 g), filtered, rinsed with EtOAc (30 ml) and concentrated. Crude product thus obtained was purified over silica gel (40 g, eluting stepwise with DCM/MeOH 19:1, 9:1 & 4:1) to provide tert-butyl ((3R,5S)-1-(8-cyanoquinolin-5-yl)-5-methylpiperidin-3-yl)carbamate, 54, as orange-colored solid which was used directly in the next reaction.

To a stirred solution of 54 in DCM (20 ml) was added slowly TFA (20 ml) and stirred for an additional 30 min. The completed reaction was concentrated, partitioned between DCM (500 ml) and saturated NaHCO$_3$ (220 g). The organic layer was washed with sat. NaHCO$_3$ (220 g) and concentrated to give crude product as orange-colored solid/oil, which was purified over silica gel (40 g, eluting with EtOAc 100%, then stepwise DCM/MeOH 4:1 & 7:3) to give 55 (ER-888840, 1.401 g, 5.26 mmol, 53% yield based on 47) as orange foam.

ER-888840-HCl: 55 (33.3 mg, 0.125 mmol) was suspended in IPA (9.63 mL) and heated to 45° C. followed by the addition of 0.1M HCl (1.13 mL, 0.12 mmol) while maintaining the temperature 40-45° C. Resultant mixture was cooled down to rt and stirring was continued for 2 h. Yellow precipitates were collected by filtration, rinsed with IPA (2.0 mL), dried under N2/vacuum, for 2 h, and further dried in vacuum oven at 45° C. for 20 h to give ER-888840-HCl as yellow solid (14.5 mg, 0.048 mmol, 38% yield).

ER-878921 (5.2 mg, 0.021 mmol, 32.8% yield) was prepared in a similar manner to ER-888840 starting with Compound 3 (15 mg, 0.064 mmol) and (R)-piperidin-3-amine dihydrochloride (13.4 mg, 0.077 mmol). The reaction was microwaved at 180° C. for 3 h and purified by methods described for this series of examples.

Preparation of ER-896464 or Compound 56, Scheme 14:
To a stirred suspension of ER-888840 (175 mg, 0.657 mmol) in acetic acid (1 mL, 17.468 mmol) was added sodium nitrite (91 mg, 1.314 mmol) in 150 uL water dropwise over 3 min. The mixture was stirred 40 min at rt upon which time ER-888840 was demonstrated to remain via TLC. An additional 1 eq of sodium nitrite in 100 uL water was added and the mixture was stirred an additional 1 h at rt. The completed reaction was concentrated and the residue was dissolved in DCM (10 mL), washed with sat. NaHCO$_3$ (5 mL), dried over MgSO$_4$, filtered and concentrated to dry. The residue was dissolved in ethanol (1 mL) and treated with 10% aq sodium hydroxide (100 uL). After stirring 90 min at rt the mixture was diluted with methylene chloride and washed with water, dried over MgSO$_4$), filtered and concentrated to dry. The residue was purified over silica gel (Biotage, eluting with 0 to 70% EtOAc/heptanes) to provide 2 eluted compounds tentatively identified a cis- and trans-isomers of the 0-acetate. The major peak eluted with 70% EtOAc/heptanes identified as the hydroxy epimers as a 4:1-5:1 mixture of cis- to trans-isomers. With the cis-56 or ER-896464 (95 mg, 0.355 mmol, 54.1% yield) as the major diastereomer.

Preparation of ER-897184.HCl:

To a stirred solution of 54 (100 mg, 0.273 mmol) in DMF (1.00 ml, 12.915 mmol) was added sodium hydride (60% oil dispersion, 12.01 mg, 0.30 mmol). The mixture was stirred 30 m at rt after which time methyl iodide (0.020 ml, 0.327 mmol) was added. The final reaction mixture was stirred 2 h at rt after which time the completed reaction was slowly quenched with aqueous ammonium chloride (5 mL). The mixture was extracted three times with 1:1 EtOAc/heptanes (3 mL each), and the combined organic extracts were washed with water (3 mL), brine (3 mL), dried over $MgSO_4$), filtered and concentrated. The crude product was purified over silica gel eluting with 40% EtOAc/heptanes to provide tert-butyl ((3R,5S)-1-(8-cyanoquinolin-5-yl)-5-methylpiperidin-3-yl)(methyl)carbamate (96 mg, 0.252 mmol, 92% yield).

To a stirred solution of tert-butyl ((3R,5S)-1-(8-cyanoquinolin-5-yl)-5-methylpiperidin-3-yl)(methyl)carbamate (96 mg, 0.252 mmol) in DCM (1.0 ml) was added and TFA (1.00 ml, 12.98 mmol). The mixture was stirred at rt for 1 h after which time the complete reaction was concentrated to dryness, the residue was dissolved in MeOH (10 mL), and MP-carbonate basic resin (~250 mg) was added. The mixture was stirred at rt for 30 min after which time the suspension was filtered, the filtrate concentrated and dried in vacuo. The amine was treated with 4.0 M HCl in Dioxane (0.037 mL) at rt for 30 min, after which time the mixture azeotroped to dryness two times with toluene (2 mL each) and dried in vacuo to provide ER-897184-HCl (79.8 mg, 0.252 mmol, 100.0% yield) as an orange solid.

ER-897275 (49 mg, 0.151 mmol, 55.3% yield) was prepared in a similar manner to ER-897184 starting with 54-2HCl (100 mg, 0.273 mmol) and 1-bromo-2-methoxyethane (37.9 mg, 0.273 mmol). The secondary amine was isolated without forming the HCl salt.

Preparation of ER-899369.HCl Via Reductive Amination of Compound 55, Scheme 4:

To a stirred solution of tert-butyl (3-formyloxetan-3-yl)carbamate (47 mg, 0.234 mmol) and 55 (81 mg, 0.304 mmol) in DCE (5 ml) was added sodium triacetoxyborohydride (99 mg, 0.467 mmol). The reaction mixture was stirred 18 h at rt, after which time the completed reaction was quenched with 1N NaOH (5 mL). After stirring 10 min the mixture was diluted with water (5 mL) and EtOAc (10 mL). The aqueous layer was extracted two times with EtOAc (5 mL each) and the combined organic layers were washed with water (5 mL) and brine (5 mL), dried over $MgSO_4$, filtered and concentrated. The crude product was purified over silica gel (20 g, eluting with 10-100% EtOAc/DCM) to provide the Boc-protected intermediate which was deprotected and converted ER-899369.HCl (60.1 mg, 0.155 mmol, 66.4% yield) as described for ER-897184-HCl.

ER-899075 (48.8 mg, 0.135 mmol, 91% yield) was prepared in a similar manner to ER-899369 starting with 55-2HCl (50.3 mg, 0.148 mmol) and 3-methyloxetane-3-carbaldehyde (22.5 mg, 0.225 mmol). Deprotection was not required for this example. The HCl salt was not formed.

ER-899506 (107 mg, 0.305 mmol, 92% yield) was prepared in a similar manner to ER-99075 starting with 55-2HCl (50.3 mg, 0.148 mmol) and tetrahydro-4H-pyran-4-one (0.092 ml, 0.999 mmol).

ER-899541 (11 mg, 0.034 mmol, 17.8% yield) was prepared in a similar manner to ER-99075 starting with 55-2HCl (65 mg, 0.192 mmol) and oxetan-3-one (0.025 mL, 0.384 mmol) along with DIPEA (0.05 mL, 0.288 mmol).

ER-899543 (11 mg, 0.034 mmol, 17.8% yield) was prepared in a similar manner to ER-99541 starting with 55-2HCl (57 mg, 0.168 mmol) and 5-(trifluoromethyl)picolinaldehyde (58.8 mg, 0.336 mmol).

ER-899544 (37 mg, 0.110 mmol, 65.5% yield) was prepared in a similar manner to ER-99541 starting with 55-2HCl (57 mg, 0.168 mmol) and dihydrofuran-3(2H)-one (28.9 mg, 0.336 mmol).

ER-899551 (23 mg, 0.066 mmol, 32.6% yield) was prepared in a similar manner to ER-99541 starting with 55-2HCl (69 mg, 0.203 mmol) and oxazole-2-carbaldehyde (39.4 mg, 0.406 mmol).

ER-899552 (24 mg, 0.067 mmol, 32.6% yield) was prepared in a similar manner to ER-99541 starting with 55-2HCl (69 mg, 0.203 mmol) and 1-methyl-1H-imidazole-4-carbaldehyde (44.7 mg, 0.406 mmol).

ER-899563 (8.8 mg, 0.021 mmol, 12.3% yield) was prepared in a similar manner to ER-99541 starting with 55-2HCl (57 mg, 0.168 mmol) and 6-(trifluoromethyl)nicotinaldehyde (58.8 mg, 0.336 mmol).

ER-899564 (17 mg, 0.049 mmol, 12.3% yield) was prepared in a similar manner to ER-99541 starting with 55-2HCl (58 mg, 0.171 mmol) and 1H-pyrazole-5-carbaldehyde (33 mg, 0.342 mmol).

ER-899565 (27 mg, 0.072 mmol, 38.1% yield) was prepared in a similar manner to ER-99541 starting with 55-2HCl (64 mg, 0.189 mmol) and 1,4-dimethyl-1H-pyrazole-3-carbaldehyde (46.9 mg, 0.378 mmol).

ER-899566 (25 mg, 0.067 mmol, 36.0% yield) was prepared in a similar manner to ER-99541 starting with 55-2HCl (63 mg, 0.186 mmol) and 3,5-dimethylisoxazole-4-carbaldehyde (46.5 mg, 0.372 mmol).

ER-899577 (18 mg, 0.052 mmol, 31.8% yield) was prepared in a similar manner to ER-99541 starting with 55-2HCl (55 mg, 0.162 mmol) and pyrrolidine-2,4-dione (32.1 mg, 0.324 mmol).

ER-899602 (11 mg, 0.028 mmol, 4.8% yield) was prepared in a similar manner to ER-99541 starting with 55-2HCl (201 mg, 0.592 mmol) and 3-(methylthio)propanal (123 mg, 1.185 mmol) followed by dissolving the intermediate thiol in DCM (3 ml), cooling to 0° C. and adding 3-chloroperoxybenzoic acid (255 mg, 1.48 mmol). The reaction mixture was stirred at 0° C. for 5 min, warmed to RT, and stirred an additional 3 h. 3-chloroperoxybenzoic acid (100 mg, 0.580 mmol) was added after cooling the reaction to 0° C. followed by stirring at RT for 1 h. The completed reaction was diluted with DCM (10 mL) and washed with saturated $NaHCO_3$ (5 mL) and brine (5 mL). The combined aqueous layers were extracted two times with DCM (5 mL each) after which time the combined organic layers were dried over anhydrous $Na_2SO_4$, filtered, and concentrated to dry. The crude residue was purified over silica gel (Biotage ultra, 10 g, eluted with a gradient of 0 to 20% MeOH in DCM) followed by concentration of the desired fractions and re-purifying over a reverse phase HPLC column ((X-Bridge C18 19×100 mm column; eluting with a gradient of increasing acetonitrile in water containing 0.1% $NH_4OH$). The desired fractions were concentrated and dried in vacuo to provide ER-899602.

ER-899604 (18 mg, 0.050 mmol, 25.0% yield) was prepared in a similar manner to ER-99541 starting with 55-2HCl (68 mg, 0.200 mmol) and 2-oxocyclopentanecarbonitrile (43.7 mg, 0.401 mmol).

ER-899607 (15 mg, 0.040 mmol, 22.1% yield) was prepared in a similar manner to ER-99541 starting with 55-2HCl (62 mg, 0.183 mmol) and 1-(pyridin-2-yl)ethanone (0.041 mL, 0.365 mmol).

ER-899621 (25 mg, 0.071 mmol, 42.5% yield) was prepared in a similar manner to ER-99541 starting with 55-2HCl (57 mg, 0.168 mmol) and dihydro-2H-pyran-3 (4H)-one (33.6 mg, 0.336 mmol).

ER-899633 (41.2 mg, 0.103 mmol, 52.3% yield) was prepared in a similar manner to ER-99541 starting with 55-2HCl (67 mg, 0.197 mmol) and dihydro-2H-thiopyran-4(3H)-one 1,1-dioxide (58.5 mg, 0.395 mmol).

ER-899634 (20 mg, 0.052 mmol, 30.9% yield) was prepared in a similar manner to ER-99541 starting with 55-2HCl (57 mg, 0.168 mmol) and 1-(6-methylpyridin-2-yl)ethanone (45.4 mg, 0.336 mmol).

ER-899630 (12 mg, 0.033 mmol, 8.7% yield) and ER-899631 (19 mg, 0.052 mmol, 13.7% yield) was prepared in a similar manner to ER-899541 starting with 55-2HCl (129 mg, 0.380 mmol) and 4-hydroxycyclohexanone (87 mg, 0.76 mmol) where both diastereomers were isolated via silica gel chromatography. Note: The stereochemistry for both compounds is arbitrarily assigned and has not been confirmed.

ER-899632 (12 mg, 0.033 mmol, 18.9% yield) was prepared by the oxidation of the diastereomeric mixture of ER-899630 & ER-899631 (64 mg, 0.176 mmol) by adding DMP (373 mg, 0.879 mmol) in four portions over 1 h per portion at rt in DCM (3 mL). The completed reaction was diluted with DCM (10 mL) and washed with saturated NaHCO$_3$ (5 mL) then brine (5 mL). The combined aqueous layers were extracted two times with DCM (5 mL each) after which time the combined organic layers were dried over anhydrous Na$_2$SO$_4$, filtered and concentrated to dry. The crude residue was purified over silica gel (Biotage ultra, 10 g, eluted with a 0 to 20% MeOH in DCM), followed by concentration of the desired fractions and re-purifying over a reverse phase HPLC column ((X-Bridge C18 19×100 mm column; eluting with a gradient of increasing acetonitrile in water containing 0.1% NH$_4$OH). The desired fractions were concentrated and dried in vacuo to provide ER-899632.

ER-899508: To a stirred suspension of 55 (85 mg, 0.251 mmol) and potassium carbonate (34.6 mg, 0.251 mmol) in DMF (1 mL, 12.92 mmol), was added 3,3,3-trifluoropropyl methanesulfonate (0.052 mL, 0.376 mmol). The reaction was stirred at rt for 24 h after which time the reaction was diluted with EtOAc-Heptane (~4:1) (10 mL) and water (5 mL). The aqueous layer was extracted two times with EtOAc-Heptane (~4:1) (5 mL each) and the combined organic layers were washed with brine (5 mL), dried over anhydrous Na$_2$SO$_4$, filtered, and concentrated under reduced pressure. The crude was purified over silica gel (12 g column, eluting with 25 100% EtOAc in Heptane) to provide ER-899508 (3.7 mg, 0.013 mmol, 5.0% yield) as a by-product after combining the desired fractions, concentration and drying in vacuo.

ER-899823: To a stirred solution of oxalyl chloride (0.108 ml, 1.234 mmol) in DCM (2 mL) at −78° C. was added DMSO (0.175 ml, 2.469 mmol) dropwise. After the addition was complete the mixture was stirred 30 m at −78° C. after which time a solution of ER-896464 (220 mg, 0.823 mmol) in DCM (2 mL) was added dropwise followed by warming to rt and stirring for an additional 1 h. DIPEA (0.719 ml, 4.115 mmol) was added dropwise, stirred for 1 h followed by being quenched with aqueous ammonium chloride (2 mL). The mixture was extracted three times with EtOAc (5 mL each). The combined organic layers were washed with brine (5 mL), dried over MgSO$_4$, filtered and concentrated to provide crude (S)-5-(3-methyl-5-oxopiperidin-1-yl)quinoline-8-carbonitrile was used in the next step without further purification.

To a stirred solution of (S)-5-(3-methyl-5-oxopiperidin-1-yl)quinoline-8-carbonitrile (50 mg, 0.188 mmol) and 2-aminopropan-1-ol (28.3 mg, 0.377 mmol) in DCE (2 mL, 25.384 mmol) was added acetic acid (10.79 µL, 0.188 mmol) and sodium triacetoxyborohydride (160 mg, 0.754 mmol) followed by heating at 50° C. for 24 h. The completed reaction was cooled to rt, quenched with 1N NaOH (2 mL) and water (5 mL). The mixture was extracted three times with EtOAc (5 mL each), and the combined organic layers were washed with brine (5 mL), dried over MgSO$_4$, filtered and concentrated. The crude product was purified over silica gel (10 g, eluting with 0 to 10% MeOH in DCM) to provide ER-899823 (29 mg, 0.089 mmol, 47.4% yield) after combining the desired fractions, concentration and drying in vacuo.

ER-899504 & ER-899505: To a stirred suspension of ER-888840 (688 mg, 2.028 mmol) and potassium carbonate (423 mg, 3.061 mmol) in DMF (3.00 mL) was added ethyl bromoacetate (368 µl, 3.305 mmol). The reaction mixture was stirred at rt for 14 h after which time the completed reaction was diluted with sat. NaHCO$_3$ (5 mL) and EtOAc (10 mL) and the layers separated. The aqueous layer was extracted two times with EtOAc (5 mL each) and the combined organic layers were washed with brine (5 mL), dried over Na$_2$SO$_4$, filtered and concentrated. The crude product was purified by over silica gel (10 g, eluted with 0 to 100% EtOAc in heptane) to provide two products as a yellow oils after combining each desired fractions, concentration and drying under vacuo ER-899505 (382 mg, 0.871 mmol, 43.0% yield) and ER-899504 (207 mg, 0.587 mmol, 29.0% yield).

ER-899715: To a stirred solution of ER-899541(40 mg, 0.124 mmol) in 37% aq formaldehyde (1 ml, 0.124 mmol) was added formic acid (70 µl, 1.825 mmol) followed by heating at 100° C. for 2 h. The completed reaction was diluted with aqueous NaHCO$_3$ (5 mL) and extracted three times with EtOAc (3 mL each). The combined organic layers were washed with brine (5 mL), dried over MgSO$_4$, filtered and concentrated. The residue was dissolved in EtOAc (0.5 mL) followed by acetic acid (0.008 mL, 0.124 mmol) and stirred 30 min at rt, after which time it was concentrated dry in vacuo to provide ER-899715-HOAc (32 mg, 0.081 mmol, 65.1% yield) with no further purification required.

ER-896310: To a stirred solution of ER-888840 (100 mg, 0.375 mmol) in DCM (1.0 ml, 15.542 mmol) was added pyridine (0.091 ml, 1.126 mmol) followed by acetic anhydride (0.043 ml, 0.451 mmol). The reaction mixture was stirred 2 h at rt after which time the completed reaction was diluted with DCM (5 mL) and washed with aq NaHCO$_3$ (2 mL). The organic layer was dried over MgSO$_4$, filtered and concentrated. The crude product was purified over silica gel (Biotage) to provide ER-896310 (97 mg, 0.315 mmol, 84% yield) after separate combining each desired fractions, concentration and drying under vacuo.

ER-898758 (17 mg, 0.047 mmol, 15.9% yield) was prepared in a similar manner to ER-896310 starting with ER-888840-2HCl (100 mg, 0.295 mmol) and trifluoroacetic anhydride (0.052 mL, 0.368 mmol).

ER-898912: To a mixture of ER-888840 (50 mg, 0.188 mmol) and pyridine (0.046 mL, 0.563 mmol) in DCM (2 mL) was added 5-methylisoxazole-3-carbonyl chloride (27.3 mg, 0.188 mmol). The mixture was stirred 18 h at rt, followed by the addition of DMAP (23 mg, 0.188 mmol) and allowed reaction mixture to stir 6 h at rt. HATU (85.8 mg, 0.226 mmol) was added and the reaction was stirred for 18 h at room temp. The completed reaction was diluted with DCM (10 mL) and then washed with 0.5 M citric acid (3 mL), water (3 mL) and sat. NaHCO$_3$ (3 mL). The organic layer was dried over MgSO$_4$, filtered and concentrated followed by purification over silica gel (10 g, eluting with 0-10% MeOH in DCM). The desired fractions were combined, concentrated and dried in vacuo to provide ER-898912 (51 mg, 0.136 mmol, 72.4% yield).

ER-897272: To a stirred solution of ER-888840 (50 mg, 0.188 mmol), 2-(dimethylamino)acetic acid hydrochloride (31.4 mg, 0.225 mmol), and HBTU (85 mg, 0.225 mmol) in DCM (2 mL) was added TEA (78 µl, 0.563 mmol). The reaction mixture was stirred for 18 h at rt after which time the completed reaction was diluted with EtOAc (5 mL), washed with aq. NH4Cl (2 mL), water (2 mL), and brine (2 mL). The organic layer was dried over MgSO4, filtered, concentrated, and purified over silica gel chromatography (Biotage, 10 g, eluting with 0-30% EtOAc in heptanes) to provide ER-897272 (40 mg, 0.114 mmol, 60.5% yield) after concentration and drying in vacuo of the desired fractions.

ER-897273 (43 mg, 0.127 mmol, 67.6% yield) was prepared in a similar manner to ER-897272 starting with ER-888840 (50 mg, 0.188 mmol) and 2-methoxyacetic acid (20.29 mg, 0.225 mmol).

ER-897274 (53 mg, 0.163 mmol, 87.2% yield) was prepared in a similar manner to ER-897272 starting with ER-888840 (50 mg, 0.188 mmol) and 2-((tert-butoxycarbonyl)amino)acetic acid (39.5 mg, 0.225 mmol), followed by de-protecting the Boc-group using TFA and neutralization methodologies described in previous examples.

ER-897607.HCL (47 mg, 0.121 mmol, 64.9% yield) was prepared in a similar manner to ER-897272 starting with ER-888840 (50 mg, 0.188 mmol) and 2-((tert-butoxycarbonyl)amino)-2-methylpropanoic acid (45.8 mg, 0.225 mmol) with the addition of EDC (54.0 mg, 0.282 mmol), followed by de-protecting the Boc-group using HCl in dioxane following the methodologies described in previous examples.

ER-897608.HCl (40 mg, 0.107 mmol, 71.2% yield) was prepared in a similar manner to ER-897607 starting with ER-888840 (40 mg, 0.150 mmol) and 2-((tert-butoxycarbonyl)-(methyl)amino)acetic acid (34.1 mg, 0.18 mmol).

ER-897971: To a stirred solution of ER-888840-HCl (35.0 mg, 0.103 mmol) in NMP (500.0 µl) was added 2-hydroxyacetic acid (11.0 mg, 0.145 mmol), HBTU (43.0 mg, 0.113 mmol), and DIPEA (45.0 µl, 0.258 mmol). The reaction mixture was stirred at 50° C. overnight followed by direct purification over a reverse-phase HPLC column ((X-Bridge C18 19×100 mm column; eluting with a gradient of increasing acetonitrile in water containing 0.1% NH4OH). The fractions containing product were combined and concentrated in vacuo to provide ER-897971 (16.9 mg, 0.052 mmol, 50.5% yield).

ER-897972 (15.2 mg, 0.014 mmol, 13.8% yield) was prepared in a similar manner to ER-897971 starting with ER-888840-HCl (35.0 mg, 0.103 mmol) and (S)-2-hydroxy-3-methylbutanoic acid (18.0 mg, 0.152 mmol).

ER-897973 (5.2 mg, 0.039 mmol, 38.1% yield) was prepared in a similar manner to ER-897971 starting with ER-888840-HCl (35.0 mg, 0.103 mmol) and 3-hydroxybenzoic acid (21.0 mg, 0.152 mmol).

ER-897975 (4.7 mg, 0.012 mmol, 11.8% yield) was prepared in a similar manner to ER-897971 starting with ER-888840-HCl (35.0 mg, 0.103 mmol) and 4-hydroxybenzoic acid (21.0 mg, 0.152 mmol).

ER-897976 (15.9 mg, 0.045 mmol, 43.5% yield) was prepared in a similar manner to ER-897971 starting with ER-888840-HCl (35.0 mg, 0.103 mmol) and 2-(methylthio)acetic acid (16.0 mg, 0.151 mmol).

ER-897977 (16.7 mg, 0.045 mmol, 43.9% yield) was prepared in a similar manner to ER-897971 starting with ER-888840-HCl (35.0 mg, 0.103 mmol) and 2-(ethylthio)acetic acid (18.0 mg, 0.150 mmol).

ER-897978 (12.6 mg, 0.033 mmol, 31.6% yield) was prepared in a similar manner to ER-897971 starting with ER-888840-HCl (35.0 mg, 0.103 mmol) and 2-(methylsulfonyl)acetic acid (21.0 mg, 0.152 mmol).

ER-897979 (9.2 mg, 0.027 mmol, 26.2% yield) was prepared in a similar manner to ER-897971 starting with ER-888840 (35.0 mg, 0.103 mmol) and (S)-2-((tert-butoxycarbonyl)amino)propanoic acid (29.4 mg, 0.155 mmol), followed by de-protecting the Boc-group using TFA and neutralization methodologies described in previous examples.

ER-897980 (12.6 mg, 0.033 mmol, 32.0% yield) was prepared in a similar manner to ER-897979 starting with 54b (35.0 mg, 0.103 mmol) and (R)-2-((tert-butoxycarbonyl)amino)propanoic acid (28.4 mg, 0.150 mmol).

ER-897981 (12.8 mg, 0.037 mmol, 35.9% yield) was prepared in a similar manner to ER-897979 starting with ER-888840 (35.0 mg, 0.103 mmol) and 1-((tert-butoxycarbonyl)amino)-cyclopropanecarboxylic acid (30.7 mg, 0.153 mmol).

ER-897982 (1.9 mg, 0.005 mmol, 4.9% yield) was prepared in a similar manner to ER-897979 starting with ER-888840 (35.0 mg, 0.103 mmol) and (R)-2-((tert-butoxycarbonyl)amino)-3-hydroxypropanoic acid (30.9 mg, 0.151 mmol).

ER-897983 (5.6 mg, 0.015 mmol, 14.6% yield) was prepared in a similar manner to ER-897979 starting with ER-888840 (35.0 mg, 0.103 mmol) and (R)-1-(tert-butoxycarbonyl)pyrrolidine-2-carboxylic acid (33.2 mg, 0.154 mmol).

ER-897984 (0.3 mg, 0.001 mmol, 1.0% yield) was prepared in a similar manner to ER-897979 starting with ER-888840 (35.0 mg, 0.103 mmol) and 2-(1-(tert-butoxycarbonyl)azetidin-3-yl)acetic acid (33.0 mg, 0.153 mmol).

ER-897985 (8.7 mg, 0.024 mmol, 23.3% yield) was prepared in a similar manner to ER-897979 starting with ER-888840 (35.0 mg, 0.103 mmol) and 1-(tert-butoxycarbonyl)pyrrolidine-3-carboxylic acid (32.3 mg, 0.150 mmol).

ER-897986 (12.5 mg, 0.034 mmol, 33.0% yield) was prepared in a similar manner to ER-897979 starting with ER-888840 (35.0 mg, 0.103 mmol) and 2-((tert-butoxycarbonyl)amino)-3-methylbutanoic acid (34.0 mg, 0.156 mmol).

ER-897987 (2.8 mg, 0.008 mmol, 7.8% yield) was prepared in a similar manner to ER-897979 starting with ER-888840 (35.0 mg, 0.103 mmol) and (S)-2-((tert-butoxycarbonyl)amino)-3-methylbutanoic acid (33.5 mg, 0.154 mmol).

ER-897988 (9.9 mg, 0.027 mmol, 26.2% yield) was prepared in a similar manner to ER-897979 starting with ER-888840 (35.0 mg, 0.103 mmol) and 5-((tert-butoxycarbonyl)amino)pentanoic acid (33.1 mg, 0.152 mmol).

ER-897989 (9.0 mg, 0.025 mmol, 24.3% yield) was prepared in a similar manner to ER-897979 starting with ER-888840 (35.0 mg, 0.103 mmol) and (S)-2-((tert-butoxycarbonyl)amino)pentanoic acid (32.7 mg, 0.151 mmol).

ER-897990 (3.5 mg, 0.010 mmol, 9.2% yield) was prepared in a similar manner to ER-897979 starting with ER-888840 (35.0 mg, 0.103 mmol) and (S)-2-((tert-butoxycarbonyl)amino)-3-methoxypropanoic acid (33.0 mg, 0.151 mmol).

ER-897991 (7.1 mg, 0.019 mmol, 18.4% yield) was prepared in a similar manner to ER-897979 starting with ER-888840 (35.0 mg, 0.103 mmol) and (2R,3S)-2-((tert-butoxycarbonyl)amino)-3-hydroxybutanoic acid (33.9 mg, 0.155 mmol).

ER-897992 (12.2 mg, 0.032 mmol, 31.1% yield) was prepared in a similar manner to ER-897979 starting with ER-888840 (35.0 mg, 0.103 mmol) and 1-(tert-butoxycarbonyl)piperidine-4-carboxylic acid (34.8 mg, 0.152 mmol).

ER-897993 (9.7 mg, 0.026 mmol, 25.2% yield) was prepared in a similar manner to ER-897979 starting with ER-888840 (35.0 mg, 0.103 mmol) and 2-(1-(tert-butoxycarbonyl)piperidine-3-carboxylic acid (34.4 mg, 0.150 mmol).

ER-897994 (9.8 mg, 0.026 mmol, 25.2% yield) was prepared in a similar manner to ER-897979 starting with ER-888840 (35.0 mg, 0.103 mmol) and 2-(1-(tert-butoxycarbonyl)pyrrolidin-3-yl)acetic acid (34.4 mg, 0.150 mmol).

ER-897995 (10.8 mg, 0.030 mmol, 27.2% yield) was prepared in a similar manner to ER-897979 starting with ER-888840 (35.0 mg, 0.103 mmol) and 4-(tert-butoxycarbonyl)piperazine-2-carboxylic acid (34.5 mg, 0.150 mmol).

ER-897996 (11.2 mg, 0.028 mmol, 29.1% yield) was prepared in a similar manner to ER-897979 starting with ER-888840 (35.0 mg, 0.103 mmol) and (2S,4R)-1-(tert-butoxycarbonyl)-4-hydroxypyrrolidine-2-carboxylic acid (35.0 mg, 0.151 mmol).

ER-897997 (4.9 mg, 0.013 mmol, 12.6% yield) was prepared in a similar manner to ER-897979 starting with ER-888840 (35.0 mg, 0.103 mmol) and (2S,3S)-2-((tert-butoxycarbonyl)amino)-3-methylpentanoic acid (35.6 mg, 0.154 mmol).

ER-897998 (9.3 mg, 0.025 mmol, 24.3% yield) was prepared in a similar manner to ER-897979 starting with ER-888840 (35.0 mg, 0.103 mmol) and (R)-2-((tert-butoxycarbonyl)amino)-4-methylpentanoic acid (35.7 mg, 0.154 mmol).

ER-897999 (7.7 mg, 0.020 mmol, 29.5% yield) was prepared in a similar manner to ER-897979 starting with ER-888840 (35.0 mg, 0.103 mmol) and (S)-2-((tert-butoxycarbonyl)amino)-4-methylpentanoic acid (34.8 mg, 0.150 mmol).

ER-898000 (9.5 mg, 0.025 mmol, 24.3% yield) was prepared in a similar manner to ER-897979 starting with ER-888840 (35.0 mg, 0.103 mmol) and (S)-2-((tert-butoxycarbonyl)amino)-3,3-dimethylbutanoic acid (34.9 mg, 0.151 mmol).

ER-898001 (3.3 mg, 0.009 mmol, 8.7% yield) was prepared in a similar manner to ER-897979 starting with ER-888840 (35.0 mg, 0.103 mmol) and (R)-2-((tert-butoxycarbonyl)amino)-3,3-dimethylbutanoic acid (34.9 mg, 0.151 mmol).

ER-898334 (4.5 mg, 0.012 mmol, 11.7% yield) was prepared in a similar manner to ER-897979 starting with ER-888840 (35.0 mg, 0.103 mmol) and 2-((tert-butoxycarbonyl)(methyl)amino)-3-methylbutanoic acid (35.0 mg, 0.151 mmol).

ER-898335 (5.1 mg, 0.013 mmol, 12.6% yield) was prepared in a similar manner to ER-897979 starting with ER-888840 (35.0 mg, 0.103 mmol) and (S)-4-amino-3-((tert-butoxycarbonyl)amino)-4-oxobutanoic acid (35.3 mg, 0.152 mmol).

ER-898336 (2.6 mg, 0.007 mmol, 6.6% yield) was prepared in a similar manner to ER-897979 starting with ER-888840 (35.0 mg, 0.103 mmol) and (S)-4-amino-2-((tert-butoxycarbonyl)amino)-4-oxobutanoic acid (35.3 mg, 0.152 mmol).

ER-898337 (2.8 mg, 0.007 mmol, 7.1% yield) was prepared in a similar manner to ER-897979 starting with ER-888840 (35.0 mg, 0.103 mmol) and (R)-4-amino-2-((tert-butoxycarbonyl)amino)-4-oxobutanoic acid (35.4 mg, 0.152 mmol).

ER-898338 (4.5 mg, 0.012 mmol, 11.7% yield) was prepared in a similar manner to ER-897979 starting with ER-888840 (35.0 mg, 0.103 mmol) and (S)-3-(tert-butoxycarbonyl)thiazolidine-4-carboxylic acid (35.8 mg, 0.153 mmol).

ER-898339 (2.7 mg, 0.007 mmol, 6.8% yield) was prepared in a similar manner to ER-897979 starting with ER-888840 (35.0 mg, 0.103 mmol) and 4-((tert-butoxycarbonyl)amino)benzoic acid (36.1 mg, 0.152 mmol).

ER-898341 (7.5 mg, 0.019 mmol, 18.4% yield) was prepared in a similar manner to ER-897979 starting with ER-888840 (35.0 mg, 0.103 mmol) and 2-(1-(tert-butoxycarbonyl)piperidin-4-yl)acetic acid (36.0 mg, 0.148 mmol).

ER-898342 (8.8 mg, 0.022 mmol, 21.3% yield) was prepared in a similar manner to ER-897979 starting with ER-888840 (35.0 mg, 0.103 mmol) and 1-(tert-butoxycarbonyl)-4-methylpiperidine-4-carboxylic acid (36.0 mg, 0.148 mmol).

ER-898343 (2.2 mg, 0.006 mmol, 5.4% yield) was prepared in a similar manner to ER-897979 starting with ER-888840 (35.0 mg, 0.103 mmol) and 1-((tert-butoxycarbonyl)amino)-3-hydroxycyclopentanecarboxylic acid (37.0 mg, 0.151 mmol).

ER-898344 (9.4 mg, 0.024 mmol, 23.3% yield) was prepared in a similar manner to ER-897979 starting with ER-888840 (35.0 mg, 0.103 mmol) and (S)-2-((tert-butoxycarbonyl)(methyl)amino)-4-methylpentanoic acid (37.0 mg, 0.151 mmol).

ER-898345 (8.0 mg, 0.020 mmol, 19.4% yield) was prepared in a similar manner to ER-897979 starting with ER-888840 (35.0 mg, 0.103 mmol) and (S)-2-((tert-butoxycarbonyl)amino)-4,4-dimethylpentanoic acid (37.0 mg, 0.151 mmol).

ER-898346 (6.5 mg, 0.017 mmol, 16.5% yield) was prepared in a similar manner to ER-897979 starting with ER-888840 (35.0 mg, 0.103 mmol) and (S)-2-((tert-butoxycarbonyl)-(methyl)amino)hexanoic acid (37.0 mg, 0.151 mmol).

ER-898347 (0.9 mg, 0.002 mmol, 2.2% yield) was prepared in a similar manner to ER-897979 starting with ER-888840 (35.0 mg, 0.103 mmol) and (S)-5-amino-2-((tert-butoxycarbonyl)amino)-5-oxopentanoic acid (37.0 mg, 0.150 mmol).

ER-898348 (6.3 mg, 0.016 mmol, 15.5% yield) was prepared in a similar manner to ER-897979 starting with ER-888840 (35.0 mg, 0.103 mmol) and (R)-2-((tert-butoxycarbonyl)amino)-3-(ethylthio)propanoic acid (37.0 mg, 0.148 mmol).

ER-898349 (6.0 mg, 0.015 mmol, 14.6% yield) was prepared in a similar manner to ER-897979 starting with ER-888840 (35.0 mg, 0.103 mmol) and 2-((tert-butoxycarbonyl)amino)-4-(methylthio)butanoic acid (37.0 mg, 0.148 mmol).

ER-898350 (5.6 mg, 0.014 mmol, 13.6% yield) was prepared in a similar manner to ER-897979 starting with ER-888840 (35.0 mg, 0.103 mmol) and (R)-2-((tert-butoxycarbonyl)amino)-2-phenylacetic acid (38.0 mg, 0.151 mmol).

ER-898351 (8.6 mg, 0.022 mmol, 21.3% yield) was prepared in a similar manner to ER-897979 starting with ER-888840 (35.0 mg, 0.103 mmol) and (S)-2-((tert-butoxycarbonyl)amino)-2-phenylacetic acid (38.0 mg, 0.151 mmol).

ER-898352 (5.1 mg, 0.013 mmol, 12.6% yield) was prepared in a similar manner to ER-897979 starting with ER-888840 (35.0 mg, 0.103 mmol) and (S)-2-((tert-butoxycarbonyl)amino)-3-(1H-imidazol-4-yl)propanoic acid (38.0 mg, 0.149 mmol).

ER-898353 (6.8 mg, 0.017 mmol, 16.5% yield) was prepared in a similar manner to ER-897979 starting with ER-888840 (35.0 mg, 0.103 mmol) and 3-(1-(tert-butoxycarbonyl)piperidin-2-yl)propanoic acid (39.0 mg, 0.152 mmol).

ER-898354 (4.9 mg, 0.012 mmol, 11.7% yield) was prepared in a similar manner to ER-897979 starting with ER-888840 (35.0 mg, 0.103 mmol) and 3-(1-(tert-butoxycarbonyl)piperidin-3-yl)propanoic acid (39.0 mg, 0.152 mmol).

ER-898355 (3.2 mg, 0.008 mmol, 7.7% yield) was prepared in a similar manner to ER-897979 starting with ER-888840 (35.0 mg, 0.103 mmol) and 1-((tert-butoxycarbonyl)amino)-4-hydroxycyclohexanecarboxylic acid (39.0 mg, 0.150 mmol).

ER-898356 (3.3 mg, 0.008 mmol, 7.8% yield) was prepared in a similar manner to ER-897979 starting with ER-888840 (35.0 mg, 0.103 mmol) and (R)-2-((tert-butoxycarbonyl)amino)-3-phenylpropanoic acid (40.0 mg, 0.151 mmol).

ER-898357 (9.1 mg, 0.022 mmol, 21.3% yield) was prepared in a similar manner to ER-897979 starting with ER-888840 (35.0 mg, 0.103 mmol) and (2S)-2-((tert-butoxycarbonyl)amino)-4-(methylsulfinyl)butanoic acid (40.1 mg, 0.151 mmol).

ER-898358 (12.6 mg, 0.030 mmol, 29.1% yield) was prepared in a similar manner to ER-897979 starting with ER-888840 (35.0 mg, 0.103 mmol) and (S)-2-((tert-butoxycarbonyl)amino)-3-(pyridin-2-yl)propanoic acid (40.0 mg, 0.150 mmol).

ER-898359 (16.3 mg, 0.039 mmol, 37.9% yield) was prepared in a similar manner to ER-897979 starting with ER-888840 (35.0 mg, 0.103 mmol) and (S)-2-((tert-butoxycarbonyl)amino)-3-(pyridin-4-yl)propanoic acid (40.0 mg, 0.150 mmol).

ER-898360 (17.1 mg, 0.041 mmol, 39.8% yield) was prepared in a similar manner to ER-897979 starting with ER-888840 (35.0 mg, 0.103 mmol) and (S)-2-((tert-butoxycarbonyl)amino)-3-(pyridin-3-yl)propanoic acid (40.0 mg, 0.150 mmol).

ER-898361 (19.6 mg, 0.047 mmol, 45.6% yield) was prepared in a similar manner to ER-897979 starting with ER-888840 (35.0 mg, 0.103 mmol) and (R)-2-((tert-butoxycarbonyl)amino)-3-(pyridin-3-yl)propanoic acid (40.0 mg, 0.150 mmol).

ER-898362 (9.1 mg, 0.022 mmol, 21.4% yield) was prepared in a similar manner to ER-897979 starting with ER-888840 (35.0 mg, 0.103 mmol) and 5-(tert-butoxycarbonyl)-4,5,6,7-tetrahydro-1H-pyrazolo[4,3-c]pyridine-3-carboxylic acid (40.0 mg, 0.150 mmol).

ER-898364 (9.1 mg, 0.022 mmol, 21.4% yield) was prepared in a similar manner to ER-897979 starting with ER-888840 (35.0 mg, 0.103 mmol) and 2-(1-(((tert-butoxycarbonyl)amino)methyl)-cyclohexyl)acetic acid (41.7 mg, 0.154 mmol).

ER-898365 (11.7 mg, 0.028 mmol, 27.2% yield) was prepared in a similar manner to ER-897979 starting with ER-888840 (35.0 mg, 0.103 mmol) and (S)-2-((tert-butoxycarbonyl)amino)-3-(thiazol-4-yl)propanoic acid (41.0 mg, 0.151 mmol).

ER-898366 (13.7 mg, 0.032 mmol, 31.1% yield) was prepared in a similar manner to ER-897979 starting with ER-888840 (35.0 mg, 0.103 mmol) and (S)-2-((tert-butoxycarbonyl)(methyl)amino)-3-phenylpropanoic acid (42.0 mg, 0.150 mmol).

ER-898367 (14.5 mg, 0.034 mmol, 33.0% yield) was prepared in a similar manner to ER-897979 starting with ER-888840 (35.0 mg, 0.103 mmol) and (R)-2-((tert-butoxycarbonyl)(methyl)amino)-3-phenylpropanoic acid (43.0 mg, 0.154 mmol).

ER-898368 (6.8 mg, 0.016 mmol, 15.5% yield) was prepared in a similar manner to ER-897979 starting with ER-888840 (35.0 mg, 0.103 mmol) and (S)-2-((tert-butoxycarbonyl)amino)-3-(4-hydroxyphenyl)propanoic acid (42.2 mg, 0.150 mmol).

ER-898369 (9.5 mg, 0.022 mmol, 21.4% yield) was prepared in a similar manner to ER-897979 starting with ER-888840 (35.0 mg, 0.103 mmol) and (S)-2-((tert-butoxycarbonyl)amino)-4-(methylsulfonyl)butanoic acid (43.0 mg, 0.153 mmol).

ER-898758 (9.5 mg, 0.022 mmol, 21.4% yield) was prepared in a similar manner to ER-897979 starting with ER-888840 (35.0 mg, 0.103 mmol) and (S)-2-((tert-butoxycarbonyl)amino)-4-(methylsulfonyl)butanoic acid (43.0 mg, 0.153 mmol).

ER-898761:

To a stirred solution of ER-888840-2HCl (50 mg, 0.147 mmol) and DCM (1.0 ml, 15.542 mmol) and TEA (0.041 ml, 0.295 mmol) was added. 3,3,3-trifluoropropanoic acid (56.6 mg, 0.442 mmol) and HOBT (29.9 mg, 0.221 mmol) followed by cooling 0° C. EDC (85 mg, 0.442 mmol) was added and the resultant reaction mixture was stirred at 40° C. for 3 h. The completed reaction was diluted with DCM (2 mL) and washed with saturated aqueous NH$_4$Cl (1 mL), saturated aqu. NaHCO$_3$ (1, mL), and brine (1 mL). The organic layer was dried over anhydrous Na$_2$SO$_4$, filtered and concentrated followed by purification over silica gel (Biotage SP4. Column Interchim 25 g) to provide ER-898761 (36 mg, 0.096 mmol, 64.9% yield) as a white solid after concentration and drying in vacuo the desired fractions.

ER-898991 (3.6 mg, 0.009 mmol, 5.1% yield) and ER-898992 (1.6 mg, 0.004 mmol, 2.3% yield) were separated by using the preparation in a similar manner to ER-898761 starting with ER-888840-2HCl (60 mg, 0.177 mmol) and 2-amino-3,3,3-trifluoropropanoic acid (25.3 mg, 0.177 mmol). The stereochemistries of both diastereomers were arbitrarily assigned and not confirmed.

ER-899072 (51.4 mg, 0.137 mmol, 89% yield) was preparation in a similar manner to ER-898761 starting with ER-888840-2HCl (52.3 mg, 0.154 mmol) and 3-methyloxetane-3-carboxylic acid (50.2 mg, 0.432 mmol).

ER-898763 (19 mg, 0.050 mmol, 34.0% yield) was prepared in a similar manner to ER-898761 starting with ER-888840-2HCl (50 mg, 0.147 mmol) and (S)-3-((tert-butoxycarbonyl)amino)-4-methylpentanoic acid (102 mg, 0.442 mmol) followed by de-protecting the Boc-group using TFA and neutralization methodologies described in previous examples.

ER-898765 (19 mg, 0.054 mmol, 36.7% yield) was prepared in a similar manner to ER-898763 starting with ER-888840-2HCl (50 mg, 0.147 mmol) and (S)-3-((tert-butoxycarbonyl)amino)butanoic acid (90 mg, 0.442 mmol).

ER-898901 (42 mg, 0.120 mmol, 81.6% yield) was prepared in a similar manner to ER-898763 starting with ER-888840-2HCl (50 mg, 0.147 mmol) and (S)-2-((tert-butoxycarbonyl)(methyl)amino)propanoic acid (90 mg, 0.442 mmol).

ER-898902 (13 mg, 0.034 mmol, 23.1% yield) was prepared in a similar manner to ER-898763 starting with ER-888840-2HCl (50 mg, 0.147 mmol) and (R)-3-((tert-butoxycarbonyl)amino)-4-methylpentanoic acid (102 mg, 0.442 mmol).

ER-898976 (19 mg, 0.054 mmol, 36.7% yield) was prepared in a similar manner to ER-898763 starting with ER-888840-2HCl (50 mg, 0.147 mmol) and (R)-3-((tert-butoxycarbonyl)amino)butanoic acid (90 mg, 0.442 mmol).

ER-898977 (50 mg, 0.132 mmol, 89.8% yield) was prepared in a similar manner to ER-898763 starting with ER-888840-2HCl (50 mg, 0.147 mmol) and (S)-2-((tert-butoxycarbonyl)(methyl)amino)-3-methylbutanoic acid (102 mg, 0.442 mmol).

ER-899127: To a stirred solution of (R)-4-(tert-butoxycarbonyl)morpholine-3-carboxylic acid (87 mg, 0.375 mmol) in THF (2.0 ml) at rt, was added 4-methylmorpholine (0.041 ml, 0.375 mmol) followed by isobutyl chloroformate (0.049 ml, 0.375 mmol) drop wise. Separately, a solution of ER-888840-2HCl (51.2 mg, 0.150 mmol) and DIPEA (0.052 ml, 0.30 mmol) was stirred at rt, after 15 min, this solution was added to the mixed anhydride prepared previously. The total reaction mixture was stirred an additional 3 h after which time the completed reaction was concentrated and the residue dissolved in DCM (5 mL). The solution was purified over silica gel (12 g, eluting with 0-75% EtOAc in heptane) to provide Boc-protected intermediate as a yellow solid.

The intermediate was dissolved in DCM (1.0 ml), and TFA (1.00 ml, 12.98 mmol) was added in one portion. The mixture was stirred at rt for 1 h after which time the complete reaction was concentrated to dryness. The residue was dissolved in MeOH (10 mL) and MP-carbonate basic resin 250 mg) was added. The mixture was stirred at rt for 30 min, at which time, the orange color had given way to a pale yellow. The suspension was filtered, the filtrate concentrated, and dried in vacuo to provide ER-899127 (21.7 mg, 0.057 mmol, 37.9% yield).

ER-899128 (29.9 mg, 0.078 mmol, 52.2% yield) was prepared in a similar manner to ER-899127 starting with ER-888840-2HCl (51.2 mg, 0.150 mmol) and (S)-4-(tert-butoxycarbonyl)morpholine-3-carboxylic acid (87 mg, 0.375 mmol).

ER-898881 (101 mg, 0.266 mmol, 31.6% yield) was prepared in a similar manner to ER-899127 starting with ER-888840-2HCl (250 mg, 0.841 mmol) and (S)-tert-butyl 2-(aminomethyl)morpholine-4-carboxylate (364 mg, 1.682 mmol).

ER-898979: To a stirred solution of 2(1H-imidazol-4-yl)acetic acid hydrochloride (33 mg, 0.200 mmol) in DMF (0.5 mL) was added HATU (76 mg, 0.200 mmol). The mixture was stirred 30 min at rt after which time ER-888840-2HCl (68 mg, 0.200 mmol) in DMF (0.5 mL) was added followed by DIPEA (0.14 mL, 0.80 mmol). The mixture was stirred 24 h at rt, after which time it was quenched aq. NaHCO$_3$ (2 mL) and water (10 mL). The solid was collected by filtration, washed with water, dried in vacuo and purified over silica gel (10 g, 0-10% MeOH in DCM) to provide ER-898979 (23 mg, 0.061 mmol, 30.7% yield) after collection of the desired fractions, concentration and drying in vacuo.

ER-898980 (30 mg, 0.078 mmol, 36.7% yield) was prepared in a similar manner to ER-898979 starting with ER-888840-2HCl (68 mg, 0.200 mmol) and 2-(pyridin-2-yl)acetic acid hydrochloride (34.7 mg, 0.200 mmol).

ER-898981 (25 mg, 0.067 mmol, 33.4% yield) was prepared in a similar manner to ER-898979 starting with ER-888840-2HCl (68 mg, 0.200 mmol) and 2-(1H-pyrazol-1-yl)acetic acid (25.2 mg, 0.200 mmol).

ER-898982 (10 mg, 0.028 mmol, 13.9% yield) was prepared in a similar manner to ER-898979 starting with ER-888840-2HCl (68 mg, 0.200 mmol) and 1H-pyrazole-4-carboxylic acid (22.4 mg, 0.200 mmol).

ER-898984 (18 mg, 0.048 mmol, 24.4% yield) was prepared in a similar manner to ER-898979 starting with ER-888840-2HCl (68 mg, 0.200 mmol) and nicotinic acid (25 mg, 0.200 mmol).

ER-898985 (27 mg, 0.072 mmol, 36.1% yield) was prepared in a similar manner to ER-898979 starting with ER-888840-2HCl (68 mg, 0.200 mmol) and 1-methyl-1H-imidazole-5-carboxylic acid (25.2 mg, 0.200 mmol).

ER-898986 (45 mg, 0.120 mmol, 60.1% yield) was prepared in a similar manner to ER-898979 starting with ER-888840-2HCl (68 mg, 0.200 mmol) and 1-methyl-1H-pyrazole-5-carboxylic acid (25.2 mg, 0.200 mmol).

ER-899350.HCl (36 mg, 0.090 mmol, 30.5% yield) was prepared in a similar manner to ER-898979 starting with ER-888840-2HCl (100 mg, 0.295 mmol) and 3-((tert-butoxycarbonyl)amino)oxetane-3-carboxylic acid (70.4 mg, 0.324 mmol) using TFA to deprotected the Boc-group and formation of the HCl salt as described in previous examples.

ER-896760: To a stirred solution of ER-888840-2HCl (100 mg, 0.295 mmol) in DCM (1.0 ml) was added TEA (0.205 ml, 1.474 mmol), followed by isopropylsulfonyl chloride (0.050 ml, 0.442 mmol). The reaction mixture was stirred for 2 h at rt, after which time the completed reaction was diluted with DCM (10 mL) followed by washing with sat. NaHCO$_3$ (5 mL) and brine (5 mL). The organic layer was dried with Na$_2$SO$_4$, filtered and concentrated followed by purification over silica gel (Biotage SP4. Column Interchim 25 g, 30 µM. 6-50% EtOAc in Heptane) to obtain ER-898760 (3.7 mg, 9.93 µmol, 3.37% yield) as a white solid after concentration of the desired product fractions, concentration and drying in vacuo.

ER-899672.HCL (25 mg, 0.055 mmol, 37.6% yield) was prepared in a similar manner to ER-898760 starting with ER-888840-2HCl (50 mg, 0.147 mmol) and 3-(dimethylamino)propane-1-sulfonyl chloride hydrochloride (65.5 mg, 0.295 mmol). The hydrochloride salt was made in a similar fashion described in other examples.

ER-899669-HCl: To a stirred solution of ER-888840-2HCl (200 mg, 0.59 mmol) in DCM (2.0 ml, 31.083 mmol) was added TEA (0.411 ml, 2.948 mmol), followed by 2-(1,3-dioxoisoindolin-2-yl)ethanesulfonyl chloride (323 mg, 1.179 mmol). The reaction mixture was stirred for 2 h at rt, after which time the completed reaction was diluted with DCM (5 mL), washed with saturated NaHCO$_3$ (2 mL) and brine (2 mL). The organic layer was dried over Na$_2$SO$_4$, filtered and concentrated followed by purification over silica gel (Biotage SP4. Column Biotage SNAP Ultra 50 g, 30 µM. 12-100% EtOAc/heptane). The desired fractions were concentrated and dried in vacuo to obtain N-((3R,5S)-1-(8- cyanoquinolin-5-yl)-5-methylpiperidin-3-yl)-2-(1,3-dioxoisoindolin-2-yl)ethanesulfonamide (266 mg, 0.528 mmol, 90% yield).

N-((3R,5S)-1-(8-cyanoquinolin-5-yl)-5-methylpiperidin-3-yl)-2-(1,3-dioxoisoindolin-2-yl)ethanesulfonamide (100 mg, 0.199 mmol) was added to hydrazine monohydrate (0.096 mL, 1.986 mmol) in THF (2.00 mL). The reaction mixture was stirred at rt overnight after which time the completed reaction was filtered through a pad of Celite 545 and rinsed with THF (5 mL). The crude product was purified over silica gel (Biotage SP4. Column Biotage SNAP Ultra 25 g, 30 μM. 1-40% MeOH/DCM) and the desired fractions were combined, concentrated and dried in vacuo to provide ER-899669 (52 mg, 0.139 mmol, 70.1% yield) as a yellow solid.

ER-899669 (52 mg, 0.139 mmol) was dissolved in 1,4-dioxane (2.0 ml) and treated with 4.00M HCl in Dioxane (0.037 mL) at rt for 30 min. The mixture was diluted with toluene (2 mL) and concentrated. The product was azeotroped with toluene (2 mL). Product was dried on vacuum pump to obtain ER-899669-HCl (57 mg, 0.139 mmol, 100.0% yield) as an orange solid.

ER-899671-HCl: A solution of ER-899669 (50 mg, 0.134 mmol) and 37% formaldehyde in water (109 mg, 1.339 mmol) in formic acid (0.1 ml, 2.607 mmol) was stirred at 80° C. for 8 h. The completed reaction was azeotroped two times with toluene (2 mL each). The residue was dissolved in MeOH (5 mL) followed by the addition of Amberlite IRA400 hydroxide form with stirring over a 10-min period until a neutral pH was obtained. The Amberlite was filtered, rinsed with MeOH and the filtrate was concentrated followed by azeotroping two times to dry with toluene (2 mL). The residue was purified over silica gel (Biotage SP4. Column Biotage SNAP Ultra 25 g, 30 μM. 1-40% MeOH/DCM) and the desired fractions were combined, concentrated and dried under vacuum to provide ER-899671 (28 mg, 0.070 mmol, 52.1% yield).

The ER-899671 (28 mg, 0.070 mmol) was dissolved in 1,4-dioxane (2.0 ml) and treated with 4.0 M HCl in dioxane (0.017 ml, 0.066 mmol) at rt for 30 min. The mixture was azeotroped three times with toluene (2 mL each). The product was dried in vacuo to provide ER-899671-HCl (30 mg, 0.068 mmol, 100% yield) as an orange solid.

Other Examples

ER-889591: ER-888840 (15 mg, 0.056 mmol), formic acid (0.0.64 mL, mmol) and 37% aq. formaldehyde (0.042 mL, mmol) were combined and microwaved at 80° C. for 8 h after which time the cooled reaction was concentrated. The crude product diluted in MeOH (2 mL) and purified over a C-18 reverser-phase HPLC, eluting with 10-100% acetonitrile in water with 0.1% TFA. The desired fractions were concentrated, dissolved in MeOH (1 ml) and passed over a basic silica gel column (Biotage Isolute SPE, 1 g $SiCO_3$, eluting with MeOH) followed by concentration and drying in vacuo to provide ER-889591 (2.1 mg, 0.007 mmol, 12.7% yield).

ER-895386: To a solution of (R)-tert-butyl (1,5-dihydroxy-4,4-dimethylpentan-2-yl)carbamate (636 mg, 2.571 mmol) and TEA (1.434 mL, 10.286 mmol) in EtOAc (10 mL) at 0° C. was added dropwise methanesulfonyl chloride (0.421 mL, 5.40 mmol) after which time the mixture was stirred 2 h at 0° C. The reaction was quenched with aq. $NaHCO_3$ (5 mL), the layers were separated and the aqueous layer was extracted three times with EtOAc (5 mL each). The combined EtOAc layers were washed with water (5 mL), dried over $MgSO_4$, filtered and concentrated to dryness. The product, (R)-4-((tert-butoxycarbonyl)amino)-2,2-dimethylpentane-1,5-diyl dimethanesulfonate (1.01 g, 2.503 mmol, 97% yield), was used without purification.

Benzylamine (0.819 ml, 7.50 mmol) was warmed to 50° C. followed by a dropwise addition of a solution of (R)-4-((tert-butoxycarbonyl)amino)-2,2-dimethylpentane-1,5-diyl dimethanesulfonate (1.009 g, 2.50 mmol) in DME (1.50 ml, 14.431 mmol) over a 15-min period. After the addition was complete the mixture was stirred at 50° C. for 20 h. The completed reaction was cooled to room temp and diluted with saturated $NaHCO_3$ (10 mL) and EtOAc (10 mL) followed by stirring vigorously for 10 min. The organic fraction from the resultant mixture was washed with brine (5 mL), dried over $MgSO_4$, filtered and concentrated. The residue was purified over silica gel (Biotage, eluting with 0 to 10% EtOAc in heptane) to provide (R)-tert-butyl (1-benzyl-5,5-dimethylpiperidin-3-yl)carbamate (500 mg, 1.570 mmol, 62.8% yield) after combining the desired fractions, concentration and drying in vacuo.

Tert-butyl ((3R,5S)-1-benzyl-5-methylpiperidin-3-yl)carbamate (500 mg, 1.642 mmol) was dissolved in ethanol (50 ml, 856.335 mmol) and hydrogenated on a H-Cube using 5% Pd/C medium catcart at 45° C. and 50 bar with $H_2$ gas, flow of solution at 1 mL/min for 7 h. The solution was concentrated to provide tert-butyl ((3R,5S)-5-methylpiperidin-3-yl)carbamate (350 mg, 1.633 mmol, 99.5% yield) as a white powder and used without further purification.

To a stirred solution of tert-butyl ((3R,5S)-5-methylpiperidin-3-yl)carbamate (890 mg, 4.153 mmol) and 5-bromoquinoline-8-carbonitrile (1452 mg, 6.229 mmol) in DMAC (14 mL) was added DIPEA (2.176 mL, 12.459 mmol) followed by sealing and heating to 110° C. and stirring for 48 h. The completed reaction was cooled to rt, diluted with water (20 mL) followed by extraction three times with EtOAc (10 mL each). The combined organic layers were washed with water (10 mL) and brine (10 mL), dried over $MgSO_4$, filtered and concentrated to dry. The crude product was purified over silica gel (Biotage, SP4 eluting with 0 to 100% EtOAc in heptane) to provide tert-butyl ((3R,5S)-1-(8-cyanoquinolin-5-yl)-5-methylpiperidin-3-yl)carbamate (817 mg, 2.229 mmol, 53.7% yield) after combining the desired fractions, concentration and drying in vacuo.

(R)-tert-butyl (1-(8-cyanoquinolin-5-yl)-5,5-dimethylpiperidin-3-yl)carbamate (70 mg, 0.184 mmol) was treated with 4 M HCl dioxane (2 ml, 8.00 mmol) and stirred 1 h at rt. The completed reaction was concentrated and dried in vacuo without further purification to provide ER-895386 (51.6 mg, 0.184 mmol, 100% yield) as a dihydrochloride salt.

ER-897810: To a stirred solution of tert-butyl ((3R,5S)-1-(8-cyanoquinolin-5-yl)-5-methylpiperidin-3-yl)carbamate, 54 (75 mg, 0.205 mmol) in ethanol (4.5 ml) was added 0.5 M sodium hydroxide (4.503 mL, 2.251 mmol) followed by 60% hydrogen peroxide in water (0.233 mL, 2.281 mmol). The reaction mixture was warmed to 50° C. and then stirred for 4 h. The completed reaction was cooled to rt followed by the addition of 5% aq sodium thiosulfate (1 mL), stirring for 5 min, and addition 1N HCl to pH7-8. The mixture was concentrated to 50% volume followed by extraction three times with DCM (5 mL each). The combined organic layers were washed with water (5 mL), dried over MgSO$_4$, filtered and concentrated to dry. The crude product was purified over silica gel (10 g, eluting with 0-60% EtOAc in heptane) to provide tert-butyl ((3R,5S)-1-(8-carbamoylquinolin-5-yl)-5-methylpiperidin-3-yl)carbamate (57 mg, 0.148 mmol, 72.4% yield) after collection of the desired fractions, concentration and drying in vacuo.

To a stirred solution of tert-butyl ((3R,5S)-1-(8-carbamoylquinolin-5-yl)-5-methylpiperidin-3-yl)carbamate (57 mg, 0.148 mmol) in DCM (5 mL) was added TFA (0.5 ml, 6.49 mmol) after which time the mixture was stirred at rt for 1 h. The completed reaction was concentrated and then dissolved in MeOH (2 mL) and treated with 0.5 g bicarbonate resin. After stirring 30 min at rt the suspension was filtered, washed two times with MeOH (1 mL) and. the combined filtrates were concentrated to a pale yellow solid. The solid was dissolved in EtOAc (1 mL), treated with 4 M HCl in dioxanes (0.029 mL, 0.115 mmol), stirred for 15 min. The resultant solid was collected by filtration and dried in vacuo to provide ER-897810-HCl (37 mg, 0.115 mmol, 78% yield).

General Screening Assay and Pharmacology Strategy.

To identify potent and selective TLR7/8 compounds, analogs were initially screened across a cell-based panel of human TLR4, TLR7, and TLR9 reporter lines (see Materials and Methods for more details). At least one compound that was potent and selective for TLR7 was also tested for TLR8 activity (see Table 2 below) and for TLR7/8 potency in the primary human PBMC assay (see Materials and Methods for more details). Certain compounds were advanced into the short-term in vivo (STIV) assay to determine dose-dependent activity and duration-of-action against mouse TLR7 (see Materials and Methods for more details). Select compounds were then evaluated for impact in one or more of the following mouse lupus disease models: BXSB-Yaa, NZBx-NZW, and Pristane:DBA/1.

Many compounds reported as embodiments herein demonstrate nanomolar potency against both human and mouse TLR7 and human TLR8 when these receptors, expressed on either cell lines or primary cells, are stimulated by synthetic, small molecule (CL097, R848) or nucleic-acid (RNA) ligands. Conversely, most compounds reported as embodiments herein are inactive against the TLR9 pathway.

Current lupus SOC drugs include anti-malarials such as chloroquine and hydroxychloroquine (HCQ) which have been shown to inhibit TLR7/9 activation in vitro. This may at least partially explain their effectiveness in controlling lupus flare. Embodiments of the disclosure, however, have been shown to offer significantly more potent inhibition. This is demonstrated by results shown in Table 1 below.

TABLE 1

Potency and selectivity of compound ER-888840 as compared to hydroxychloroquine (Plaquenil).

| Cell Format: | Ligand: | Receptor(s): | Analyte: | ER-888840 IC50 (uM) | HCQ[2] IC50 (uM) |
|---|---|---|---|---|---|
| HEK-293 | LPS | Human TLR4 | NFkB-luciferase | >10 | N.D. |
| HEK-293 | CL097 | Human TLR7 | NFkB-luciferase | 0.0002 | N.D. |
| HEK-293 | CL097 | Mouse TLR7 | NFkB-luciferase |  | N.D. |
| HEK-293 | CL097 | Human TLR8 | NFkB-luciferase |  | N.D. |
| HEK-293 | CpG-ODN | Human TLR9 | NFkB-luciferase | 8.77 | N.D. |
| Hu PBMC | [1]RNA-Ig | Human TLR7/8 | IL-6 | 0.0014 | 1-2 |
| Hu PBMC | [1]RNA-Ig | Human TLR7/8 | TNFα |  | N.D. |
| Hu PBMC | [1]RNA-Ig | Human TLR7/8 | IP-10 |  | N.D. |
| Hu PBMC | R848 | Human TLR7/8 | IL-6 |  | N.D. |
| Mu Spleen | R848 | Mouse TLR7 | IL-6 |  | N.D. |
| Hu PBMC | Pam3CSK4 | Human TLR1/2 | IL-6 |  | N.D. |
| Hu PBMC | LPS | Human TLR4 | IL-6 |  | >10 |
| Hu PBMC | CpG-ODN | Human TLR9 | IL-6 |  | 0.15-0.30 |

TABLE KEY:
[1]RNA-Ig = ssRNA derived from U1snRNA stem loop IV sequence in complex with antibody (see Materials and Methods for more details)
[2]HCQ = Hydroxychloroquine

TABLE 2

Potency of select compound against human TLR8 in the HEK-293 assay format (see Materials and Methods for more details).

| Compound Number | HEK/hTLR8 IC50 (μM) |
|---|---|
| ER-878921 | 0.0740 |

Short-Term In Vivo (STIV) Assay:

To assess compound potency in vivo against mouse TLR7, a short-term in vivo (STIV) assay was utilized. Briefly, mice were orally dosed with compounds and at various time points afterwards were injected subcutaneously with agonist R848 to stimulate TLR7. The plasma IL-6 level following R848 stimulation was then measured by ELISA to assess compound potency and duration-of-action. Importantly, cytokine production following in vitro or in vivo stimulation with R848 was shown to be completely TLR7-dependent utilizing TLR7-deficient mice. Therefore, the activity of compounds in the STIV assay can be confidently attributed to their modulation of the TLR7 pathway. A summary of STIV assay potency for a panel of compounds appears in Table 3 below.

TABLE 3

Short-term in vivo (STIV) assay data summary for select compounds.

| Time | Dose (mg/kg) | ER-888840 | ER-897608 | ER-899016 | ER-899072 | ER-899541 | ER-899544 | ER-899547 | ER-899548 | ER-899672 |
|---|---|---|---|---|---|---|---|---|---|---|
| | | | | | % Suppression vs. Vehicle | | | | | |
| 6 h | 11 | | | | | | | | | |
| | 33 | 100 | 98 | | | | | | | |
| | 100 | | | 10 | 94 | 97 | 97 | 94 | 84 | 89 |
| | 300 | | | | | | | | | |
| 12 h | 200 | | | | | | | | | |
| | 400 | | | | | | | | | |
| | 600 | | | | | | | | | |
| 13 hr | 11 | 53 | | | | | | | | |
| | 33 | 95 | 56 | | 34 | | | | | |
| | 100 | 100 | 84 | 10 | 72 | 92 | 94 | 87 | 95 | 83 |
| | 300 | | 98 | | 100 | | | | | |
| 24 hr | 11 | 24 | | | | | | | | |
| | 33 | 0 | 35 | | | | | | | |
| | 100 | 98 | 22 | | 0 | | | | | |
| | 300 | 100 | 95 | | 78 | | | | | |

Mouse Lupus Disease Models.

Two distinct lupus disease models (NZB/W and Pristane) were chosen for compound POC evaluation because (1) the NZB/W strain develops spontaneous disease with polygenic etiology, demonstrating many hallmarks of human lupus such as DNA-associated autoreactivity, proteinuria, and immune-complex mediated nephritis, and (2) positive TLR7 and/or TLR9 target validation results have been reported for both disease models.

Key findings for ER-888840 in a SLE disease model are as follows (see FIGS. 6 and 7):

1) ER-888840 suppressed multiple auto-antibody specificities in the Pristane model. ER-888840 also dose-dependently significantly reduced interferon-regulated gene expression in Pristane-induced diseased animals, as reflected in the interferon score.

Summary of Findings:

These data show a moderating effect of the compounds described on processes involved in important aspects of human lupus. Immune complexes containing nucleic acids can drive type 1 interferon production by dendritic cells, and the "interferon signature", which reflects the presence of interferon and subsequent expression of interferon regulated genes, is associated with disease severity. ER-888840 suppressed the upregulation of interferon-driven genes in the pristane model. ER-888840 limited the production of several autoantibody specificities. The results indicate that these compounds have the potential to control lupus symptoms and progression in human patients.

Pharmacology Materials & Methods:

In Vitro Pharmacology:

HEK-293 cells (ATCC) were engineered to stably express a NF-kappaB transcription factor inducible E-selectin (ELAM-1) luciferase reporter derived from the plasmid pGL3 (Promega) containing base pairs −2241 bp to −254 bp from the promoter of the human E-selectin gene (Accession No. NM_000450). These cells were then subsequently engineered to stably and individually express human TLR4, TLR7 or TLR9 full-length ORF cDNAs. Human TLR4 cDNA (Accession No. NM_138554) was cloned into pcDNA 3.0 expression vector (Invitrogen). TLR4 transfected cells were also engineered to express human MD-2 co-receptor [MD-2 cDNA (Accession No. NM_015364) was cloned into the pEF-BOS vector] and were supplemented with 10 nM soluble CD14 (R&D Systems) in the media to optimize LPS responsiveness. Human TLR9 cDNA (Accession No. NM_017442) was cloned into the pBluescript II KS vector (Agilent). Human TLR7 cDNA (Accession No. NM_016562) was obtained from OriGene. HEK-293 cells stably expressing human TLR8 (Accession No. NM_138636) or mouse TLR7 (Accession No. NM_133211) were purchased from InvivoGen and were then stably transfected with pNiFty2(NF-kappaB)-luciferase reporter plasmid (InvivoGen). Each cell type was plated in Dulbecco's modified Eagle's medium (DMEM) containing 10% fetal bovine serum (FBS) at a density of $2.22 \times 10^5$ cells/ml into a 384-well plate and incubated for 2 days at 37° C., 5% $CO_2$. Varying concentrations of antagonist compounds were then added. Cells were then incubated for another 30 minutes before adding the appropriate TLR agonist as follows (final concentrations indicated): lipopolysaccharide (LPS; Sigma) at 10 ng/ml for TLR4, CL097 (InvivoGen) at 3 ug/ml for human TLR7 and TLR8 and mouse TLR7, and CpG-2006-2A [sequence: TCGTCGTTAAGTCGTTAAGTCGTT (SEQ ID NO: 1) with phosphorothioate backbone, synthesized by Sigma-Aldrich] at 0.6 uM for TLR9. The cells were then incubated overnight, and NF-kappaB dependent luciferase reporter activation was quantified by measuring luminescence with SteadyGlo® (Promega) or Steadylite™ (Perkin Elmer) reagent as per the manufacturer's suggested protocol.

Human PBMC Cell-Based Assay.

Human peripheral blood mononuclear cells (PBMC) were isolated from freshly-drawn heparinized (10 USP units/ml, Hospira, Lakeforest, Ill.) healthy donor whole blood by density gradient (Histopaque® 1077, Sigma, Inc., St. Louis, Mo.). Briefly, 25 ml blood was diluted with 15 ml PBS (without $Ca^{2+}$, $Mg^{2+}$) in a 50 ml conical tube, and 12 ml Histopaque was underlaid using a spinal needle. Tubes were centrifuged for 45 minutes at 1200 rpm (350×g), and PBMC were collected from the buffy coat. Cells were then washed twice in PBS, and red blood cells were lysed by suspension in 5 ml ammonium chloride solution (1× Red Blood Cell Lysis Buffer, eBioscience) for 5 minutes at room temperature. After a final wash in PBS, PBMC were resuspended at a final concentration of $2 \times 10^6$/ml in RPMI-1640 media with L-glutamine (Invitrogen) and supplemented with 25 mM HEPES (Mediatech, Inc, Manassas Va.), 10% fetal bovine serum (HyClone, Logan, Utah), and Penicillin-Streptomycin-Glutamine (Mediatech) and plated at 100 ul/well ($2 \times 10^5$ cells/well) in tissue culture treated 96-well plates (Falcon).

Antagonist compounds solubilized and serial diluted in 100% DMSO were added in triplicate to cells to yield a final concentration of 0.1% DMSO (v/v). Hydroxychloroquine (Acros Organics) solubilized and serial diluted in PBS was added in triplicate to cells. PBMC were incubated with antagonist compounds or HCQ for 30 minutes at 37° C., 5% $CO_2$ before adding various TLR agonist reagents in 100 ul complete media per well as follows (final concentrations indicated): R848 (Resiquimod; GLSynthesis, Worcester, Mass.) at 1 uM for TLR7 and TLR8, $Pam_3CSK_4$ (InvivoGen) at 50 ng/ml for TLR1/2, LPS (Sigma) at 10 ng/ml for TLR4, and CpG-2216 (InvivoGen) at 5 ug/ml for TLR9. To prepare a TLR7/8 agonist that mimics RNA-containing auto-antibody immune complexes in lupus patients, a 26-mer RNA with a sequence derived from human U1 snRNA stem loop IV [(sequence: GGGGGACUGCGU-UCGCGCUUUCCC (SEQ ID NO: 2) with phosphorothioate backbone] was synthesized (Dharmacon, Inc., Lafayette, Colo.), which has been shown previously to be a potent TLR7 and TLR8 agonist. This RNA molecule was diluted to 2.5 µM in serum-free RPMI, and mouse anti-human single stranded DNA monoclonal antibody (MAB3034, Millipore, Inc., Billerica, Mass.), which also cross-reacts with RNA, was added at a 1:25 dilution or at 1 ug/ml. The resulting "RNA-Ig" stimulus was incubated at room temperature for 15-30 minutes before adding to cells. PBMC were incubated with the various TLR agonists for 20 hours at 37° C., 5% $CO_2$. Cell culture supernatants were collected, and levels of various human cytokines were assessed as indicated by standard ELISA procedure according to the manufacturer's recommended protocol (BD Biosciences, Inc., San Diego, Calif.). Results are shown in Table 4.

TABLE 4

PBMC Assay Data Summary for Selected Compounds

| Compound Number | Human PBMCs $IC_{50}$ (µM) | Compound Number | Human PBMCs $IC_{50}$ (µM) |
|---|---|---|---|
| ER-878921 | 0.090 | ER-888840 | 0.001 |
| ER-895386 | 0.017 | ER-889591 | 0.042 |
| ER-897998 | 0.002 | ER-896310 | 0.063 |
| ER-897999 | 0.002 | ER-896464 | 0.006 |
| ER-898334 | 0.008 | ER-897184 | 0.004 |
| ER-898344 | 0.022 | ER-897272 | 0.006 |
| ER-898345 | 0.017 | ER-897273 | 0.107 |
| ER-898350 | 0.020 | ER-897274 | 0.007 |
| ER-898360 | 0.011 | ER-897275 | 0.006 |
| ER-898364 | 0.000 | ER-897275 | 0.006 |
| ER-898365 | 0.016 | ER-897607 | 0.004 |
| ER-899016 | 0.006 | ER-897608 | 0.005 |
| ER-899072 | 0.008 | ER-897971 | 0.005 |
| ER-899669 | 0.009 | ER-897972 | 0.017 |
| ER-897973 | 0.011 | ER-899505 | 0.127 |
| ER-897978 | 0.014 | ER-899506 | 0.009 |
| ER-897979 | 0.001 | ER-899508 | 0.071 |
| ER-897980 | 0.027 | ER-899541 | 0.015 |
| ER-897987 | 0.012 | ER-899543 | 0.012 |
| ER-897989 | 0.002 | ER-899544 | 0.005 |
| ER-897990 | 0.003 | ER-899547 | 0.023 |
| ER-897997 | 0.001 | ER-899548 | 0.030 |
| ER-899350 | 0.067 | ER-899549 | 0.037 |
| ER-899369 | 0.013 | ER-899550 | 0.031 |
| ER-899504 | 0.081 | ER-899551 | 0.024 |
| ER-899577 | 0.065 | ER-899552 | 0.104 |
| ER-899672 | 0.003 | | |

Mouse Spleen Cell-Based Assay.

Spleens are harvested from female BALB/c mice (Jackson Labs, Bar Harbor, Me.) euthanized by $CO_2$. A single cell suspension is obtained by passing spleens through a 40 µm nylon cell strainer. Cells are washed twice with 50 ml PBS (Mediatech, Inc., Manassas, Va.) and red blood cells are lysed in 5 ml RBC Lysis buffer (eBioscience, Inc., San Diego, Calif.) for 5 minutes at room temperature. Cells are washed twice more in PBS and finally resuspended in supplemented RPMI-1640 at $2.5 \times 10^6$ cells/ml. Cells are plated at 100 µl/well ($2.5 \times 10^5$ cells/well) in 96-well tissue culture treated plates (Falcon). Serial dilutions of compounds solubilized in 100% DMSO are added in triplicate to cells to yield a final concentration of 0.1% DMSO. Cells are incubated with compound for 30 minutes at 37° C., 5% $CO_2$ before adding 100 µl/well of 740 nM R848 (Resiquimod; GLSynthesis, Worcester, Mass.) in complete media for a final concentration of 370 nM R848. Cells are incubated for 20 hours at 37° C., 5% $CO_2$. Culture supernatants are collected, and levels of IL-6 are assessed by standard ELISA procedure according to the manufacturer's recommended protocol (BD Biosciences, Inc., San Diego, Calif.).

In Vivo Pharmacology:

Short-Term In Vivo (STIV) Assay.

Six to eight week old female BALB/c mice (Jackson Labs, Bar Harbor, Me.) were dosed by oral gavage in 200 ul volume with antagonist compounds formulated in 0.5% aqueous methyl-cellulose (Sigma, St. Louis, Mo.). At various time points afterwards, mice were injected subcutaneously (s.c.) in 100 ul volume with 15 ug R848 (Resiquimod; GLSynthesis, Worcester, Mass.) to stimulate TLR7. Blood plasma was collected by cardiac puncture, and levels of IL-6 at 1.5 hours after TLR7 stimulation were then assessed by standard ELISA procedure according to the manufacturer's recommended protocol (R&D Systems).

Mouse Lupus Disease Model Strains.

Male BXSB-Yaa and female NZBWF1/J mice were purchased from Jackson Labs (Bar Harbor, Me.), both of which manifest with spontaneous lupus disease. Female DBA/1 mice were purchased from Harlan Laboratories (Indianapolis, Ind.) and at the indicated ages given an intraperitoneal injection of 0.5 ml pristane (2,6,10,14-Tetramethylpentadecane; Sigma, St. Louis, Mo.) to chemically induce lupus disease or of 0.5 ml PBS to generate age-matched, non-diseased control mice.

Assessment of Auto-Antibody Titers by ELISA.

Anti-dsDNA, -Sm/nRNP, -RiboP, and -Histone titers were evaluated by standard ELISA approach. Briefly, 96-well EIA/RIA ELISA plates (Corning) were coated with 100 ul of diluted antigen in PBS for 90 minutes at room temperature as follows (final concentrations indicated): 10 U/ml Sm/nRNP complex (Immunovision), 10 ug/ml calf thymus dsDNA (Sigma), 5 U/ml RiboP (Immunovision), and 5 ug/ml Histone (Immunovision). Plates were washed with PBS/0.05% Tween20 (washing buffer) and blocked overnight with PBS/1% BSA (blocking buffer) at 4° C. Plates were washed, mouse plasma samples diluted in blocking buffer (ranging from 1:25-1:10,000 depending on the model and the antigen) were added to wells in 100 ul volume per well, and plates were incubated for 90 minutes at room temperature. Plates were then washed, 100 ul anti-mouse-IgG-HRPO (Southern Biotech) diluted 1:50,000 in PBS/1% BSA/0.05% Tween was added to each well, and plates were incubated for 90 minutes at room temperature. Plates were washed, and 100 ul of a 1:1 mix of substrate components from the OptEIA TMB substrate kit (BD Biosciences) was added to the wells. Plates were incubated at room temperature, and after sufficient color development the reaction was stopped by adding 100 ul of 0.18M sulfuric acid solution. Plates were read by spectrophotometry at 450 nm.

Assessment of Proteinuria.

Urine was collected manually from individual mice or by housing 1-2 mice per metabolic cage for 18 hours, and the Urinary Albumin Creatinine Ratio (UACR) was determined for each animal as an indirect measure of kidney function (UACR calculated as the ratio of mg of albumin/g of creatinine per dL of urine). Albumin levels in the urine samples were determined using a custom sandwich ELISA protocol using an anti-mouse albumin antibody set (Bethyl Labs), which included a coating antibody and a secondary antibody tagged with an HRP conjugate for detection. Creatinine levels were determined using a commercial creatinine assay kit (Cayman).

Histological Assessment of Nephritis.

Kidneys were collected from individual mice, fixed in 10% formalin for 24 hours, embedded in paraffin, and H&E stained sections were generated for histopathology assessment in a blinded fashion. Features of Nephritis Disease Scores are as follows: Grade 0—normal limits; Grade 1—ribbon-like capillary wall thickening; Grade 2—hypercellularity, segmentation, crescent formation; Grade 3—see Grade 2, increased severity and extent (% glomeruli affected) of glomerular lesions; Grade 4—sclerosis; severe glomerular disease (non-functional organ).

Assessment of Interferon Gene Expression in Whole Blood.

The expression of IFN-regulated genes in whole blood was measured by qPCR. Briefly, mice were euthanized, blood was collected via the vena cava, and 100 ul was preserved in tubes containing RNAlater (Ambion, Austin Tex.). Total RNA was isolated using the Mouse RiboPure Blood RNA Isolation Kit (Ambion). RNA concentrations were determined using a NanoDrop ND-1000 spectrophotometer (Thermo Scientific, Waltham Mass.). First strand cDNA was synthesized from 100 ng total RNA using SuperScript® VILO™ Master Mix (Life Technologies, Grand Island, N.Y.). After reverse transcription, cDNA was diluted with nuclease-free water and mixed with TaqMan® Fast Advanced Master Mix (Applied Biosystems). The mixture was then applied to a custom TaqMan® Low Density Array (TLDA) manufactured by Applied Biosystems, and qPCR was performed on the ABI 7900HT Fast Real-time PCR System (Applied Biosystems). Raw data was collected using RQ Manager 1.2.1 (Applied Biosystems) and analyzed using GeneData Analyst 2.2 software (GeneData).

The TLDA panel contained as many as 45 target genes chosen from Table 7 below, and 3 housekeeping genes for normalization. The housekeeping gene Hprt1 was chosen for normalization based on coefficient-of-variation. Relative quantities were determined for the target genes and used to calculate a fold change for each diseased mouse relative to the non-diseased control group receiving intraperitoneal PBS injection only. A standard Student's t-test was performed to determine which target genes were significantly increased between the non-diseased group (PBS treated) and the vehicle-treated diseased group (pristane treated), thereby representing the disease-regulated gene set. An "IFN score" was subsequently calculated for each mouse as the median fold change of all disease-regulated genes identified in the t-test.

TABLE 7

| Gene symbol | Taqman ID | Gene name |
|---|---|---|
| 18S | Hs99999901_s1 | Eukaryotic 18S rRNA |
| Bst2 | Mm01609165_g1 | bone marrow stromal cell antigen 2 |
| C1qa | Mm00432142_m1 | complement component 1, q subcomponent, alpha polypeptide |
| C3 | Mm00437858_m1 | complement component 3 |
| C3ar1 | Mm02620006_s1 | complement component 3a receptor 1 |
| Ccl2 | Mm00441243_g1 | chemokine (C-C motif) ligand 2 |
| Ccl5 | Mm01302427_m1 | chemokine (C-C motif) ligand 5 |
| Ccr2 | Mm00438270_m1 | chemokine (C-C motif) receptor 2 |
| Cd274 | Mm00452054_m1 | CD274 antigen |
| Cd300e | Mm00468131_m1 | CD300e antigen |
| Cd38 | Mm01220906_m1 | CD38 antigen |
| Cd40 | Mm00441891_m1 | CD40 antigen |

TABLE 7-continued

| Gene symbol | Taqman ID | Gene name |
|---|---|---|
| Cdkn2c | Mm00483243_m1 | cyclin-dependent kinase inhibitor 2C (p18, inhibits CDK4) |
| Cmpk2 | Mm00469582_m1 | cytidine monophosphate (UMP-CMP) kinase 2 |
| Cxcl10 | Mm00445235_m1 | chemokine (C-X-C motif) ligand 10 |
| Cxcl11 | Mm00444662_m1 | chemokine (C-X-C motif) ligand 11 |
| Ddx60 | Mm00460708_m1 | DEAD (Asp-Glu-Ala-Asp) box polypeptide 60 |
| Elane | Mm00469310_m1 | elastase, neutrophil expressed |
| Epsti1 | Mm00712734_m1 | epithelial stromal interaction 1 (breast) |
| Fcgr1 | Mm00438874_m1 | Fc receptor, IgG, high affinity I |
| Fpr1 | Mm00442803_s1 | formyl peptide receptor 1 |
| Gapdh | Mm99999915_g1 | glyceraldehyde-3-phosphate dehydrogenase |
| Herc6 | Mm01341950_m1 | hect domain and RLD 6 |
| Hprt | Mm00446968_m1 | hypoxanthine guanine phosphoribosyl transferase |
| Ifi202b | Mm00839397_m1 | interferon activated gene 202B |
| Ifi204 | Mm00492602_m1 | interferon activated gene 204 |
| Ifi27l2a | Mm01329883_gH | interferon, alpha-inducible protein 27 like 2A |
| Ifi35 | Mm00510329_m1 | interferon-induced protein 35 |
| Ifi44 | Mm00505670_m1 | interferon-induced protein 44 |
| Ifih1 | Mm00459183_m1 | interferon induced with helicase C domain 1 |
| Ifit1 | Mm00515153_m1 | interferon-induced protein with tetratricopeptide repeats 1 |
| Ifit2 | Mm00492606_m1 | interferon-induced protein with tetratricopeptide repeats 2 |
| Ifit3 | Mm01704846_s1 | interferon-induced protein with tetratricopeptide repeats 3 |
| Il3ra | Mm00434273_m1 | interleukin 3 receptor, alpha chain |
| Il6 | Mm00446190_m1 | interleukin 6 |
| Il6ra | Mm00439653_m1 | interleukin 6 receptor, alpha |
| Irf5 | Mm00496477_m1 | interferon regulatory factor 5 |
| Irf7 | Mm00516788_m1 | interferon regulatory factor 7 |
| Isg15 | Mm01705338_s1 | ISG15 ubiquitin-like modifier |
| Isg20 | Mm00469585_m1 | interferon-stimulated protein |
| Lta | Mm00440228_gH | lymphotoxin A |
| Ly6e | Mm01200460_g1 | lymphocyte antigen 6 complex, locus E |
| Mmp8 | Mm00439509_m1 | matrix metallopeptidase 8 |
| Mmp9 | Mm00442991_m1 | matrix metallopeptidase 9 |
| Mpo | Mm00447886_m1 | myeloperoxidase |
| Ms4a6c | Mm00459296_m1 | membrane-spanning 4-domains, subfamily A, member 6C |
| Mx1 | Mm00487796_m1 | myxovirus (influenza virus) resistance 1 |
| Oas3 | Mm00460944_m1 | 2-5 oligoadenylate synthetase 3 |
| Oasl2 | Mm00496187_m1 | 2-5 oligoadenylate synthetase-like 2 |
| Ppia | Mm02342430_g1 | peptidylprolyl isomerase A (cyclophilin A) |
| Prf1 | Mm00812512_m1 | perforin 1 (pore forming protein) |
| Rsad2 | Mm00491265_m1 | radical S-adenosyl methionine domain containing 2 |
| Siglec1 | Mm00488332_m1 | sialic acid binding Ig-like lectin 1, sialoadhesin |
| Stat1 | Mm00439531_m1 | signal transducer and activator of transcription 1 |
| Tlr7 | Mm00446590_m1 | toll-like receptor 7 |
| Tlr9 | Mm00446193_m1 | toll-like receptor 9 |
| Tnf | Mm00443258_m1 | tumor necrosis factor |
| Tnfsf10 | Mm01283606_m1 | tumor necrosis factor (ligand) superfamily, member 10 |
| Tnfsf13b | Mm00446347_m1 | tumor necrosis factor (ligand) superfamily, member 13b |
| Treml4 | Mm00553947_m1 | triggering receptor expressed on myeloid cells-like 4 |
| Trex1 | Mm00810120_s1 | three prime repair exonuclease 1 |
| Usp18 | Mm00449455_m1 | ubiquitin specific peptidase 18 |
| Xaf1 | Mm01248390_m1 | XIAP associated factor 1 |

We claim:

1. A compound of Formula (I) or a pharmaceutically acceptable salt thereof:

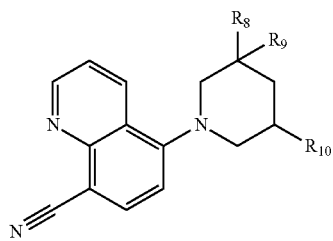

or a stereoisomer thereof or mixture of stereoisomers thereof, wherein:
$R_8$ is H or methyl;
$R_9$ is —H, methyl, or hydroxyl;
$R_{10}$ is hydroxyl or $NR_{11}R_{12}$; and
wherein $R_{11}$ and $R_{12}$ are independently selected, and wherein:
$R_{11}$ is —H, methyl, or —$CH_2$—C(O)$CH_2CH_3$; and
$R_{12}$ is
—H, oxopyrrolidinyl, dioxidothiopyranyl, isopropylsulfonyl, tetrahydropyranyl, oxetanyl, tetrahydrofuranyl, hydroxyl, dimethylaminethanesulfonyl, aminethanesulfonyl, dimethylaminpropanesulfonyl,
$C_1$-$C_6$ alkyl that is linear, branched, or cyclic, optionally substituted with methoxy, —F, ≡N, methyl oxetanyl, ethoxy, oxo-, methyl imidazolyl, methylthio piperazinyl optionally substituted with methyl or —CF3,
acetamidyl optionally substituted with methyl or ethyl, oxazolyl optionally substituted with methyl,
pyrazolyl optionally substituted with methyl, cyano, or hydroxyl,
—C(O)$R_{13}$, wherein
$R_{13}$ is
$C_1$ to $C_7$ alkyl that is cyclic, branched, or linear, optionally substituted with $NR_{15}R_{14}$, wherein $R_{15}$ and $R_{14}$ are independently selected from methyl and —H;
methoxy, hydroxyl, methylthio, ethylthio, methylsulfonyl, oxo-, thiazolidinyl, pyridinyl, pyrazolopyridinyl, methyl amino, thiazolyl, —F, morpholinyl, methylisoxazolyl, methyl oxetanyl, aminooxetanyl, phenyl optionally substituted with hydroxyl, —C(O)$NH_2$;
a five membered cycloalkyl, saturated or unsaturated, in which 1 or 2 carbon atoms are replaced by nitrogen atoms, wherein the cycloamine or cyclodiamine is optionally substituted with hydroxyl or methyl.

2. A compound selected from the group consisting of:
(R)-5-(3-aminopiperidin-1-yl)quinoline-8-carbonitrile;
5-((3R,5S)-3-amino-5-methylpiperidin-1-yl)quinoline-8-carbonitrile;
5-((3R,5S)-3-(dimethylamino)-5-methylpiperidin-1-yl)quinoline-8-carbonitrile;
(R)-5-(5-amino-3,3-dimethylpiperidin-1-yl)quinoline-8-carbonitrile;
N-((3R,5S)-1-(8-cyanoquinolin-5-yl)-5-methylpiperidin-3-yl)acetamide;
5-((3R,5S)-3-hydroxy-5-methylpiperidin-1-yl)quinoline-8-carbonitrile;
5-((3S,5R)-3-methyl-5-(methylamino)piperidin-1-yl)quinoline-8-carbonitrile;
N-((3R,5S)-1-(8-cyanoquinolin-5-yl)-5-methylpiperidin-3-yl)-2-(dimethylamino)acetamide;
N-((3R,5S)-1-(8-cyanoquinolin-5-yl)-5-methylpiperidin-3-yl)-2-methoxyacetamide;
2-amino-N-((3R,5S)-1-(8-cyanoquinolin-5-yl)-5-methylpiperidin-3-yl)acetamide;
5-((3R,5S)-3-((2-methoxyethyl)amino)-5-methylpiperidin-1-yl)quinoline-8-carbonitrile;
5-((3R,5S)-3-((2-methoxyethyl)amino)-5-methylpiperidin-1-yl)quinoline-8-carbonitrile 2-hydroxypropane-1,2,3-tricarboxylate;
2-amino-N-((3R,5S)-1-(8-cyanoquinolin-5-yl)-5-methylpiperidin-3-yl)-2-methylpropanamide;
N-((3R,5S)-1-(8-cyanoquinolin-5-yl)-5-methylpiperidin-3-yl)-2-(methylamino)acetamide;

5-((3R,5S)-3-amino-5-methylpiperidin-1-yl)quinoline-8-carboxamide;
N-((3R,5S)-1-(8-cyanoquinolin-5-yl)-5-methylpiperidin-3-yl)-2-hydroxyacetamide;
(S)—N-((3R,5S)-1-(8-cyanoquinolin-5-yl)-5-methylpiperidin-3-yl)-2-hydroxy-3-methylbutanamide;
N-((3R,5S)-1-(8-cyanoquinolin-5-yl)-5-methylpiperidin-3-yl)-3-hydroxybenzamide;
N-((3R,5S)-1-(8-cyanoquinolin-5-yl)-5-methylpiperidin-3-yl)-4-hydroxybenzamide;
N-((3R,5S)-1-(8-cyanoquinolin-5-yl)-5-methylpiperidin-3-yl)-2-(methylthio)acetamide;
N-((3R,5S)-1-(8-cyanoquinolin-5-yl)-5-methylpiperidin-3-yl)-2-(ethylthio)acetamide;
N-((3R,5S)-1-(8-cyanoquinolin-5-yl)-5-methylpiperidin-3-yl)-2-(methylsulfonyl)acetamide;
(S)-2-amino-N-((3R,5S)-1-(8-cyanoquinolin-5-yl)-5-methylpiperidin-3-yl)propanamide;
(R)-2-amino-N-((3R,5S)-1-(8-cyanoquinolin-5-yl)-5-methylpiperidin-3-yl)propanamide;
1-amino-N-((3R,5S)-1-(8-cyanoquinolin-5-yl)-5-methylpiperidin-3-yl)cyclopropanecarboxamide;
(R)-2-amino-N-((3R,5S)-1-(8-cyanoquinolin-5-yl)-5-methylpiperidin-3-yl)-3-hydroxypropanamide;
(R)—N-((3R,5S)-1-(8-cyanoquinolin-5-yl)-5-methylpiperidin-3-yl)pyrrolidine-2-carboxamide;
2-(azetidin-3-yl)-N-((3R,5S)-1-(8-cyanoquinolin-5-yl)-5-methylpiperidin-3-yl)acetamide;
N-((3R,5S)-1-(8-cyanoquinolin-5-yl)-5-methylpiperidin-3-yl)pyrrolidine-3-carboxamide;
2-amino-N-((3R,5S)-1-(8-cyanoquinolin-5-yl)-5-methylpiperidin-3-yl)-3-methylbutanamide;
(S)-2-amino-N-((3R,5S)-1-(8-cyanoquinolin-5-yl)-5-methylpiperidin-3-yl)-3-methylbutanamide;
5-amino-N-((3R,5S)-1-(8-cyanoquinolin-5-yl)-5-methylpiperidin-3-yl)pentanamide;
(S)-2-amino-N-((3R,5S)-1-(8-cyanoquinolin-5-yl)-5-methylpiperidin-3-yl)pentanamide;
(S)-2-amino-N-((3R,5S)-1-(8-cyanoquinolin-5-yl)-5-methylpiperidin-3-yl)-3-methoxypropanamide;
(2R,3S)-2-amino-N-((3R,5S)-1-(8-cyanoquinolin-5-yl)-5-methylpiperidin-3-yl)-3-hydroxybutanamide;
N-((3R,5S)-1-(8-cyanoquinolin-5-yl)-5-methylpiperidin-3-yl)piperidine-4-carboxamide;
N-((3R,5S)-1-(8-cyanoquinolin-5-yl)-5-methylpiperidin-3-yl)piperidine-3-carboxamide;
N-((3R,5S)-1-(8-cyanoquinolin-5-yl)-5-methylpiperidin-3-yl)-2-(pyrrolidin-3-yl)acetamide;
N-((3R,5S)-1-(8-cyanoquinolin-5-yl)-5-methylpiperidin-3-yl)piperazine-2-carboxamide;
(2S,4R)—N-((3R,5S)-1-(8-cyanoquinolin-5-yl)-5-methylpiperidin-3-yl)-4-hydroxypyrrolidine-2-carboxamide;
(2S,3S)-2-amino-N-((3R,5S)-1-(8-cyanoquinolin-5-yl)-5-methylpiperidin-3-yl)-3-methylpentanamide;
(R)-2-amino-N-((3R,5S)-1-(8-cyanoquinolin-5-yl)-5-methylpiperidin-3-yl)-4-methylpentanamide;
(S)-2-amino-N-((3R,5S)-1-(8-cyanoquinolin-5-yl)-5-methylpiperidin-3-yl)-4-methylpentanamide;
(S)-2-amino-N-((3R,5S)-1-(8-cyanoquinolin-5-yl)-5-methylpiperidin-3-yl)-3,3-dimethylbutanamide;
2-amino-N-((3R,5S)-1-(8-cyanoquinolin-5-yl)-5-methylpiperidin-3-yl)-3,3-dimethylbutanamide;
N-((3R,5S)-1-(8-cyanoquinolin-5-yl)-5-methylpiperidin-3-yl)-3-methyl-2-(methylamino)butanamide;
(S)-3-amino-N1-((3R,5S)-1-(8-cyanoquinolin-5-yl)-5-methylpiperidin-3-yl)succinamide;
(S)-2-amino-N1-((3R,5S)-1-(8-cyanoquinolin-5-yl)-5-methylpiperidin-3-yl)succinamide;
(R)-2-amino-N1-((3R,5S)-1-(8-cyanoquinolin-5-yl)-5-methylpiperidin-3-yl)succinamide;
(S)—N-((3R,5S)-1-(8-cyanoquinolin-5-yl)-5-methylpiperidin-3-yl)thiazolidine-4-carboxamide;
4-amino-N-((3R,5S)-1-(8-cyanoquinolin-5-yl)-5-methylpiperidin-3-yl)benzamide;
N-((3R,5S)-1-(8-cyanoquinolin-5-yl)-5-methylpiperidin-3-yl)-2-(piperidin-4-yl)acetamide;
N-((3R,5S)-1-(8-cyanoquinolin-5-yl)-5-methylpiperidin-3-yl)-4-methylpiperidine-4-carboxamide;
1-amino-N-((3R,5S)-1-(8-cyanoquinolin-5-yl)-5-methylpiperidin-3-yl)-3-hydroxycyclopentanecarboxamide;
(S)—N-((3R,5S)-1-(8-cyanoquinolin-5-yl)-5-methylpiperidin-3-yl)-3-methyl-2-(methylamino)butanamide;
(S)-2-amino-N-((3R,5S)-1-(8-cyanoquinolin-5-yl)-5-methylpiperidin-3-yl)-4,4-dimethylpentanamide;
(S)—N-((3R,5S)-1-(8-cyanoquinolin-5-yl)-5-methylpiperidin-3-yl)-2-(methylamino)hexanamide;
(S)-2-amino-N-((3R,5S)-1-(8-cyanoquinolin-5-yl)-5-methylpiperidin-3-yl)pentanediamide;
(R)-2-amino-N-((3R,5S)-1-(8-cyanoquinolin-5-yl)-5-methylpiperidin-3-yl)-3-(ethylthio)propanamide;
2-amino-N-((3R,5S)-1-(8-cyanoquinolin-5-yl)-5-methylpiperidin-3-yl)-4-(methylthio)butanamide;
(R)-2-amino-N-((3R,5S)-1-(8-cyanoquinolin-5-yl)-5-methylpiperidin-3-yl)-2-phenylacetamide;
(S)-2-amino-N-((3R,5S)-1-(8-cyanoquinolin-5-yl)-5-methylpiperidin-3-yl)-2-phenylacetamide;
(S)-2-amino-N-((3R,5S)-1-(8-cyanoquinolin-5-yl)-5-methylpiperidin-3-yl)-3-(1H-imidazol-5-yl)propanamide;
N-((3R,5S)-1-(8-cyanoquinolin-5-yl)-5-methylpiperidin-3-yl)-3-(piperidin-2-yl)propanamide;
N-((3R,5S)-1-(8-cyanoquinolin-5-yl)-5-methylpiperidin-3-yl)-3-(piperidin-3-yl)propanamide;
1-amino-N-((3R,5S)-1-(8-cyanoquinolin-5-yl)-5-methylpiperidin-3-yl)-4-hydroxycyclohexanecarboxamide;
(R)-2-amino-N-((3R,5S)-1-(8-cyanoquinolin-5-yl)-5-methylpiperidin-3-yl)-3-phenylpropanamide;
(2S)-2-amino-N-((3R,5S)-1-(8-cyanoquinolin-5-yl)-5-methylpiperidin-3-yl)-4-(methylsulfinyl)butanamide;
(S)-2-amino-N-((3R,5S)-1-(8-cyanoquinolin-5-yl)-5-methylpiperidin-3-yl)-3-(pyridin-2-yl)propanamide;
(S)-2-amino-N-((3R,5S)-1-(8-cyanoquinolin-5-yl)-5-methylpiperidin-3-yl)-3-(pyridin-4-yl)propanamide;
(S)-2-amino-N-((3R,5S)-1-(8-cyanoquinolin-5-yl)-5-methylpiperidin-3-yl)-3-(pyridin-3-yl)propanamide;
(R)-2-amino-N-((3R,5S)-1-(8-cyanoquinolin-5-yl)-5-methylpiperidin-3-yl)-3-(pyridin-4-yl)propanamide;
N-((3R,5S)-1-(8-cyanoquinolin-5-yl)-5-methylpiperidin-3-yl)-4,5,6,7-tetrahydro-1H-pyrazolo[4,3-c]pyridine-3-carboxamide;
2-(1-(aminomethyl)cyclohexyl)-N-((3R,5S)-1-(8-cyanoquinolin-5-yl)-5-methylpiperidin-3-yl)acetamide;
(S)-2-amino-N-((3R,5S)-1-(8-cyanoquinolin-5-yl)-5-methylpiperidin-3-yl)-3-(thiazol-4-yl)propanamide;
(S)—N-((3R,5S)-1-(8-cyanoquinolin-5-yl)-5-methylpiperidin-3-yl)-2-(methylamino)-3-phenylpropanamide;
(R)—N-((3R,5S)-1-(8-cyanoquinolin-5-yl)-5-methylpiperidin-3-yl)-2-(methylamino)-3-phenylpropanamide;
(S)-2-amino-N-((3R,5S)-1-(8-cyanoquinolin-5-yl)-5-methylpiperidin-3-yl)-3-(4-hydroxyphenyl)propanamide;
(S)-2-amino-N-((3R,5S)-1-(8-cyanoquinolin-5-yl)-5-methylpiperidin-3-yl)-4-(methylsulfonyl)butanamide;

N-((3R,5S)-1-(8-cyanoquinolin-5-yl)-5-methylpiperidin-3-yl)-2,2,2-trifluoroacetamide;
N-((3R,5S)-1-(8-cyanoquinolin-5-yl)-5-methylpiperidin-3-yl)propane-2-sulfonamide;
N-((3R,5S)-1-(8-cyanoquinolin-5-yl)-5-methylpiperidin-3-yl)-3,3,3-trifluoropropanamide;
(S)-3-amino-N-((3R,5S)-1-(8-cyanoquinolin-5-yl)-5-methylpiperidin-3-yl)-4-methylpentanamide;
(S)-3-amino-N-((3R,5S)-1-(8-cyanoquinolin-5-yl)-5-methylpiperidin-3-yl)butanamide;
5-((3S,5R)-3-methyl-5-((2,2,2-trifluoroethyl)amino)piperidin-1-yl)quinoline-8-carbonitrile;
5-((3R,5S)-3-((2,2-difluoroethyl)amino)-5-methylpiperidin-1-yl)quinoline-8-carbonitrile;
N-((3R,5S)-1-(8-cyanoquinolin-5-yl)-5-methylpiperidin-3-yl)morpholine-2-carboxamide;
(S)—N-((3R,5S)-1-(8-cyanoquinolin-5-yl)-5-methylpiperidin-3-yl)-2-(methylamino)propanamide;
(R)-3-amino-N-((3R,5S)-1-(8-cyanoquinolin-5-yl)-5-methylpiperidin-3-yl)-4-methylpentanamide;
N-((3R,5S)-1-(8-cyanoquinolin-5-yl)-5-methylpiperidin-3-yl)-5-methylisoxazole-3-carboxamide;
(R)-3-amino-N-((3R,5S)-1-(8-cyanoquinolin-5-yl)-5-methylpiperidin-3-yl)butanamide;
(S)—N-((3R,5S)-1-(8-cyanoquinolin-5-yl)-5-methylpiperidin-3-yl)-3-methyl-2-(methylamino)butanamide;
N-((3R,5S)-1-(8-cyanoquinolin-5-yl)-5-methylpiperidin-3-yl)-2-(1H-imidazol-5-yl)acetamide;
N-((3R,5S)-1-(8-cyanoquinolin-5-yl)-5-methylpiperidin-3-yl)-2-(pyridin-2-yl)acetamide;
N-((3R,5S)-1-(8-cyanoquinolin-5-yl)-5-methylpiperidin-3-yl)-2-(1H-pyrazol-1-yl)acetamide;
N-((3R,5S)-1-(8-cyanoquinolin-5-yl)-5-methylpiperidin-3-yl)-1H-pyrazole-4-carboxamide;
N-((3R,5S)-1-(8-cyanoquinolin-5-yl)-5-methylpiperidin-3-yl)nicotinamide;
N-((3R,5S)-1-(8-cyanoquinolin-5-yl)-5-methylpiperidin-3-yl)-1-methyl-1H-imidazole-5-carboxamide;
N-((3R,5S)-1-(8-cyanoquinolin-5-yl)-5-methylpiperidin-3-yl)-1-methyl-1H-pyrazole-5-carboxamide;
(S)-2-amino-N-((3R,5S)-1-(8-cyanoquinolin-5-yl)-5-methylpiperidin-3-yl)-3,3,3-trifluoropropanamide;
(R)-2-amino-N-((3R,5S)-1-(8-cyanoquinolin-5-yl)-5-methylpiperidin-3-yl)-3,3,3-trifluoropropanamide;
5-((3S,5R)-3-methyl-5-((3,3,3-trifluoropropyl)amino)piperidin-1-yl)quinoline-8-carbonitrile;
5-((3R,5S)-3-((cyanomethyl)amino)-5-methylpiperidin-1-yl)quinoline-8-carbonitrile;
N-((3R,5S)-1-(8-cyanoquinolin-5-yl)-5-methylpiperidin-3-yl)-3-methyloxetane-3-carboxamide;
5-((3S,5R)-3-methyl-5-(((3-methyloxetan-3-yl)methyl)amino)piperidin-1-yl)quinoline-8-carbonitrile;
(R)—N-((3R,5S)-1-(8-cyanoquinolin-5-yl)-5-methylpiperidin-3-yl)morpholine-3-carboxamide;
(S)—N-((3R,5S)-1-(8-cyanoquinolin-5-yl)-5-methylpiperidin-3-yl)morpholine-3-carboxamide;
3-amino-N-((3R,5S)-1-(8-cyanoquinolin-5-yl)-5-methyl piperidin-3-yl)oxetane-3-carboxamide;
5-((3S,5S)-3-(((3-aminooxetan-3-yl)methyl)amino)-5-methylpiperidin-1-yl)quinoline-8-carbonitrile;
ethyl 2-(((3R,5S)-1-(8-cyanoquinolin-5-yl)-5-methylpiperidin-3-yl)amino)acetate;
diethyl 2,2'-(((3R,5S)-1-(8-cyanoquinolin-5-yl)-5-methylpiperidin-3-yl)azanediyl)diacetate;
5-((3S,5R)-3-methyl-5-((tetrahydro-2H-pyran-4-yl)amino)piperidin-1-yl)quinoline-8-carbonitrile;
5-((3R,5S)-3-(ethylamino)-5-methylpiperidin-1-yl)quinoline-8-carbonitrile;
5-((3S,5R)-3-methyl-5-(oxetan-3-ylamino)piperidin-1-yl)quinoline-8-carbonitrile;
5-((3S,5R)-3-methyl-5-(((5-(trifluoromethyl)pyridin-2-yl)methyl)amino)piperidin-1-yl)quinoline-8-carbonitrile;
5-((3S,5R)-3-methyl-5-((tetrahydrofuran-3-yl)amino)piperidin-1-yl)quinoline-8-carbonitrile;
2-(((3R,5S)-1-(8-cyanoquinolin-5-yl)-5-methylpiperidin-3-yl)amino)acetamide;
2-(((3R,5S)-1-(8-cyanoquinolin-5-yl)-5-methylpiperidin-3-yl)amino)-N-methylacetamide;
2-(((3R,5S)-1-(8-cyanoquinolin-5-yl)-5-methylpiperidin-3-yl)amino)-N-ethylacetamide;
2-(((3R,5S)-1-(8-cyanoquinolin-5-yl)-5-methylpiperidin-3-yl)amino)-N,N-dimethylacetamide;
5-((3S,5R)-3-methyl-5-((oxazol-2-yl methyl)amino)piperidin-1-yl)quinoline-8-carbonitrile;
5-((3S,5R)-3-methyl-5-(((1-methyl-1H-imidazol-4-yl)methyl)amino)piperidin-1-yl)quinoline-8-carbonitrile;
5-((3S,5R)-3-methyl-5-(((6-(trifluoromethyl)pyridin-3-yl)methyl)amino)piperidin-1-yl)quinoline-8-carbonitrile;
5-((3R,5S)-3-(((1H-pyrazol-5-yl)methyl)amino)-5-methylpiperidin-1-yl)quinoline-8-carbonitrile;
5-((3R,5S)-3-(((1,4-dimethyl-1H-pyrazol-3-yl)methyl)amino)-5-methylpiperidin-1-yl)quinoline-8-carbonitrile;
5-((3R,5S)-3-(((3,5-dimethylisoxazol-4-yl)methyl)amino)-5-methylpiperidin-1-yl)quinoline-8-carbonitrile;
5-((3S,5R)-3-methyl-5-((2-oxopyrrolidin-3-yl)amino)piperidin-1-yl)quinoline-8-carbonitrile;
5-((3S,5R)-3-methyl-5-((3-(methylsulfonyl)propyl)amino)piperidin-1-yl)quinoline-8-carbonitrile;
5-((3R,5S)-3-((2-cyanocyclopentyl)amino)-5-methylpiperidin-1-yl)quinoline-8-carbonitrile;
5-((3S, 5R)-3-methyl-5-((1-(pyridin-2-yl)ethyl)amino)piperidin-1-yl)quinoline-8-carbonitrile;
5-((3S,5R)-3-methyl-5-((tetrahydro-2H-pyran-3-yl)amino)piperidin-1-yl)quinoline-8-carbonitrile;
5-((3R,5S)-3-(((1S,4S)-4-hydroxycyclohexyl)amino)-5-methylpiperidin-1-yl)quinoline-8-carbonitrile;
5-((3R,5S)-3-(((1R,4R)-4-hydroxycyclohexyl)amino)-5-methylpiperidin-1-yl)quinoline-8-carbonitrile;
5-((3S,5R)-3-methyl-5-((4-oxocyclohexyl)amino)piperidin-1-yl)quinoline-8-carbonitrile;
5-((3R,5S)-3-((1,1-dioxidotetrahydro-2H-thiopyran-4-yl)amino)-5-methylpiperidin-1-yl)quinoline-8-carbonitrile;
5-((3S,5R)-3-methyl-5-((1-(6-methylpyridin-2-yl)ethyl)amino)piperidin-1-yl)quinoline-8-carbonitrile;
2-amino-N-((3R,5S)-1-(8-cyanoquinolin-5-yl)-5-methyl piperidin-3-yl)ethanesulfonamide;
N-((3R,5S)-1-(8-cyanoquinolin-5-yl)-5-methylpiperidin-3-yl)-2-(dimethylamino)ethanesulfonamide;
N-((3R,5S)-1-(8-cyanoquinolin-5-yl)-5-methylpiperidin-3-yl)-3-(dimethylamino)propane-1-sulfonamide;
5-((3S,5R)-3-methyl-5-(methyl(oxetan-3-yl)amino)piperidin-1-yl)quinoline-8-carbonitrile acetate; and
5-((5S)-3-((1-hydroxypropan-2-yl)amino)-5-methyl piperidin-1-yl)quinoline-8-carbonitrile;
or pharmaceutically acceptable salt thereof.

3. The compound or pharmaceutically acceptable salt of claim 1, wherein said compound or salt is 5-((3R,5S)-3- amino-5-methylpiperidin-1-yl)quinoline-8-carbonitrile or pharmaceutically acceptable salt thereof.

4. A method for treatment of systemic lupus erythematosus or lupus, comprising administering a pharmaceutically effective amount of the compound or pharmaceutically acceptable salt of claim 1.

5. The method of claim 4, wherein the administration comprises administration as the pharmaceutically acceptable salt.

6. A method for antagonizing TLR7, comprising administering a pharmaceutically effective amount of the compound or pharmaceutically acceptable salt of claim 1.

7. A method for antagonizing TLR8, comprising administering a pharmaceutically effective amount of the compound or pharmaceutically acceptable salt of claim 1.

8. A pharmaceutical composition comprising at least one of the compound or pharmaceutically acceptable salt of claim 1 and at least one pharmaceutically acceptable carrier.

9. The pharmaceutical composition of claim 8, wherein said compound or pharmaceutically acceptable salt has an IC50 less than or equal to 100 nM against human TLR7 receptors in a HEK-293 cell line.

10. The pharmaceutical composition of claim 8, wherein said compound or pharmaceutically acceptable salt has an IC50 less than or equal to 20 nM against human TLR7 receptors expressed in a HEK-293 cell line.

11. The pharmaceutical composition of claim 8, wherein said compound or pharmaceutically acceptable salt has an IC50 less than or equal to 5 nM against human TLR7 receptors expressed in a HEK-293 cell line.

12. The pharmaceutical composition of claim 9, wherein the IC50 against human TLR7 receptors expressed in a HEK-293 cell line is measured by (1) plating cells of the HEK-293 cell line stably expressing TLR7 in Dulbecco's modified Eagle's medium containing 10% fetal bovine serum at a density of 2.22×105 cells/ml into a 384-well plate and incubating for 2 days at 37° C., 5% CO2; (2) adding the compound or pharmaceutically acceptable salt and incubating the cells for 30 minutes; (3) adding CL097 (InvivoGen) at 3 ug/ml and incubating the cells for approximately 20 hours; and (4) quantifying NF-kappaB dependent reporter activation by measuring luminescence.

13. A method for treatment of a systematic lupus erythematosus, cutaneous lupus, neuropsychiatric lupus, or lupus, comprising administering a pharmaceutically effective amount of the compound or pharmaceutically acceptable salt of claim 1.

14. The method of claim 13, wherein said compound is administered as the pharmaceutically acceptable salt.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: synthetic construct

<400> SEQUENCE: 1
tcgtcgttaa gtcgttaagt cgtt         24

<210> SEQ ID NO 2
<211> LENGTH: 24
<212> TYPE: RNA
<213> ORGANISM: Artificial Sequence
<220> FEATURE:
<223> OTHER INFORMATION: synthetic construct

<400> SEQUENCE: 2
gggggacugc guucgcgcuu uccc         24

UNITED STATES PATENT AND TRADEMARK OFFICE
CERTIFICATE OF CORRECTION

PATENT NO. : 9,663,486 B2
APPLICATION NO. : 14/908164
DATED : May 30, 2017
INVENTOR(S) : Roch Boivin et al.

Page 1 of 1

It is certified that error appears in the above-identified patent and that said Letters Patent is hereby corrected as shown below:

In the Claims

Claim 13, Column 50, Line 18: that portion of the claim reading "systematic" should read
-- systemic --

Signed and Sealed this
Twenty-fourth Day of August, 2021

Drew Hirshfeld
*Performing the Functions and Duties of the
Under Secretary of Commerce for Intellectual Property and
Director of the United States Patent and Trademark Office*